US011466056B2

(12) United States Patent
Leoni et al.

(10) Patent No.: US 11,466,056 B2
(45) Date of Patent: Oct. 11, 2022

(54) HERPESVIRUS WITH MODIFIED GLYCOPROTEIN D

(71) Applicant: ALMA MATER STUDIORUM UNIVERSITA DI BOLOGNA, Bologna (IT)

(72) Inventors: Valerio Leoni, Faenza (IT); Maria Gabriella Campadelli, Bologna (IT)

(73) Assignee: ALMA MATER STUDIORUM—UNIVERSITÀ DI BOLOGNA, Bologna (IT)

( * ) Notice: Subject to any disclaimer, the term of this patent is extended or adjusted under 35 U.S.C. 154(b) by 848 days.

(21) Appl. No.: 16/307,719

(22) PCT Filed: Jun. 8, 2017

(86) PCT No.: PCT/EP2017/063948
§ 371 (c)(1),
(2) Date: Dec. 6, 2018

(87) PCT Pub. No.: WO2017/211944
PCT Pub. Date: Dec. 14, 2017

(65) Prior Publication Data

US 2019/0309024 A1 Oct. 10, 2019

(30) Foreign Application Priority Data

Jun. 9, 2016 (EP) .................................... 16173830
Feb. 15, 2017 (EP) ...................................... 1700247

(51) Int. Cl.

| | |
|---|---|
| *C07K 14/005* | (2006.01) |
| *A61P 35/00* | (2006.01) |
| *A61K 35/763* | (2015.01) |
| *A61K 45/06* | (2006.01) |
| *C07K 14/39* | (2006.01) |
| *C07K 16/32* | (2006.01) |
| *C12N 5/09* | (2010.01) |
| *C12N 7/00* | (2006.01) |

(52) U.S. Cl.
CPC .......... *C07K 14/005* (2013.01); *A61K 35/763* (2013.01); *A61K 45/06* (2013.01); *A61P 35/00* (2018.01); *C07K 14/39* (2013.01); *C07K 16/32* (2013.01); *C12N 5/0693* (2013.01); *C12N 7/00* (2013.01); *C07K 2317/622* (2013.01); *C07K 2319/00* (2013.01); *C07K 2319/30* (2013.01); *C12N 2710/16622* (2013.01); *C12N 2710/16632* (2013.01)

(58) Field of Classification Search
CPC .... C07K 14/005; C07K 14/035; C07K 19/00; C12N 2710/16611; C12N 2710/16632
See application file for complete search history.

(56) References Cited

FOREIGN PATENT DOCUMENTS

| | | |
|---|---|---|
| WO | 2003/068809 | 8/2003 |
| WO | 2004/033639 | 4/2004 |
| WO | 2007/027774 | 3/2007 |
| WO | 2007024668 A1 | 3/2007 |
| WO | 2008103762 A2 | 8/2008 |
| WO | 2009/013448 | 1/2009 |
| WO | 2009144755 A2 | 12/2009 |
| WO | 2011130749 A2 | 10/2011 |
| WO | 2015066042 A2 | 5/2015 |
| WO | 2016/128497 | 8/2016 |

OTHER PUBLICATIONS

Kamiyama, H. et al., "Herpes simplex virus 1 recombinant virions exhibiting the amino terminal fragment of urokinase-type plasminogen activator can enter cells via the cognate receptor," Gene Therapy, vol. 13, No. 7, Nov. 17, 2005, pp. 621-629.
Leoni, V. et al., "A Strategy for Cultivation of Retargeted Oncolytic Herpes Simplex Viruses in Non-cancer Cells," Journal of Virology, vol. 91, No. 10, Mar. 1, 2017, pp. e00067-17 (13 pages).
Menotti, L. et al., "Construction of a Fully Retargeted Herpes Simplex Virus I Recombinant Capable of Entering Cells Solely via Human Epidermal Growth Factor Receptor 2," Journal of Virology, The American Society for Microbiology, US, vol. 82, No. 20, Oct. 1, 2008, pp. 10153-01061.
Menotti, L. et al., "Inhibition of human tumor growth in mice by an oncolytic herpes simplex virus designed to target solely HER-2-positive cells," Proceedings National Academy of Sciences PNAS, vol. 106, No. 22, Jun. 2, 2009, pp. 9039-9044.
Shibata, T. et al., "Development of an oncolytic HSV vector fully retargeted specifically to cellular EpCAM for virus entry and cell-to-cell spread," Gene Therapy, vol. 23, No. 6, Feb. 23, 2016, pp. 479-488.
Uchida, H. et al., "Effective Treatment of an Orthotopic Xenograft Model of Human Glioblastoma Using an EGFR-retargeted Oncolytic Herpes Simplex Virus," Molecular Therapy, vol. 21, No. 3, Oct. 16, 2012, pp. 561-569.
International Search Report and Written Opinion for Corresponding PCT Patent Application No. PCT/EP2017/063498, dated Sep. 19, 2017 (18 pages).

(Continued)

*Primary Examiner* — Karen Cochrane Carlson
(74) *Attorney, Agent, or Firm* — Sterne, Kessler, Goldstein & Fox P.L.L.C.

(57) ABSTRACT

The present invention is directed to a recombinant herpesvirus comprising a heterologous peptide and optionally polypeptide ligand capable of binding to (a) target molecule(s) and fused to or inserted into glycoprotein D. The recombinant herpesvirus may additionally comprise modifications for detargeting the virus from the natural receptors of gD. This allows the herpesvirus to efficiently target a cell for therapeutic purposes and a cell for virus production. The present invention further comprises a pharmaceutical composition comprising the herpesvirus, the herpesvirus for use in the treatment of a tumor, infection, degenerative disorder or senescence-associated disease, a nucleic acid and a vector coding for the gD, a polypeptide comprising the gD, and a cell comprising the herpesvirus, nucleic acid, vector or polypeptide. Moreover, a method for infecting a cell with the herpesvirus or for producing the herpesvirus is disclosed.

16 Claims, 10 Drawing Sheets

Specification includes a Sequence Listing.

(56) References Cited

OTHER PUBLICATIONS

Arii J. et al., "Non-Muscle Myosin IIA is a Functional Entry Receptor for Herpes Simplex Virus-1", Nature, 2010, 467, 859-862.
Arndt K. and Fin G.R., "GCN4 Protein, a Positive Transcription Factor in Yeast, Binds General Control Promoters at All 5' TGACTC 3' Sequences", PNAS 1986, 83, 8516-8520.
Avitabile E. et al., "Complexes Bewteen Herpes Simplex Virus Glycoproteins gD, gB, and gH Detected in Cells by Complementation of Split Enhanced Green Fluorecent Protein", Journal of Virology, 2007, 81, 11532-11537.
Backovic M. et al., "Structure of a Trimeric Variant of the Epstein-Barr Virus Glycoprotein B", PNAS, 2009, 106, 2880-2885.
Backovic M. et al., "Structure of a Core Fragment of Glycoprotein H from Pseudorabies Virus in Complex with Antibody", PNAS, 2010, 107, 22635-22640.
Bender F.C. et al., "Antigenic and Mutational Analyses of Herpes Simplex Virus Glycoprotein B Reveal Four Functional Regions", J Virol., 2007, 81, 3827-3841.
Burke H.G. and Heldwein E.E., "Crystal Structure of the Human Cytomegalovirus Glycoprotein B", PLOS Pathogens, 2015, 11, e1005227.
Burleson, F.G. et al., Virology: A Laboratory Manual, 1992, ISBN-13: 978-0121447304.
Cairns T.M. et al., "Structure-Function Analysis of Herpes Simplex Virus Type 1 gD and gH-gL: Clues from gDgH Chimeras", Journal of Virology, 2003, 77, 6731-6742.
Castoldi R. et al., "Molecular Characterization of Novel Trispecific ErbB-cMet-IGFIR Antibodies and Their Antigen-Binding Properties", Protein Eng Des Sel, 2012, 25, 551-559.
Castoldi R. et al., "A Novel Bispecific EGFR/Met Antiboy Blocks Tumor-Promoting Phenotypic Effects Induced by Resistance to EGFR Inhibition and has Potent Antitumor Activity", Oncogene, 2013, 32, 5593-5601.
Chowdary T.K. et al., "Crystal Structure of the Conserved Herpesvirus Fusion Regulator Complex gH-gL", Nat Struct Mol Biol, 2010, 17, 882-888.
Di Giovine P. et al., "Structure of Herpes Simplex Virus Glycoprotein D Bound to the Human Receptor Nectin-1", PLoS Pathogens 2011, 7,e1002277.
Douglas J.T. et al., "A System for the Propagation of Adenoviral Vectors with Genetically Modified Receptor Specificities", Nat Biotechnol, 1999, 17, 470-475.
Gallagher J.R. et al., "Functional Fluorescent Protein Insertions in Herpes Simplex Virus gB Report on gB Conformation Before and After Execution of Membrane Fusion", PLoS Pathogens, 2014, 10, e1004373.
Gatta V. et al., Abstract # P-28, 9th International Conference on Oncolytic Virus Therapeutics, Boston 2015.
Gatta V. et al., "The Engineering of a Novel Ligand in gH Confers to HSV an Expanded Tropism Independent of gD Activation by Its Receptors", PLoS Pathogens, 2015, DOI: 10.137/journal.ppat. 1004907.
Heldwein E.E. et al., "Crystal Structure of Glycoprotein B from herpes Simplex Virus 1", Science, 2006, 313, 217-220.
Hope I.A and Struhl K., "GCN4, a Eukaryotic Transciptional Activator Protein, Binds as a Dimer to Target DNA", EMBO J, 1987, 6, 2781-2784.
Josan J.S. et al., "Cell-Specific Targeting by Heterobivalent Ligands", Bioconjug Chem, 2011, 22, 1270-1278.

Karlin S. and Altschul S.F., "Methods for Assessing the Statistical Significance of Molecular Sequence Features by Using General Scoring Schemes", PNAS, 1990, 87, 2264-2268.
Karlin S. and Altschul S.F., "Applications and Statistics for Multiple High-Scoring Segments in Molecular Sequences", PNAS, 1993, 90, 5873-5877.
Li W. et al., "Identification of Functional Domains in Herpes Simplex Virus 2 Glycoprotein B", J Virol, 2006, 80, 3792-3800.
Lin E. & Spear P.G., "Random Linker-Insertion Mutagenesis to Identify Functional Domains of Herpes Simplex Virus Type 1 Glycoprotein B", PNAS, 2007, 104, 13140-13145.
Liu B.L. et al., "ICP34.5 Deleted Herpes Simplex Virus with Enhanced Oncolytic, Immune Stimulating, and Anti-Tumour Properties", Gene Ther., 2003, 10, 292-303.
Lorentzen E.U. et al., "Replication-Competent Herpes Simplex Virus Type 1 Mutant Expressing an Autofluorescent Glycoprotein H Fusion Protein", Intervirology, 2001, 44, 232-242.
Matsuura H. et al., "Crystal Structure of the Epstein-Barr Virus (EBV) Glycoprotein H/Glycoprotein L (gH/gL) Complex", PNAS, 2010, 107, 22641-22646.
Morgan A.A. and Rubenstein E., "Proline: The Distribution, Frequency, Positioning, and Common Functional Roles of Proline and Polyproline Sequences in the Human Proteome", PLoS One, 2013, 8, e53785.
Nakamura T. et al., "Rescue and Propagation of Fully Retargeted Oncolytic Measles Viruses", Nat Biotechnol, 2005, 23, 209-214.
Needleman S.B. and Wunsch C. D., "A General Method Applicable to the Search for Similarities in the Amino Acid Sequence of Two Proteins", J Mol Biol, 1970, 48, 443-453.
Pearson W.R. and Lipman D. J., "Improved Tools for Biological Sequence Comparison", PNAS, 1988, 85, 2444-2448.
Peterson R.B. and Goyal S.M., "Propagation and Quantitation of Animal Herpesviruses in Eight Cell Culture Systems", Comp Immunol Microbiol Infect Dis. 1988, 11, 93-98.
Petrovic B. et al., "Insertion of a Ligand to HER2 in gB Retargets HSV Tropism and Obviates the Need for Activaton of the Other Entry Glycoproteins", PLoS Pathogens, 2017, 13, e1006352.
Potel C. et al., "Incorporation of Green Fluorescent Protein into the Essential Envelope Glycoprotein B of Herpes Simplex Virus Type 1", J of Virological Methods, 2002, 105, 13-23.
Sandri-Goldin R.M., Alpha Herpesviruses: Molecular and Cellular Biology, Caister Academic Press, 2006.
Satoh T. et al., "PILRa is a Herpes Simplex Virus-1 Entry Co-Receptor that Associates with Glycoprotein B", Cell, 2008, 132, 935-944.
Shallal H.M. et al., "Heterobivalent Agents Targeting PSMA and Integrin-$\alpha_v\beta_3$", Bioconjug Chem, 2014, 25, 393-405.
Smith T.F. and Waterman M.S., "Comparison of Biosequences", Add APL Math, 1981, 2, 482-489.
Suenaga T. et al., "Myelin-Associated Glycoprotein Mediates Membrane Fusion and Entry of Neurotropic Herpesviruses", PNAS 2010, 107, 866-871.
Xu L. et al., "Heterobivalent Ligands Target Cell-Surface Receptor Combinations in Vivo", PNAS, 2012, 109, 21295-21300.
Zahnd C. et al., "Directed In Vitro Evolution and Crystallographic Analysis of a Peptide-Binding Single Chain Antibody Fragment (scFv) with Low Picomolar Affinity", J Biol Chem, 2004, 279, 18870-18877.
Zhou, G. et al., "Glycoprotein D or J Delivered in trans Blocks Apoptosis in SK-N-SH Cells Induced by a Herpes Simplex Virus 1 Mutant Lacking Intact Genes Expressing Both Glycoproteins", J Virol, 2000, 74, 11782-11791.
Zhou G. and Roizman B., "Characterization of a Recombinant Herpes Simplex Virus 1 Designed to Enter Cells via the IL13R$\alpha$2 Receptor of Malignant Glioma Cells", J Virol, 2005, 79, 5272-5277.

HERPESVIRUS WITH MODIFIED GLYCOPROTEIN D

CROSS-REFERENCE TO RELATED APPLICATIONS

This application is the U.S. national phase application, pursuant to 35 U.S.C. § 371, of PCT International Application Ser. No. PCT/EP2017/063498, filed Jun. 8, 2017, designating the United States and published in English, which claims the benefit of and priority to European patent Application Nos. 16173830.7, filed Jun. 9, 2016 and 17000247.1, filed Feb. 15, 2017, each of which is incorporated herein by this reference in its entirety.

BACKGROUND OF THE INVENTION

The work leading to this invention has received funding from the European Research Council under the European Union's Seventh Framework Program (FP7/2007-2013)/ERC grant agreement no 340060.

Despite a steady development in healthcare, the burden of diseases and pathologies that cannot be treated or cannot be sufficiently treated, remains elevated. Eminent among these are numerous forms of tumors, in particular metastatic forms of tumors that are treated with chemo-radio-therapy or biological medicaments, or combinations thereof, however, with limited success.

An alternative approach of tumor treatment is oncolytic virotherapy, whereby a replication competent virus infects the tumor cells, spreads from cell to cell of the tumor and destroys them.

Herpes simplex virus (HSV) is a pathogen virus for humans. In culture, it infects a large number of mammalian cells. It is an enveloped virus which enters the cell by membrane fusion, either at the plasma membrane or through endocytosis, depending on the target cell type. Entry of HSV into a target cell is a multistep process, requiring complex interactions and conformational changes of viral glycoproteins gD, gH/gL, gC and gB. These glycoproteins constitute the virus envelope which is the most external structure of the HSV particle and consists of a membrane. For cell entry, gC and gB mediate the first attachment of the HSV particle to cell surface heparan sulphate. Thereafter, a more specific interaction of the virus with the target cells occurs in that gD binds to at least two alternative cellular receptors, being nectin-1 (human: HveC) and HVEM (also known as HveA), causing conformational changes in gD that initiates a cascade of events leading to virion-cell membrane fusion. Thereby, the intermediate protein gH/gL (a heterodimer) is activated which triggers gB to catalyze membrane fusion.

Oncolytic HSVs (o-HSV) have been used in recent years as oncolytic agents. As wild-type HSV viruses are highly virulent, there is a requirement that the o-HSVs are attenuated. T-VEC/Imlygic and the viruses that have reached clinical trials carry deletion of one or more HSV genes, including the gamma $\gamma_1$34.5 gene, which encodes the ICP34.5 protein whose role is to preclude the shut off of protein synthesis in infected cells, and the UL39 gene, which encodes the large subunit of ribonucleotide reductase. In addition to some disadvantages which are shown by these viruses, such as the failure to produce high yield of progeny viruses, they furthermore have the preserved ability to bind to any cell bearing their natural receptors. Thus, the therapeutic effect of tumor cell killing is diminished and the viruses may have limitations in medical use.

One approach to overcome these limits has been genetic engineering of o-HSVs which exhibit a highly specific tropism for the tumor cells, and are otherwise not attenuated. This approach has been defined as retargeting of HSV tropism to tumor-specific receptors.

The retargeting of HSV to cancer-specific receptors entails genetic modifications of gD, such that it harbors heterologous sequences which encode a specific ligand. Upon infection with the recombinant virus, progeny viruses are formed which carry in their envelope the chimeric gD-ligand glycoprotein, in place of wildtype gD. The ligand interacts with a molecule specifically expressed on the selected cell and enables entry of the recombinant o-HSV into the selected cell. Examples of ligands that have been successfully used for retargeting of HSV are IL13α, uPaR, a single chain antibody to HER2 and a single chain antibody to EGFR.

While retargeting entails that the recombinant virus is targeted to a selected cell, retargeting does not prevent that the recombinant virus is still capable of targeting its natural cellular receptors, resulting in infection and killing of a body's cells. In order to prevent binding of a herpesvirus to its natural receptors and killing of a body's normal cells, attempts have been made to reduce the binding to natural receptors. This is termed "detargeting", which means that the recombinant herpesvirus has a reduced or no binding capability to a natural receptor of the unmodified herpesvirus, whereby the term "reduced" is used in comparison to the same herpesvirus with no such binding reducing modifications. This has the effect that normal cells are not infected or infected to a reduced extent and, thus, normal cells are not killed or less normal cells are killed. Such detargeted herpesvirus has reduced harmful activities by infecting less or not normal cells and increased beneficial activities by killing diseased cells.

While the art knows methods for retargeting of HSV to disease-specific receptors, these HSVs with the capability of being retargeted need to be propagated so that they can be produced in high amounts and are available as pharmaceuticals for treating diseases. In view of the fact that, for reasons of safety, the cells for propagation and production of the HSVs should not be diseased cells, so as to avoid the introduction of material such as DNA, RNA and/or protein of the diseased cells such as tumor cells in humans, the HSVs need to comprise additional modifications for enabling the HSVs of infecting "safe" cells which do not produce components which are harmful to humans for propagation and production of the HSVs. However, the prior art has not disclosed so far methods which enable the propagation and production of herpesviruses with the capability of being retargeted to disease-specific receptors in safe cells. Moreover, the prior art has not disclosed so far methods which enable the detargeting of HSV in addition to the retargeting of the HSV to disease-specific receptors and to safe cells for propagation and production of the herpesvirus.

There is a need in the art to provide retargeting strategies for targeting a herpesvirus to different cells which, on the one hand, are diseased cells which need to be eliminated and, on the other hand, are cells used for propagation and production of herpesviruses. Moreover, there is a need in the art that such herpesviruses are not capable of infecting a body's normal cells.

The present invention describes a recombinant HSV with a modified gD protein which retargets the virus to receptors on cells which are used for propagating and producing the recombinant herpesvirus and to cells which need to be eliminated and detargets the virus from the natural receptors of gD.

In particular, the present inventors have shown that it is possible to construct a recombinant HSV which comprises a peptide ligand of short length directed to a specific target molecule as a fusion protein with gD, whereby despite the short length of the ligand, the HSV is retargeted to cells carrying the respective target molecule. The present inventors have shown that the additional presence of a further ligand directed to a further specific target molecule in gD enables the HSV to also be retargeted to this further specific target molecule. The present inventors have shown that inactivation of binding sites of gD to the natural receptors HVEM and nectin-1 by insertion of a ligand into the HVEM binding site and/or deletion of amino acids comprised by the nectin-1 binding site results in the detargeting of the recombinant HSV from its natural receptors. The present inventors have shown that a combination of the above, namely the insertion of two ligands into gD and the deletion of a specific sequence from gD, results in a recombinant HSV which is retargeted to the target molecule(s) of the ligand(s) and detargeted from the natural receptors of gD. Thereby, it has been shown that HSV infectivity is maintained, resulting in the entry of the recombinant HSV into the cells carrying the target molecules of the ligands, namely into cells for the propagation and production of HSV and into diseased cells, whereas the infectivity of cells not carrying target molecules of the ligands, but the natural receptors of gD is abolished.

DETAILED DESCRIPTION OF THE INVENTION

Figure 1:
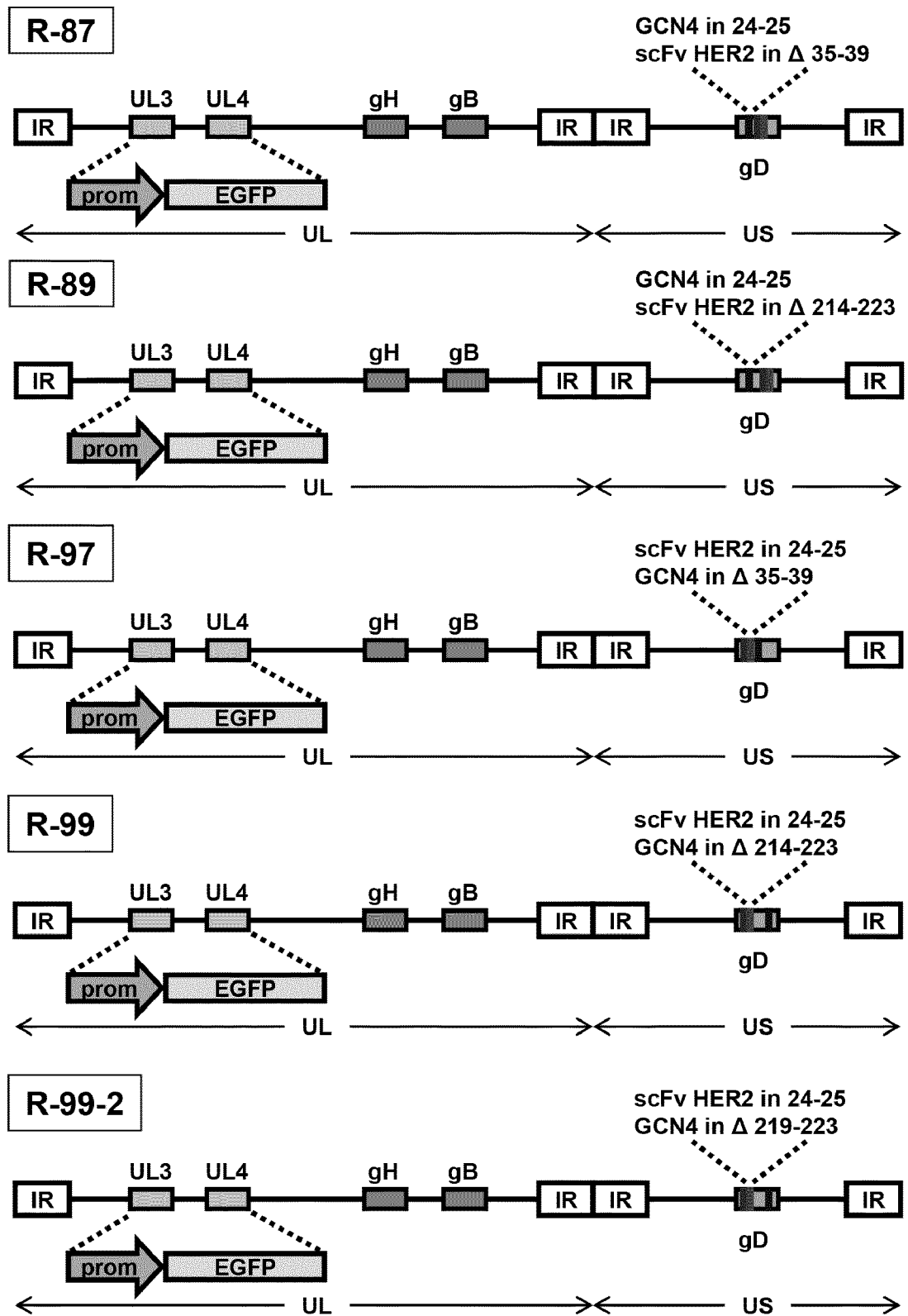

In the following, the present invention is described in detail. The features of the present invention are described in individual paragraphs. This, however, does not mean that a feature described in a paragraph stands isolated from a feature or features described in other paragraphs. Rather, a feature described in a paragraph can be combined with a feature or features described in other paragraphs.

The term "comprise/es/ing", as used herein, is meant to "include or encompass" the disclosed features and further features which are not specifically mentioned. The term "comprise/es/ing" is also meant in the sense of "consist/s/ing of" the indicated features, thus not including further features except the indicated features. Thus, the product of the present invention may be characterized by additional features in addition to the features as indicated.

In a first aspect, the present invention provides a recombinant herpesvirus comprising a heterologous peptide ligand having a length of 5 to 131 amino acids capable of binding to a target molecule fused to or inserted into glycoprotein D (gD) present in the envelope of the herpesvirus.

In an embodiment thereof, the heterologous peptide ligand has a length of 5 to 120 amino acids, preferably of 5 to 100 amino acids, more preferably of 5 to 80 amino acids, still more preferably of 5 to 60 amino acids, still more preferably of 5 to 50 amino acids, still more preferably of 5 to 45 amino acids, still more preferably of 5 to 40 amino acids, still more preferably of 5 to 35 amino acids, still more preferably of 5 to 30 amino acids, still more preferably of 10 to 30 amino acids, or still more preferably of 12 to 20 amino acids.

In an embodiment thereof, the heterologous peptide ligand comprises a part of the GCN4 yeast transcription factor, preferably an epitope of the GCN4 yeast transcription factor, more preferably the GCN4 epitope as identified by SEQ ID NO: 13, still more preferably the part of the GCN4 yeast transcription factor as comprised by SEQ ID NO: 12, most preferably the peptide is identified by SEQ ID NO: 12.

In an embodiment thereof, the heterologous peptide ligand binds to a target molecule present on a cell present in cell culture or binds to a target molecule present on a diseased cell, or the recombinant herpesvirus comprises more than one heterologous peptide ligand, wherein one of the more than one heterologous peptide ligands binds to a target molecule present on a cell present in cell culture and another of the more than one heterologous peptide ligands binds to a target molecule present on a diseased cell, preferably wherein the herpesvirus has the capability of fusing with the membrane of the cell expressing the target molecule, still more preferably of entering said cell, most preferably of killing said cell.

In an embodiment of the preceding embodiment, the cell present in cell culture is a cultured cell suitable for growth of the herpesvirus, preferably a cell line approved for herpesvirus growth, more preferably a Vero, 293, 293T, HEp-2, HeLa, BHK, or RS cell, still more preferably a Vero cell, and/or the target molecule present on the cell present in cell culture is an antibody, an antibody derivative or an antibody mimetic, preferably a single-chain antibody (scFv), more preferably an scFv capable of binding to a part of the GCN4 yeast transcription factor, still more preferably to an epitope of the GCN4 yeast transcription factor, still more preferably to the GCN4 epitope as identified by SEQ ID NO: 13, still more preferably an scFv capable of binding to the part of the GCN4 yeast transcription factor as comprised by SEQ ID NO: 12, still more preferably the scFv as comprised by SEQ ID NO: 17, or still more preferably the scFv identified by SEQ ID NO: 18. Most preferably, the cell present in cell culture is a Vero cell carrying as the target molecule the scFv identified by SEQ ID NO: 18.

In an embodiment thereof, the recombinant herpesvirus further comprises a heterologous polypeptide ligand capable of binding to a target molecule present on a diseased cell fused to or inserted into gD, preferably the herpesvirus has the capability of fusing with the membrane of the diseased cell expressing the target molecule, still more preferably of entering said cell, most preferably of killing said cell.

In an embodiment of the preceding embodiment, the recombinant herpesvirus comprises the heterologous peptide ligand which is capable of binding to a target molecule present on a cell present in cell culture and the heterologous polypeptide ligand.

In an embodiment of the preceding four paragraphs, the target molecule present on a diseased cell is present on a tumor cell, preferably the target molecule is a tumor-associated receptor, more preferably a member of the EGF receptor family, including HER2, EGFR, EGFRIII, or EGFR3 (ERBB3), EGFRvIII, or MET, FAP, PSMA, CXCR4, CEA, CEA-CAM, Ep-CAM, CADC, Mucins, Folate-binding protein, gp100, GD2, VEGF receptors 1 and 2, CD19, CD20, CD30, CD33, CD52, CD55, the integrin family, IGF1R, the Ephrin receptor family, the protein-tyrosine kinase (TK) family, RANKL, TRAILR1, TRAILR2, IL13Ralpha, UPAR, Tenascin, a member of the immune checkpoint family regulators, including PD-1, PD-L1, CTL-A4, TIM-3, LAG3, B7-H3, or IDO, tumor-associated glycoprotein 72, ganglioside GM2, A33, Lewis Y antigen, or MUC1, most preferably HER2, or the diseased cell is an infected cell, a degenerative disorder-associated cell or a senescent cell, more preferably the heterologous polypeptide ligand capable of binding to the tumor cell, infected cell, degenerative disorder-associated cell or senescent cell is an antibody, antibody derivative or antibody mimetic, still more preferably an scFv, still more preferably an scFv binding to HER2, or most preferably the scFv identified by SEQ ID NO: 16.

In an embodiment thereof, gD is so modified that the capability of the recombinant herpesvirus of interacting with receptors HVEM and/or nectin-1 is reduced, preferably substantially ablated.

In an embodiment thereof, the nectin-1 binding site of gD is inactivated, preferably a portion of gD containing amino acids 35 to 39 or a subset thereof or containing amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD is deleted from gD. More preferably, amino acids 35 to 39, amino acids 214 to 223, or amino acids 219 to 223 are deleted.

In an embodiment of the preceding embodiment, the heterologous peptide ligand is inserted into gD to inactivate the nectin-1 binding site, preferably is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD, or the heterologous polypeptide ligand is inserted into gD to inactivate the nectin-1 binding site, preferably is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD.

In an embodiment thereof, the HVEM binding site of gD is inactivated, preferably the heterologous peptide ligand or the heterologous polypeptide ligand is inserted into the HVEM binding site of gD, more preferably between amino acids 6 and 34 of gD, or still more preferably between amino acids 24 and 25 of gD, with regard to mature gD as comprised by SEQ ID NO: 1 or corresponding amino acids of a homologous gD.

In an embodiment of the preceding embodiment, the heterologous peptide ligand is inserted into the HVEM binding site of gD, preferably between amino acids 6 and 34 of gD, more preferably between amino acids 24 and 25, with regard to mature gD as comprised by SEQ ID NO: 1 or corresponding amino acids of a homologous gD, and the heterologous polypeptide ligand is inserted into gD to inactivate the nectin-1 binding site, preferably is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD, or the heterologous polypeptide ligand is inserted into the HVEM binding site of gD, preferably between amino acids 6 and 34, more preferably between amino acids 24 and 25, with regard to mature gD as comprised by SEQ ID NO: 1 or corresponding amino acids of a homologous gD, and the heterologous peptide ligand is inserted into gD to inactivate the nectin-1 binding site, preferably is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD. Preferably, the heterologous peptide ligand is inserted between amino acids 24 and 25 with regard to mature gD as comprised by SEQ ID NO: 1 or within corresponding amino acids of a homologous gD and the heterologous polypeptide ligand is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD, or the heterologous polypeptide ligand is inserted between amino acids 24 and 25 of gD with regard to mature gD as comprised by SEQ ID NO: 1 or within corresponding amino acids of a homologous gD and the heterologous peptide ligand is inserted into gD instead of amino acids 35 to 39 or a subset thereof or instead of amino acids 214 to 223 or a subset thereof, such as amino acids 215 to 223, 216 to 223, 217 to 223, 218 to 223, or 219 to 223, with regard to mature gD as comprised by SEQ ID NO: 1 or corresponding amino acids of a homologous gD. More preferably, the heterologous peptide ligand identified by SEQ ID NO: 12 is inserted between amino acids 24 and 25 with regard to mature gD as comprised by SEQ ID NO: 1 or within corresponding amino acids of a homologous gD and the heterologous polypeptide ligand identified by SEQ ID NO: 16 is inserted into gD instead of amino acids 35 to 39 or instead of amino acids 214 to 223 or instead of amino acids 219 to 223 with regard to mature gD as comprised by SEQ ID NO: 1 or corresponding amino acids of a homologous gD, or the heterologous polypeptide ligand identified by SEQ ID NO: 16 is inserted between amino acids 24 and 25 of gD with regard to mature gD as comprised by SEQ ID NO: 1 or within corresponding amino acids of a homologous gD and the heterologous peptide ligand identified by SEQ ID NO: 12 is inserted into gD instead of amino acids 35 to 39 or instead of amino acids 214 to 223 or instead of amino acids 219 to 223 with regard to mature gD as comprised by SEQ ID NO: 1 or corresponding amino acids of a homologous gD.

"In an embodiment thereof", as used in the above paragraphs, means back-reference to each of the preceding paragraphs entitled "In a first aspect" or "In an embodiment thereof".

The recombinant herpesvirus of the present invention serves the purpose of infecting and killing diseased cells in humans. This requires the provision of the herpesvirus and, therefore, its propagation and production. As propagation of the herpesvirus shall be avoided in diseased cells, so as to avoid the introduction of material such as DNA, RNA and/or protein of the diseased cells such as tumor cells into humans, the recombinant herpesvirus has to be engineered to be capable of infecting cells which are useful for the production of the herpesvirus and do not produce material which may be harmful to humans. Such cells are also referred to herein as "safe" cells. This requires the retargeting of the recombinant herpesvirus of the present invention to such cells for propagation and production. To achieve this, glycoprotein D of the recombinant herpesvirus of the present invention is modified to include a heterologous peptide ligand, fused to or inserted into gD. The peptide allows, despite its short length, for binding to a target molecule which is accessible on the surface of a cell which can be safely used for the production of the herpesvirus. The use of the peptide for binding to a target molecule requires the accessibility of such target molecule on a cell which can be safely used for propagating and producing the recombinant herpesvirus. This in turn may require the modification of cells which are capable of safely producing the recombinant herpesvirus of the present invention to comprise target molecules capable of binding to the peptide. Such a mutually dependent production of ligand and target molecule may result in the generation of highly effective ligand/target molecule pairs allowing efficient retargeting of the recombinant herpesvirus of the present invention to cells for producing the virus.

In an embodiment of the invention, in order to be useful in the elimination of diseased cells, the recombinant herpesvirus of the present invention may, in addition to the heterologous peptide ligand retargeting the herpesvirus to cells useful for propagation and production, comprise a further ligand retargeting the herpesvirus to diseased cells fused to or inserted into gD. Consequently, the recombinant herpesvirus of the present invention may comprise a heterologous peptide ligand retargeting the herpesvirus to cells useful for propagation and production and a heterologous peptide ligand or a heterologous polypeptide ligand retargeting the herpesvirus to diseased cells, the ligands fused to or inserted into gD.

In order that the recombinant herpesvirus of the present invention is efficiently retargeted to a cell present in cell culture and possibly to a diseased cell, it is advantageous that the binding sites of the recombinant herpesvirus to natural receptors of gD present on cells are inactivated. This allows the efficient targeting to cells which are intended to be infected whereas infection of normal cells which are naturally infected by herpesvirus is reduced. gD is essential for virus entry into host cells and plays an essential role in herpesvirus infectivity. The inactivation of binding sites of gD to their natural receptors favors the retargeting to cells carrying the target molecules of the ligand(s). Thus, in embodiments of the present invention, the natural HVEM and/or nectin-1 binding site(s) of gD are inactivated such that the binding thereto and, therefore, to cells carrying these receptors is reduced. The present inventors found new regions within the nectin-1 binding site, the deletion of which, in combination with the inactivation of the HVEM binding site, results in efficient detargeting of the recombinant herpesvirus from the natural receptors of gD, and, therefore, in the detargeting of the recombinant herpesvirus of the present invention from normal cells. The combination of the inactivation of the binding site to HVEM by insertion of a ligand between amino acids 24 and 25 with respect to mature gD as comprised by of SEQ ID NO: 1, with the inactivation of the binding site to nectin-1 by insertion of a ligand instead of deleted amino acids 35 to 39 or a subset thereof or instead of deleted amino acids 214 to 223 or a subset thereof, such as amino acids 215 to 223, 216 to 223, 217 to 223, 218 to 223, or 219 to 223, with respect to mature gD as comprised by of SEQ ID NO: 1, being a preferred embodiment of the present invention, results in a recombinant herpesvirus which is very efficiently retargeted to cells carrying the target molecules of the ligands and detargeted from the natural receptors of gD.

More generally, detargeting the recombinant herpesvirus of the present invention from a natural receptor of gD may be obtained by inactivation of the HVEM binding site of gD, such as the inactivation of the HVEM binding site by insertion of a ligand between amino acids 6 and 34, such as between amino acids 24 to 25. Detargeting the recombinant herpesvirus of the present invention from a natural receptor of gD may be obtained by inactivation of the nectin-1 binding site of gD, such as the inactivation of the nectin-1 binding site by deletion of amino acids 35 to 39 or a subset thereof or amino acids 214 to 223 or a subset thereof, such as amino acids 215 to 223, 216 to 223, 217 to 223, 218 to 223, or 219 to 223, such as the insertion of a ligand instead of amino acids 35 to 39 or a subset thereof or amino acids 214 to 223 or a subset thereof, such as amino acids 215 to 223, 216 to 223, 217 to 223, 218 to 223, or 219 to 223. Detargeting the recombinant herpesvirus of the present invention from a natural receptor of gD may be obtained by inactivation of the HVEM binding site and of the nectin-1 binding site of gD, such as the inactivation of the HVEM binding site by insertion of a ligand between amino acids 24 to 25 and of the nectin-1 binding site by deletion of amino acids 35 to 39 or a subset thereof or 214 to 223 or a subset thereof, such as amino acids 215 to 223, 216 to 223, 217 to 223, 218 to 223, or 219 to 223. Detargeting the recombinant herpesvirus of the present invention from a natural receptor of gD may be obtained by inactivation of the HVEM binding site by insertion of a ligand between amino acids 24 to 25 and of the nectin-1 binding site by insertion of a ligand instead of amino acids 35 to 39 or a subset thereof or amino acids 214 to 223 or a subset thereof, such as amino acids 215 to 223, 216 to 223, 217 to 223, 218 to 223, or 219 to 223. The amino acid numbers refer to mature gD as comprised by SEQ ID NO: 1 or corresponding amino acids of a homologous gD.

Thus, in the present invention the retargeting of a recombinant herpesvirus to target molecules of one or more ligands may be efficiently combined with the detargeting of the recombinant herpesvirus from the natural receptors of gD, resulting in a recombinant herpesvirus which efficiently infects and kills cells useful for propagation and production and diseased cells.

As an alternative to the above, the heterologous peptide ligand is capable of binding to a target molecule present on a diseased cell. In a possible combination with a heterologous polypeptide ligand which is defined herein to be capable of binding to a target molecule present on a diseased cell, both ligands may be useful to target the recombinant herpesvirus to one or more binding site(s) on one or more target molecule(s) present on same or different diseased cells.

Apart from the above, a herpesvirus may, in a very general manner, comprise at least two ligands, such as 2, 3, or 4 ligands, preferably 2 ligands, fused to or inserted into gD. The target cells comprise those useful for propagation and production, or the target cells comprise those useful for propagation and production and those that are diseased cells, or the target cells comprise those that are diseased cells. Herpesvirus, ligand, gD and cell are as defined herein.

Apart from the above, a herpesvirus may, in a very general manner, comprise at least two ligands, such as 2, 3, or 4 ligands, preferably 2 ligands, wherein one ligand is inserted into the HVEM binding site. Preferably, a herpesvirus may, in a very general manner, comprise at least two ligands such as 2, 3, or 4 ligands, preferably 2 ligands, wherein one ligand is inserted between amino acids 6 and 34, preferably amino acids 24 to 25, with respect to mature gD as comprised by SEQ ID NO: 1 or corresponding amino acids of a homologous gD. The target cells comprise those useful for propagation and production, or the target cells comprise those useful for propagation and production and those that are diseased cells, or the target cells comprise those that are diseased cells. Herpesvirus, ligand, gD and cell are as defined herein.

Apart from the above, a herpesvirus may, in a very general manner, comprise a deletion of amino acids 35 to 39 or a subset thereof or of amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD. Herpesvirus and gD are as defined herein.

Apart from the above, a herpesvirus may, in a very general manner, comprise a deletion of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD and an insertion of a ligand into the HVEM binding site, preferably between amino acids 6 and 34, more preferably amino acids 24 to 25, with respect to mature gD as comprised by SEQ ID NO: 1 or corresponding amino acids of a homologous gD. Herpesvirus, ligand, and gD are as defined herein.

Apart from the above, a herpesvirus may, in a very general manner, comprise a deletion of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD and an insertion of a ligand instead of the deleted amino acids. Herpesvirus, ligand, and gD are as defined herein.

Apart from the above, a herpesvirus may, in a very general manner, comprise a deletion of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD, and an insertion of a ligand into the HVEM binding site, and an insertion of a ligand instead of the deleted amino acids. Herpesvirus, ligand, and gD are as defined herein.

Apart from the above, a herpesvirus may, in a very general manner, comprise a deletion of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD, and an insertion of a ligand between amino acids 24 to 25 with respect to mature gD as comprised by SEQ ID NO: 1 or corresponding amino acids of a homologous gD, and an insertion of a ligand instead of the deleted amino acids. Herpesvirus, ligand, and gD are as defined herein.

Glycoprotein D (gD) is a 55 kDa virion envelope glycoprotein which is essential for herpes simplex virus entry into host cells and plays an essential role in herpesvirus infectivity. Upon entry of herpes simplex virus into a cell, the interaction of gD with the heterodimer gH/gL is the critical event in an activation cascade involving the four glycoproteins gD, gH, gL, and gB, which are involved in herpesvirus entry into a cell. The activation cascade starts with the binding of gD to one of its receptors, nectin-1, HVEM, and modified heparan sulfates, is transmitted to gH/gL, and finally to gB. gB carries out the fusion of the herpesvirus with the target cell membrane. The heterodimer gH/gL interacts with the profusion domain of gD which profusion domain is dislodged upon interaction of gD with one of its receptors during cell entry. gD comprises some specific regions which are responsible for the herpesvirus to be targeted to its natural receptors. These are the HVEM-1 binding site being located between amino acids 7 to 32 and the nectin-1 binding site which is more widespread and discontinuous and includes critical residues located mainly in three regions, between amino acids 36 and 39, 132-134, and 213 to 223, with respect to mature gD as comprised by SEQ ID NO: 1. The nucleotide and amino acid sequences of a variety of gDs of different herpes simplex virus-1 and herpes simplex virus-2 strains, and clinical isolates, as well as of animal orthologs are known in the art. For illustrative purposes only, without being limited thereto, reference is made to the amino acid sequence of gD of human herpesvirus 1 disclosed herein as SEQ ID NO: 1. The corresponding nucleotide sequence and the amino acid sequence of precursor gD are available from the NCBI (National Centre for Biotechnology Information; National Library of Medicine, Bethesda, Md. 20894, USA; www.ncbi.nlm.nih.gov) under the GenBank accession ID: GU734771.1; coordinates from positions 138281 to 139465.

```
                                             SEQ ID NO: 1
MGGAAARLGA VILFVVIVGL HGVRGKYALA DASLKMADPN

RFRGKDLPVL DQLTDPPGVR RVYHIQAGLP DPFQPPSLPI

TVYYAVLERA CRSVLLNAPS EAPQIVRGAS EDVRKQPYNL

TIAWFRMGGN CAIPITVMEY TECSYNKSLG ACPIRTQPRW

NYYDSFSAVS EDNLGFLMHA PAFETAGTYL RLVKINDWTE

ITQFILEHRA KGSCKYALPL RIPPSACLSP QAYQQGVTVD

SIGMLPRFIP ENQRTVAVYS LKIAGWHGPK APYTSTLLPP

ELSETPNATQ PELAPEDPED SALLEDPVGT VAPQIPPNWH

IPSIQDAATP YHPPATPNNM GLIAGAVGGS LLAALVICGI

VYWMRRRTQK APKRIRLPHI REDDQPSSHQ PLFY
``` gD homologs are found in some members of the alpha subfamily of Herpesviridae. Therefore, the term "glycoprotein D", as referred to herein, refers to any gD homolog found in the gD-encoding members of Herpesviridae. Alternatively, gD, as referred to herein, refers to any gD which has an amino acid identity to the sequence of SEQ ID NO: 1 of at least 70%, 80%, 85%, 90%, 95%, 96%, 97%, 98%, 99% or 100%. Alternatively, the gD, as referred to herein, refers to any gD which has an amino acid homology to SEQ ID NO: 1 of at least 50%, 60%, 70%, 80%, 85%, 90%, 95%, or 100%. The gD, as referred to herein, also includes a fragment of gD. Preferably, gD, as referred to herein, including any gD found in Herpesviridae, any gD having an amino acid identity to the sequence of SEQ ID NO: 1, as defined above, and any fragment of a gD, has the same activity of the gD according to SEQ ID NO: 1. More preferably, during the entry process of the virus into a cell, gD binds to one of its receptors, thereby still more preferably interacting with the gH/gL heterodimer, which still more preferably results in dislodging the profusion domain of gD.

The percentage of "sequence identity," as used herein, refers to the percentage of amino acid residues which are identical in corresponding positions in two optimally aligned sequences. It is determined by comparing two optimally aligned sequences over a comparison window, where the fragment of the amino acid sequence in the comparison window may comprise additions or deletions (e.g., gaps or overhangs) as compared to the reference sequence, SEQ ID NO: 1 (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman, 1981, by the homology alignment algorithm of Needleman and Wunsch, 1970, by the search for similarity method of Pearson and Lipman, 1988, by the algorithm of Karlin and Altschul, 1990, modified by Karlin and Altschul, 1993, or by computerized implementations of these algorithms (GAP, BEST-FIT, BLAST, PASTA, and TFASTA in the Wisconsin Genetics Software Package, Genetics Computer Group (GCG), 575 Science Dr., Madison, Wis.), or by inspection. GAP and BESTFIT are preferably employed to determine the optimal alignment. Typically, the default values of 5.00 for gap weight and 0.30 for gap weight length are used.

The "percentage of homology", as used herein, refers to the percentage of amino acid residues which are homologous in corresponding positions in two optimally aligned sequences. The "percentage of homology" between two sequences is established in a manner substantially identical to what has been described above with reference to the determination of the "percentage of identity" except for the fact that in the calculation also homologous positions and not only identical positions are considered. Two homologous amino acids have two identical or homologous amino acids. Homologous amino acid residues have similar chemical-physical properties, for example, amino acids belonging to a same group: aromatic (Phe, Trp, Tyr), acid (Glu, Asp), polar (Gln, Asn), basic (Lys, Arg, His), aliphatic (Ala, Leu, lie, Val), with a hydroxyl group (Ser, Thr), or with a short lateral chain (Gly, Ala, Ser, Thr, Met). It is expected that substitutions between such homologous amino acids do not change a protein phenotype (conservative substitutions).

A gD is "homologous" or a "homolog" if it has an identity to SEQ ID NO: 1 of at least 70%, 80%, 85%, 90%, 95%, 96%, 97%, 98%, 99%, or 100%, if it has an amino acid homology to SEQ ID NO: 1 of at least 50%, 60%, 70%, 80%, 85%, 90%, 95%, or 100%, or if it has the same activity as the gD according to SEQ ID NO: 1. Preferably, "same activity" may be understood in the sense that gD binds to a cellular receptor, and more preferably, during the entry process of the virus into a cell, gD interacts with the gH/gL heterodimer which still more preferably results in dislodging of the profusion domain of gD. A homolog may also be a fragment of a full length gD having the activity as indicated above.

A corresponding region of a homologous gD is a region of a gD which aligns with a given region of the gD according to SEQ ID NO: 1 when using the Smith-Waterman algorithm and the following alignment parameters: MATRIX: BLOSUM62, GAP OPEN: 10, GAP EXTEND: 0.5. This algorithm is generally known and used in the art if performing pairwise sequence comparisons and the skilled person knows how to apply it. In case only a part or parts of the given region of SEQ ID NO: 1 aligns with the sequence of a homologous gD using above algorithm and parameters, the term "corresponding region" refers to the region which aligns with the part(s) of the given region of SEQ ID NO: 1. In this case, the region in the homologous gD, in which the ligand is inserted, comprises only the amino acids which align with the part(s) of the given region of SEQ ID NO: 1. The term "corresponding region" may also refer to a region which is flanked by corresponding flanking sequences, wherein the flanking sequences align, using above algorithm and parameters, with sequences flanking the region of SEQ ID NO: 1. These flanking sequences are at least 5, 6, 7, 8, 9, 10, 15, 20, 30, 40 or 50 amino acids long. Other algorithms which may be used are the algorithms of Needleman and Wunsch, 1970, the similarity method of Pearson and Lipman, 1988, or the algorithm of Karlin and Altschul, 1990, modified by Karlin and Altschul, 1993, or computerized implementations of these algorithms. The term "corresponding amino acid" refers to an amino acid which is present within a corresponding region and which is the counterpart of a given amino acid of SEQ ID NO: 1 in the alignment. A corresponding amino acid must not be identical to its counterpart in SEQ ID NO: 1 in the alignment, as far as it is present within a corresponding region.

The term "chimeric glycoprotein D" or "chimeric gD", as used herein, means a gD having fused to or inserted into the gD (a) ligand(s). The chimeric gD is encoded by the recombinant virus, is synthesized within the cell that produces the recombinant virus, and becomes incorporated in the envelope of the virion. Methods to produce the recombinant virus by genetic engineering are known in the art, exemplified, but not limited to BAC technologies. Methods for producing chimeric glycoprotein D are known in the art.

The chimeric gD of the present invention, as exemplified by SEQ ID NOS: 2 to 11, carries a heterologous peptide ligand and possibly a heterologous polypeptide ligand and thereby confers a new activity on the virus, in addition to the activity that the gD portion carries out for the wildtype (wt) virus. The chimeric gD, once it is part of the envelope of the recombinant virus, enables the binding of the recombinant virus to the target molecule(s) of the ligand(s), and retargets the tropism of the recombinant virus to (a) cell(s) carrying the target molecule(s) of the ligand(s). Preferably, upon binding to the target molecule(s) of the ligand(s), the chimeric gD interacts with the gH/gL heterodimer and still more preferably the profusion domain of gD is dislodged, which still more preferably results in the entry of the recombinant herpesvirus into the cell via the target molecule of the ligand. After fusion with a cell carrying the target molecule of the ligand, the recombinant herpesvirus enters the cell, and the cell infected by the recombinant herpesvirus produces proteins encoded by the viral genome, including the chimeric gD harboring the heterologous peptide ligand (s). The infected cell produces progeny virus which lyses the cell, thereby killing it.

Depending on the site of insertion of the ligand(s) into gD, the targeting property of the recombinant herpesvirus to the natural receptor(s) may be maintained, and gD may maintain its activity to bind to its natural receptor(s) and to mediate cell entry via the natural receptor(s). However, it is preferred that the ligand(s) are inserted into gD at sites such that the binding capability of gD to its natural receptor(s) is reduced.

The indication of a specific amino acid number or region of gD, as used herein, refers to the "mature" form of gD, as comprised by SEQ ID NO: 1, wherein SEQ ID NO: 1 includes the N-terminal signal sequence comprising the first 25 amino acids. The "mature" form of gD starts with amino acid 26 of SEQ ID NO: 1, corresponding to amino acid 1 of mature gD, and extends until amino acid 394, corresponding to amino acid 369 of mature gD. As gD glycoproteins with amino acid sequences different from SEQ ID NO: 1 are also comprised by the present invention, the indication of a specific amino acid number or of a specific amino acid region which relates to mature gD as comprised by SEQ ID NO: 1 means also the amino acid number or region of a homologous gD, which corresponds to the respective amino acid number or region of mature gD as comprised by SEQ ID NO: 1. The amino acids numbers 6 to 34; 24 to 25; 35 to 39; 214 to 223, or 219 to 223 referring to mature gD and as used herein, correspond to the amino acid numbers 31 to 59;

49 to 50; 60 to 64; 239 to 248, or 244 to 248, respectively, of precursor gD of SEQ ID NO: 1. The term "mature gD as comprised by SEQ ID NO: 1" refers to amino acids 26 to 394 of SEQ ID NO: 1, corresponding to amino acids 1 to 369 of mature gD.

The term "retargeting", as used herein, means that the recombinant herpesvirus of the present invention is targeted to the target molecule which is bound by the ligand(s) introduced into the herpesvirus. However, the recombinant herpesvirus is still capable of being targeted to the natural receptors of gD. Retargeting is different from "detargeting", which means that the recombinant herpesvirus is no longer capable of being targeted to a natural receptor of gD.

The term "recombinant" herpesvirus, as referred to herein, refers to a herpesvirus that has been genetically engineered by genetic recombination to include additional nucleic acid sequences which encode the heterologous peptide(s) or polypeptide. Methods of producing recombinant herpesviruses are well known in the art (see for example Sandri-Goldin et al., 2006). However, the present invention is not limited to genetic engineering methods. Also other methods may be used for producing an herpesvirus having fused or inserted a heterologous polypeptide ligand to or into gD, respectively.

The term "herpesvirus", as referred to herein, refers to a member of the Herpesviridae family of double-stranded DNA viruses, which cause latent or lytic infections. Herpesviruses all share a common structure in that their genomes consist of relatively large (about from 100.000 to 200.000 base pairs), double-stranded, linear DNA encoding 80 to 200 genes, encased within an icosahedral protein cage called the capsid which is itself wrapped by a protein layer called the tegument containing both viral proteins and viral mRNAs and a lipid bilayer membrane called the envelope. This whole particle is also known as a virion. The term "herpesvirus" also refers to members of the Herpesviridae family which are mutated comprising one or more mutated genes, such as, e.g., herpesviruses which were modified in a laboratory.

In a preferred embodiment, the herpesvirus is selected from the group consisting of Herpes Simplex Virus 1 (HSV-1), Herpes Simplex Virus 2 (HSV-2), swine alpha-herpesvirus Pseudorabievirus (PRV), Chimpanzee alpha1 herpesvirus (ChHV), Papiine herpesvirus 2 (HVP2), Cercopithecine herpesvirus 1 (CeHV1), Cercopithecine herpesvirus 2 (CeHV2), Macacine herpesvirus 1 (MHV1), Saimiriine herpesvirus 1 (HVS1), Bovine herpesvirus 1 (BoHV-1), Bovine Herpesvirus 5 (BoHV-5), Equine herpesvirus 1 (EHV-1), Canine herpesvirus 1 (CHV), Feline herpesvirus 1 (FHV-1), Duck enteritis virus (DEV), Fruit bat alphaherpesvirus 1 (FBAHV1), Bovine herpesvirus 2 (BoHV-2), Leporid herpesvirus 4 (LHV-4), Equine herpesvirus 3 (EHV-3), Equine herpesvirus 4 (EHV-4), Equine herpesvirus 8 (EHV-8), Equine herpesvirus 9 (EHV-9), Suid herpesvirus 1 (SuHV-1), Marek's disease virus serotype 2 (MDV2), Falconid herpesvirus type 1 (FaHV-1), Gallid herpesvirus 3 (GaHV-3), Gallid herpesvirus 2 (GaHV-2), Gallid herpesvirus 1 (GaHV-1), Psittacid herpesvirus 1 (PsHV-1), or Meleagrid herpesvirus 1 (MeHV-1). In a more preferred embodiment, the herpesvirus is HSV-1 or HSV-2, most preferably HSV-1.

The term "heterologous", as used herein, refers to a peptide or polypeptide that is not encoded by the herpesvirus genome, or that of any other herpesvirus. Preferably, the term "heterologous" refers to a peptide ligand or polypeptide ligand which binds to a cell which carries a target molecule of the ligand and is to be infected by the recombinant herpesvirus of the present invention.

The term "peptide" or "polypeptide", as used herein, is a continuous and unbranched peptide chain consisting of amino acids connected by peptide bonds. The term "peptide", as used herein, is a short chain, consisting of 5 to 131 amino acids, preferably 5 to 120 amino acids, more preferably 5 to 100 amino acids, still more preferably 5 to 80 amino acids, still more preferably 5 to 60 amino acids, still more preferably 5 to 50 amino acids, still more preferably 5 to 45 amino acids, still more preferably 5 to 40 amino acids, still more preferably 5 to 35 amino acids, still more preferably 5 to 30 amino acids, still more preferably 10 to 30 amino acids such as 11, 12, 13, 14, 15, 16, 17, 18, 19, 20, 21, 22, 23, 24, 25, 26, 27, 28, or 29 amino acids, or still more preferably of 12 to 20 amino acids. The minimum length is 5 amino acid residues. Alternatively, the minimum length is the length of an epitope or of a binding region of a polypeptide to a receptor. The term "polypeptide" refers in general to any polypeptide consisting of amino acids connected by peptide bonds. The polypeptide is not restricted with respect to its length, whereby the length may range from some amino acids such as 5 amino acids or the length of an epitope or binding region to a receptor to some hundreds or thousands of amino acids, as long as a molecule or an assembly of molecules is formed which is capable, as far as a ligand is meant, of binding to a target molecule or, as far as a target molecule is meant, of binding to a ligand. In the present invention, a polypeptide may be used as a ligand or as a target molecule. More than one polypeptide chain may assemble to a complex such as an antibody. The term "polypeptide", as used herein, also comprises an assembly of polypeptide chains. The difference between "peptide" and "polypeptide" is that a peptide has a short length, as indicated above, and consists of a single peptide chain, whereas a polypeptide may be of any length, may consist of a single polypeptide chain or may form an assembly of polypeptide chains.

A ligand, as referred to herein, binds or is capable of binding to a target molecule accessible on the surface of a cell. Preferably, it specifically binds or is capable of specifically binding to a target molecule accessible on the surface of a cell, whereby the term "specifically binds" refers to a binding reaction wherein the ligand binds to a particular target molecule of interest, whereas it does not bind or not bind in a substantial amount (less than 10%, 5%, 3%, 2%, 1%, or 0.5%) to other molecules present on cells or to other molecules to which the ligand may come in contact in an organism. Generally, a ligand that "specifically binds" a target molecule may have an equilibrium affinity constant greater than about $10^5$ (e.g., $10^6$, $10^7$, $10^8$, $10^9$, $10^{19}$, $10^{11}$, $10^{12}$ or more) mole/liter for that target molecule. Preferably, the ligand mediates the capability that the virus fuses with the cell, so that more preferably the virus then enters the cell, and still more preferably kills the cell. It is understood that the ligand is not harmful to humans. Moreover, the ligand is not a herpesvirus protein or is not derived by modification from a herpesvirus protein. The term "ligand", as referred to herein, refers to the heterologous peptide ligand having a length of 5 to 131 amino acids as well as to the heterologous polypeptide ligand.

The present invention is characterized by the fact that the recombinant herpesvirus comprises a heterologous peptide ligand which may be capable of binding to a target molecule present on a cell present in cell culture or to a target molecule present on a diseased cell. The peptide ligand may be a natural polypeptide which is capable of specifically binding to a target molecule which is accessible on a cell, as long as it does not exceed a length of 131 amino acids. The ligand may be the natural ligand of a natural target molecule such as a receptor molecule, which is accessible on a cell. The ligand may be a natural polypeptide which has been selected to bind to an artificial target molecule, whereby the target molecule is designed to be capable of binding to the ligand. The natural polypeptide may be derived from any organism, preferably from an organism which is not harmful to human. For example, the natural polypeptide is a fungal or bacterial polypeptide, such as a polypeptide from the genus *Saccharomyces* such as *Saccharomyces cerevisiae*. The peptide ligand may be an artificial polypeptide which is capable of specifically binding to a target molecule. Artificial polypeptide ligands have non-naturally occurring amino acid sequences that function to bind a particular target molecule. The sequence of the artificial polypeptide ligand may be derived from a natural polypeptide which is modified, including insertion, deletion, replacement and/or addition of amino acids, whereby the binding capability of the corresponding natural polypeptide is retained. For example, the ligand may be a part of a natural polypeptide, as referred to above, as far as said part is capable of binding to the target molecule to which the corresponding full-length polypeptide binds. Alternatively, the natural polypeptide has been modified to comprise an amino acid identity to the corresponding natural polypeptide of at least 70%, 80%, 85%, 90%, 95%, 96%, 97%, 98% or 99%, whereby the modified polypeptide retains the activity of the corresponding natural polypeptide, such as binding to the target molecule. Still alternatively, the polypeptide is an antibody derivative or an antibody mimetic that binds to the target molecule. The antibody derivative or antibody mimetic may be mono-specific (i.e. specific to one target molecule accessible on the surface of a cell) or multi-specific (i.e. specific to more than one target molecule accessible on the surface of the same or a different cell), for example bi-specific or tri-specific (e.g., Castoldi et al., 2013, Castoldi et al., 2012). The preferred peptide ligand of the present invention is a part of the GCN4 yeast transcription factor, more preferably the part of the GCN4 yeast transcription factor as comprised by SEQ ID NO: 12, most preferably the sequence of SEQ ID NO: 12 (GCN4 peptide), which is capable of binding to an artificial target molecule designed to be capable of binding to the ligand. Said artificial target molecule is present on a cell present in cell culture and is used for propagation and production of the virus.

The GCN4 yeast transcription factor is state of the art (see e.g. Arndt and Fin, 1986; Hope and Struhl, 1987). An exemplary GCN4 yeast transcription factor is one identified by SEQ ID NO: 14 (UniProtKB—P03069) encoded by the gene identified in SEQ ID NO: 15 (GenBank accession No. AJ585687.1). The term "GCN4 yeast transcription factor", as referred to herein, refers to any GCN4 yeast transcription factor present in nature. Alternatively, GCN4 yeast transcription factor, as referred to herein, refers to any GCN4 yeast transcription factor which has an amino acid identity to the sequence of SEQ ID NO: 14 of at least 70%, 80%, 85%, 90%, 95%, 96%, 97%, 98%, 99% or 100%. Alternatively, the GCN4 yeast transcription factor, as referred to herein, refers to any GCN4 yeast transcription factor which has an amino acid homology to SEQ ID NO: 14 of at least 50%, 60%, 70%, 80%, 85%, 90%, 95%, or 100%. A GCN4 yeast transcription factor is "homologous" or a "homolog" if it has an identity to SEQ ID NO: 14 of at least 70%, 80%, 85%, 90%, 95%, 96%, 97%, 98%, 99%, or 100%, if it has an amino acid homology to SEQ ID NO: 14 of at least 50%, 60%, 70%, 80%, 85%, 90%, 95%, or 100%, or if it has the same activity as the GCN4 yeast transcription factor according to SEQ ID NO: 14. Preferably, "same activity" may be understood in the sense that GCN4 yeast transcription factor works as a transcription factor in the same way as the GCN4 yeast transcription factor according to SEQ ID NO: 14. The term "a part thereof", as used herein, comprises any part of the GCN4 yeast transcription factor against which a target molecule can be generated to which the "part thereof" is capable of binding. The length of "the part thereof" is such that a peptide length of 5 to 131 amino acids, preferably 5 to 120 amino acids, more preferably 5 to 100 amino acids, still more preferably 5 to 80 amino acids, still more preferably 5 to 60 amino acids, still more preferably 5 to 50 amino acids, still more preferably 5 to 45 amino acids, still more preferably 5 to 40 amino acids, still more preferably 5 to 35 amino acids, still more preferably 5 to 30 amino acids, still more preferably 10 to 30 amino acids such as 11, 12, 13, 14, 15, 16, 17, 18, 19, 20, 21, 22, 23, 24, 25, 26, 27, 28, or 29 amino acids, or still more preferably of 12 to 20 amino acids results, whereby the peptide may include additional amino acids such as linker sequences. Most preferably, the length of the "the part thereof" is 12 amino acids. The most preferred "part thereof" is the epitope YHLENEVARLKK (SEQ ID NO: 13) of GCN4 yeast transcription factor (GCN4 epitope). The epitope YHLENEVARLKK consists of 12 amino acids which are recognized by the scFv identified by SEQ ID NO: 18. For fusion to or insertion into gD, the epitope YHLENEVARLKK (SEQ ID NO: 18) may further comprise two flanking wt (wildtype) GCN4 residues on each side and one (for fusion) or two (for insertion) GS linkers. This construct including two GS linkers is herein named GCN4 peptide (SEQ ID NO: 12). This 20 amino acid peptide confers to the herpesvirus the ability to infect and replicate in a cell line bearing a target molecule to which the "part thereof" binds.

The present invention is furthermore characterized by the fact that the recombinant herpesvirus optionally comprises a heterologous polypeptide ligand which is capable of binding to a target molecule present on a diseased cell. The polypeptide ligand may be a natural polypeptide which is capable of specifically binding to a target molecule which is accessible on a diseased cell. The polypeptide ligand may be a natural ligand that is capable of binding to a natural target molecule such as a receptor molecule, which is accessible on a diseased cell. Examples of such a ligand may be a cytokine, a chemokine, urokinase plasminogen activator (UPa), an immune checkpoint blocker, or a growth factor. Known examples are EGF and IL13. Alternatively, the ligand is an antibody that binds to a target molecule. The natural polypeptide may be derived from any organism, preferably from an organism which is not harmful to human. The polypeptide ligand may be an artificial polypeptide which is capable of specifically binding to a target molecule which is accessible on a diseased cell. The sequence of the artificial polypeptide ligand may be derived from a natural polypeptide which is modified, including insertion, deletion, replacement and/or addition of amino acids, whereby the binding capability of the corresponding natural polypeptide is retained. For example, the ligand may be a part of a natural polypeptide, as referred to above, as far as said part is capable of binding to the target molecule to which the corresponding full-length polypeptide binds. Alternatively, the natural polypeptide has been modified to comprise an amino acid identity to the corresponding natural polypeptide of at least 70%, 80%, 85%, 90%, 95%, 96%, 97%, 98% or 99%, whereby the modified polypeptide retains the activity of the corresponding natural polypeptide, such as binding to the target molecule. Still alternatively, the polypeptide is an antibody derivative or an antibody mimetic that binds to the target molecule. The antibody, antibody derivative or antibody mimetic may be mono-specific (i.e. specific to one target molecule accessible on the surface of a cell) or multi-specific (i.e. specific to more than one target molecule accessible on the surface of the same or a different cell), for example bi-specific or tri-specific (e.g., Castoldi et al., 2013, Castoldi et al., 2012). In a preferred embodiment of the present invention, the polypeptide ligand is an artificial polypeptide, more preferably an antibody derivative, still more preferably an scFv, which is capable of binding to a natural receptor on a diseased cell, preferably a tumor cell, more preferably a tumor cell expressing HER2, such as a breast cancer cell, ovary cancer cell, stomach cancer cell, lung cancer cell, head and neck cancer cell, osteosarcoma cell, glioblastoma multiforme cell, or salivary gland tumor cell. In a still more preferred embodiment, the heterologous polypeptide ligand is scFv capable of binding to HER2. In the most preferred embodiment, the heterologous polypeptide ligand is scFv as identified by SEQ ID NO: 16.

The term "antibody derivative", as referred to herein, refers to a molecule comprising at least one antibody variable domain, but not comprising the overall structure of an antibody. The antibody derivative is still capable of binding a target molecule. Preferably, the antibody derivative mediates the capability that the virus fuses with the cell, so that more preferably the virus then enters the cell, and still more preferably kills the cell. Said derivatives may be antibody fragments such as Fab, Fab2, scFv, Fv, or parts thereof, or other derivatives or combinations of immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is a single chain antibody, more preferably scFv which is a fusion protein of the variable regions of the heavy ($V_H$) and light chains ($V_L$) of immunoglobulins, connected with a short linker peptide. The N-terminus of $V_H$ is either connected with the C-terminus of $V_L$ or the N-terminus of $V_L$ is connected with the C-terminus of $V_H$.

The term "antibody mimetic", as referred to herein, refers to organic compounds that, like antibodies, can specifically bind antigens, but that are not structurally related to antibodies. They are usually artificial peptides or proteins with a molar mass of about 3 to 20 kDa. They may have therapeutic or diagnostic effects. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., 2011, Xu et al., 2012, Shallal et al., 2014).

A peptide linker, as referred to herein, serves to connect, within a polypeptide, polypeptide sequences derived from different sources. Such a linker serves to connect and to enable proper folding of the heterologous polypeptide ligand with glycoprotein D sequences or to connect ligand portions within the heterologous polypeptide ligand. It may also serve to connect ligand sequences with glycoprotein sequences other than gD. A linker has typically a length between 1 and 30 amino acids, preferably 5 to 25 amino acids, more preferably 8 to 20 amino acids, such as 8, 12 or 20 amino acids and may comprise any amino acids. Preferably, it comprises the amino acid(s) Gly and/or Ser and/or Thr, more preferably it comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids selected from the group consisting of Gly, Ser and/or Thr. Most preferably, it consists of the amino acids Gly and/or Ser. Linkers based on Gly and/or Ser provide flexibility, good solubility and resistance to proteolysis. Alternatively, the linker may not predominantly comprise glycine, serine and/or threonine, but glycine, serine and/or threonine may not be present or only to a minor extent.

In the recombinant herpesvirus of the present invention, the ligand may be fused to or inserted into gD. In this context, the term "fused" or "fusion", as referred to herein, refers to the addition of the ligand to the N-terminal or C-terminal amino acid of gD by peptide bonds, either directly or indirectly via a peptide linker. "Fused" or "fusion" is different from "insertion" insofar as "fused" or "fusion" means addition to a terminus of gD, whereas "insertion" means incorporation into the gD.

The term "inserted" or "insertion", as referred to herein in the sense that a ligand is inserted into gD, refers to the incorporation of the ligand into gD, wherein the incorporated ligand is introduced between two amino acids of gD by peptide bonds, either directly or indirectly via one or more peptide linkers, more specifically via an upstream and/or downstream located peptide linker with respect to the insert. The linker is directly connected to the ligand. The fusion of a ligand to gD can also be seen as an insertion of the ligand sequence into the gD precursor, exemplified by SEQ ID NO: 1, or a homologous gD, directly before amino acid 1 of mature gD; such an insertion is herein termed as fusion. The gD carrying the fused or inserted ligand is herein referred to chimeric gD. The chimeric gD is part of the virion envelope. The definition of "linker" is, as described above.

The term "inserted between amino acids 6 and 34" or "insertion between amino acids 6 and 34" or the like means that a ligand is inserted between two adjacent amino acids between, and including, amino acid 6 and amino acid 34.

The term "a heterologous peptide ligand", as referred to herein, includes one or more than one peptide ligand(s), such as 2, 3, or 4 ligands. This means that the recombinant herpesvirus of the present invention may comprise, by referring to "a heterologous peptide ligand", one heterologous peptide ligand or may comprise two or more, such as 3 or 4, of such ligands, preferably the recombinant herpesvirus comprises one or two peptide ligand(s). If more than one peptide ligand is present, the ligands may be capable of binding to the same target molecule or to different target molecules which may be present on the same cell or different cells. Preferably, one of the ligands is capable of binding to a cell present in cell culture and another ligand is capable of binding to a different target molecule present on a diseased cell. If more than one ligand are present, the ligands may be fused to or inserted into one gD being located in the gD molecule on different sites or on the same site, i.e. successively, or the ligands may be fused to or inserted into different gDs.

The term "a heterologous polypeptide ligand", as referred to herein means, in analogy to the above, one or more than one polypeptide ligand(s), such as 2, 3, or 4 ligands. Preferably, the recombinant herpesvirus comprises one polypeptide ligand. If more than one polypeptide ligand are present, the ligands may be capable of binding to the same target molecule or to different target molecules which may be present on the same or different diseased cells. If more than one ligand are present, the ligands may be fused to or inserted into one gD being located in the gD molecule on different sites or on the same site, i.e. successively, or the ligands may be fused to or inserted into different gDs.

Preferably, the recombinant herpesvirus of the present invention comprises one peptide ligand capable of binding to a target molecule present on a cell present in cell culture and one polypeptide ligand capable of binding to a target molecule present on a diseased cell.

In analogy to the above, the term "a target molecule", as referred to herein, includes one or more than one target molecule(s), such as 2, 3, or 4 target molecules. Consequently, the recombinant herpesvirus may bind to one target molecule or to more than one target molecules, such as 2, 3, or 4 different target molecules which may be present on same or different cells.

As used herein, the target molecule may be any molecule which is accessible on the surface of a cell and which can be bound by the heterologous peptide or polypeptide ligand. The target molecule may be a natural molecule such as a polypeptide, a glycolipid or a glycoside. For example, the target molecule may be a receptor, such as a protein receptor. A receptor is a molecule embedded in a membrane of a cell that receives chemical signals from the outside via binding of a ligand, causing some form of a cellular response. Alternatively, the target molecule may be a molecule that is a drug target, such as enzymes, transporters or ion-channels, present on the surface of a cell. Regarding diseased cells, the target molecules are naturally present on diseased cells of an organism, such as mentioned below, in a specific or abnormal manner. "Specific manner" may be understood in the sense that the target molecule is overexpressed on the diseased cell, whereas it is not or only to a minor extent, i.e. to an extent to which it is usually present on a respective normal cell, expressed on the normal cell. "Abnormal manner" may be understood in the sense that the target molecule is present on a diseased cell in a mutated form, as compared to the respective molecule of the respective non-diseased cell. Therefore, retargeting a herpesvirus to a target molecule, such as a specifically expressed or mutated target molecule, results in a higher infection and eradication rate of a cell carrying the target molecule as compared to a cell that does not carry the target molecule or carries the target molecule at a lower level or carries the wildtype (non-mutated) target molecule. A preferred target molecule on a diseased cell is the HER2 molecule. The respective ligand is preferably an artificial polypeptide, more preferably an antibody derivative, still more preferably an scFv, still more preferably an scFv capable of binding to HER2, most preferably the scFv as identified by SEQ ID NO: 16. The most preferred ligand/target molecule pair as regards the targeting of a diseased cell is an SEQ ID NO: 16/HER2 molecule pair.

Alternatively, the target molecule may be an artificial molecule. The term "artificial target molecule", as referred to herein, is a molecule that does not naturally occur, i. e. that has a non-natural amino acid sequence. Such artificial molecule may be constructed to be expressed by a cell on its surface, as e.g. described in Douglas et al., 1999; and Nakamura et al., 2005 or it may be bound by a cell surface. Artificial target molecules have non-naturally occurring amino acid sequences that function to bind a particular ligand or are non-naturally expressed by or bound to a cell. Artificial target molecules may be present on the surface of a cell present in cell culture which may be used for producing the recombinant herpesvirus. Preferred artificial target molecules present on a cell present in cell culture are antibodies, antibody derivatives, or antibody mimetics, more preferably an scFv, still more preferably an scFv capable of binding to a part of the GCN4 yeast transcription factor, still more preferably an scFv capable of binding to the part of the GCN4 yeast transcription factor as comprised by SEQ ID NO: 12, still more preferably the scFv as comprised by SEQ ID NO: 17, most preferably the molecule identified by the sequence of SEQ ID NO: 18. The respective ligand is preferably a part of the GCN4 yeast transcription factor, more preferably the part of the GCN4 yeast transcription factor as comprised by SEQ ID NO: 12, most preferably the sequence of SEQ ID NO: 12. The most preferred ligand/target molecule pair as regards the targeting of a cell present in cell culture is SEQ ID NO: 12/SEQ ID NO: 18 pair.

In a preferred embodiment, the target molecule present on a diseased cell is a tumor-associated receptor, preferably a member of the EGF receptor family, including HER2, EGFR, EGFRIII, or EGFR3 (ERBB3), EGFRvIII, or MET, FAP, PSMA, CXCR4, CEA, CEA-CAM, Ep-CAM, CADC, Mucins, Folate-binding protein, gp100, GD2, VEGF receptors 1 and 2, CD19, CD20, CD30, CD33, CD52, CD55, the integrin family, IGF1R, the Ephrin receptor family, the protein-tyrosine kinase (TK) family, RANKL, TRAILR1, TRAILR2, IL13Ralpha, UPAR, Tenascin, a member of the immune checkpoint family regulators, including PD-1, PD-L1, CTL-A4, TIM-3, LAG3, B7-H3, or IDO, tumor-associated glycoprotein 72, ganglioside GM2, A33, Lewis Y antigen, or MUC1, most preferably HER2. Preferably, the target molecule is HER2 which is overexpressed by some tumor cells such as breast cancer cells, ovary cancer cells, stomach cancer cells, lung cancer cells, head and neck cancer cells, osteosarcoma cells, glioblastoma multiforme cells, or salivary gland tumor cells, but is expressed at very low levels in non-malignant tissues. A tumor-associated receptor is a receptor which is expressed by a tumor cell in a specific or abnormal manner. Alternatively, the target molecule is a molecule derived from an infectious agent such as a pathogen (e.g. a virus, bacterium or parasite) that has infected a cell. The target molecule is expressed on the surface of the infected cell (such as HBsAg from HBV, gpI20 from HIV, E1 or E2 from HCV, LMP1 or LMP2 from EBV). The pathogen may result in an infectious disease, such as a chronic infectious disease. Still alternatively, the target molecule is expressed by a degenerative disorder-associated cell or by a senescent cell such as CXCR2 or the IL-1 receptor.

The term "cell", as referred to herein, is any cell which carries a target molecule and which can be infected by the recombinant herpesvirus of the present invention. The cell may be a naturally occurring cell such as a cell which is unwanted and shall be eliminated, such as a diseased cell. Examples of diseased cells are given below. Preferred diseased cells are those comprising HER2. Alternatively, the cell may be a cell—naturally occurring or modified—which serves to produce the recombinant herpesvirus. Such cell may be any cell which can be infected by the recombinant herpesvirus of the present invention and which can produce the herpesvirus. As propagation of the herpesvirus shall be avoided in diseased cells, so as to avoid the introduction of material such as DNA, RNA and/or protein of diseased cells such as tumor cells in humans, the cell for producing the herpesvirus is a cell which is not harmful if present in humans, e.g. a non-diseased cell. The cell may be present as a cell line. For producing the recombinant herpesvirus, the cell is present in cell culture. Therefore, a cell which serves to produce the recombinant herpesvirus is termed herein "cell present in cell culture". Thus, the cell may be a cultured cell suitable for growth of herpesvirus, preferably the cell is a cell line approved for herpesvirus growth. Examples of such cells are Vero, 293, 293T, HEp-2, HeLa, BHK, or RS cells, preferably Vero cells. Preferably, the cell present in cell culture has been modified to express a target molecule which is not naturally expressed by the corresponding parent cell or the cell present in cell culture has been modified and binds the target molecule on its surface. More preferably, the cell comprises as the target molecule an antibody derivative, still more preferably an scFv, still more preferably an scFv capable of binding to a part of the GCN4 yeast transcription factor, still more preferably an scFv capable of binding to the part of the GCN4 yeast transcription factor as comprised by SEQ ID NO: 12, still more preferably the scFv as comprised by SEQ ID NO: 17, most preferably the molecule identified by the sequence of SEQ ID NO: 18.

A "cultured" cell is a cell which is present in an in vitro cell culture which is maintained and propagated, as known in the art. Cultured cells are grown under controlled conditions, generally outside of their natural environment. Usually, cultured cells are derived from multicellular eukaryotes, especially animal cells. "A cell line approved for growth of herpesvirus" is meant to include any cell line which has been already shown that it can be infected by a herpesvirus, i.e. the virus enters the cell and is able to propagate and produce the virus. A cell line is a population of cells descended from a single cell and containing the same genetic composition. Preferred cells for propagation and production of the recombinant herpesvirus are Vero, 293, 293T, HEp-2, HeLa, BHK, or RS cells.

The term "diseased cell", as used herein, refers to a cell which negatively influences an organism and is, therefore, not wanted. The eradication of such a cell is desired, as its killing may be live-saving or enhances the health of an organism. In a preferred embodiment, the diseased cell is characterized by an abnormal growth, more preferably the cell is a tumor cell. In an alternative preferred embodiment, the cell is an infected cell such as a chronically infected cell, a degenerative disorder-associated cell or a senescent cell.

In case of a tumor cell, the underlying disease is a tumor, preferably selected from the group consisting of adrenal cancer, anal cancer, bile duct cancer, bladder cancer, bone cancer, brain/CNS tumors, breast cancer, cancer of unknown primary treatment, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer, small intestine cancer, stomach cancer, testicular cancer, thymus cancer, thyroid cancer, uterine sarcoma, vaginal cancer, vulvar cancer, Waldenstrom macroglobulinemia, and Wilms tumor. Preferred tumor diseases are HER2-positive cancers (like breast cancer, ovary cancer, stomach cancer, lung cancer, head and neck cancer, osteosarcoma and glioblastoma multiforme), EGFR-positive cancers (like head and neck cancer, glioblastoma multiforme, non-small cell lung cancer, breast cancer, colorectal and pancreatic cancer), EGFR-vIII-positive cancers (like glioblastoma multiforme), PSMA-positive cancers (like prostate cancer), CD20+ positive lymphoma, and EBV related tumors such as B-cell lymphoproliferative disorders such as Burkitt's lymphoma, classic Hodgkin's lymphoma, and lymphomas arising in immunocompromised individuals (post-transplant and HIV-associated lymphoproliferative disorders), T-cell lymphoproliferative disorders, angioimmunoblastic T-cell lymphoma, extranodal nasal type natural killer/T-cell lymphoma.

In case of an infected cell, the underlying disease is an infectious disease, such as a chronic infectious disease, wherein the infectious agent may be a virus, a bacterium or a parasite. Examples are tuberculosis, malaria, chronic viral hepatitis (HBV, Hepatitis D virus and HCV), acquired immune deficiency syndrome (AIDS, caused by HIV, human immunodeficiency virus), EBV related disorders, or HCMV related disorders.

In case of a degenerative disorder-associated cell, the underlying disease may be Alzheimer's disease, amyotrophic lateral sclerosis (ALS), Lou Gehrig's Disease, osteoarthritis, atherosclerosis, Charcot Marie Tooth disease (CMT), chronic obstructive pulmonary disease (COPD), chronic traumatic encephalopathy, diabetes, Ehlers-Danlos syndrome, essential tremor, Friedreich's ataxia, Huntington's disease, inflammatory bowel disease (IBD), keratoconus, keratoglobus, macular degeneration, Marfan's syndrome, multiple sclerosis, multiple system atrophy, muscular dystrophy, Niemann Pick disease, osteoporosis, Parkinson's Disease, progressive supranuclear palsy, prostatitis, retinitis pigmentosa, rheumatoid arthritis, or Tay-Sachs disease. The term "degenerative disorder-associated cell" refers to a cell which is in relationship with the disorder, meaning that an alteration of the cell contributes to the development of the disease or the cell is altered as a consequence of the disease. Destroying the cell results in the treatment of the disease.

In case of a senescent cell, the underlying disease is a senescence-associated disease, such as (i) rare genetic diseases called progeroid syndromes, characterized by premature aging: Werner syndrome (WS), Bloom syndrome (BS), Rothmund-Thomson syndrome (RTS), Cockayne syndrome (CS), xeroderma pigmentosum (XP), trichothiodystrophy or Hutchinson-Gilford Progeria syndrome (HGPS) or (ii) common age related disorders, such as obesity, type 2 diabetes, sarcopenia, osteoarthritis, idiopathic pulmonary fibrosis, chronic obstructive pulmonary disease, cataracts, neurodegenerative diseases, systemic autoimmune diseases (systemic lupus erythematosus, rheumatoid arthritis, or Sjögren syndrome), or multiple sclerosis.

The fusion of gD of the recombinant herpesvirus of the present invention with (a) ligand(s) serves to retarget the herpesvirus to (a) cell(s) carrying the respective target molecule(s). In addition, the recombinant herpesvirus may comprise additional modification for detargeting the recombinant herpesvirus from the natural receptors of gD. By detargeting, the ability of the recombinant herpesvirus to infect cells which comprise the natural receptor(s) of gD, however, do not comprise the target molecule(s) of the ligand(s), such as normal body cells, is reduced. Detargeting is obtained by inactivating the binding site(s) of gD to its natural receptor(s), HVEM and/or nectin-1. Inactivation of the HVEM binding site results in a detargeting from HVEM, whereas targeting of nectin-1 is maintained. Inactivation of the nectin-1 binding site results in a detargeting from nectin- 1, whereas targeting of HVEM is maintained. Inactivation of both the HVEM and nectin-1 binding sites results in detargeting from the natural receptors of gD and thus, from any cells carrying these receptors, but not carrying the target molecules of the ligand(s), such as normal body cells. Inactivation of the HVEM binding site may be performed as known in the art including the deletion of sequences from the HVEM binding site, as exemplified by deletion of amino acid residues 6 to 38, which simultaneously delete some residues critical also for interaction with nectin-1 (Menotti et al., 2008) or the inclusion of a component into the HVEM binding site, as exemplified by insertion of IL-13, or of scFv to HER2 between amino acid residues 24 and 25 (Xhou and Roizman, 2005; Menotti et al., 2008). Preferably, inactivation of the HVEM binding site, as comprised herein, is performed by the insertion of a ligand, as defined herein, between amino acids 6 and 34, more preferably between amino acids 24 and 25, with respect to mature gD as comprised by of SEQ ID NO: 1 or corresponding amino acids of a homologous gD. Alternatively to or in addition to the inactivation of the HVEM binding site, inactivation of the nectin-1 binding site may be performed. Inactivation of the nectin-1 binding site may be performed as known in the art including the deletion of sequences from the nectin-1 binding site, as exemplified by deletion of amino acid residues 6 to 38, which simultaneously delete some residues critical also for interaction with HVEM (Menotti et al., 2008), or the mutation of a critical amino acid residue in gD critical for interaction with nectin-1, Y38C (Uchida et al., 2013). Preferably, inactivation of the nectin-1 binding site is performed by the deletion of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD. More preferably, inactivation of the nectin-1 binding site is performed by insertion of a ligand, as defined herein, instead of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD. In a particularly preferred embodiment of the present invention, the recombinant herpesvirus comprises at least two ligands such as 2, 3, or 4 ligands, preferably 2 ligands, inserted into gD, wherein one of the ligands is inserted between amino acids 24 and 25 and one of the ligands is inserted instead of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD. Still more preferred, one ligand is a part of the GCN4 yeast transcription factor, still more preferably the part of the GCN4 yeast transcription factor as comprised by SEQ ID NO: 12, most preferably the sequence of SEQ ID NO: 12 (GCN4 peptide) and the other ligand is an antibody derivative, preferably an scFv, which is capable of binding to a natural receptor on a diseased cell, preferably a tumor cell, more preferably a tumor cell expressing HER2, still more preferably an scFv capable of binding to HER2, most preferably the scFv as identified by SEQ ID NO: 16. In the most preferred embodiment of the present invention, the recombinant herpesvirus comprises two ligands, SEQ ID NO: 12 and SEQ ID NO: 16, whereby SEQ ID NO: 12 is inserted between amino acids 24 and 25 and SEQ ID NO: 16 is inserted instead of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD or SEQ ID NO: 16 is inserted between amino acids 24 and 25 and SEQ ID NO: 12 is inserted instead of amino acids 35 to 39 or a subset thereof or amino acids 214 to 223 or a subset thereof, such as amino acids 215 to 223, 216 to 223, 217 to 223, 218 to 223, or 219 to 223, with respect to mature gD as comprised by SEQ ID NO: 1 or corresponding amino acids of a homologous gD.

"Inactivation", as used herein, means that (a) specific region(s) responsible for the binding of gD to its natural receptor(s) accessible on cells is (are) modified in such a way that binding capability is reduced, such as by at least 50%, 60%, 70%, 80%, 90%, 95%, 97%, 99%, or 100%, resulting in partial or complete loss of the herpesvirus to enter the cell and to kill the cell. By the term "substantially ablated", as used herein, is meant that binding capability is reduced, such as by at least 95%, 97%, 99%, or 100%.

The term "amino acids 35 to 39" or "amino acids 214 to 223" means a region consisting of amino acids 35, 36, 37, 38, and 39 or a region consisting of amino acids 214, 215, 216, 217, 218, 219, 220, 221, 222, and 223, respectively. The term "subset thereof" means one amino acid or at least 2, such as 2, 3, or 4, adjacent amino acids out of the region consisting of amino acids 35 to 39 or one amino acid or at least 2, such as 2, 3, 4, 5, 6, 7, 8, or 9, adjacent amino acids out of the region consisting of amino acids 214 to 223. Thus, "subset thereof" may mean amino acids 35, 36, 37, 38, 39, 35 to 38, 35 to 37, 35 to 36, 36 to 39, 36 to 38, 36 to 37, 37 to 39, 37 to 38, or 38 to 39. "Subset thereof" may mean amino acids 214, 215, 216, 217, 218, 219, 220, 221, 222, 223, 214 to 215, 214 to 216, 214 to 217, 214 to 218, 214 to 219, 214 to 220, 214 to 221, 214 to 222, 215 to 216, 215 to 217, 215 to 218, 215 to 219, 215 to 220, 215 to 221, 215 to 222, 215 to 223, 216 to 217, 216 to 218, 216 to 219, 216 to 220, 216 to 221, 216 to 222, 216 to 223, 217 to 218, 217 to 219, 217 to 220, 217 to 221, 217 to 222, 217 to 223, 218 to 219, 218 to 220, 218 to 221, 218 to 222, 218 to 223, 219 to 220, 219 to 221, 219 to 222, 219 to 223, 220 to 221, 220 to 222, 220 to 223, or 221 to 222. Preferably, the subset is amino acids 215 to 223, 216 to 223, 217 to 223, 218 to 223, or 219 to 223, more preferably amino acids 219 to 223. The term "a subset" may comprise one or more subsets, such as 2, 3, 4, or 5, subsets. For example, "a subset" may comprise amino acids 214 and amino acids 219 to 223 resulting in a gD that does not comprise amino acids 214 and amino acids 219 to 223. As defined herein, deletion of a subset results in the inactivation of the nectin-1 binding site of gD reducing the binding capability of gD to nectin-1, as defined herein. The numbers above refer to mature gD as comprised by SEQ ID NO: 1 or corresponding amino acids of a homologous gD.

In an embodiment thereof, the recombinant herpesvirus of the present invention may, in addition to the chimeric gD, comprise a modified gB glycoprotein. A modified gB may carry a heterologous polypeptide ligand, as defined herein. The recombinant herpesvirus of the present invention may, in addition to the chimeric gD, comprise a modified gH glycoprotein. A modified gH may carry a heterologous polypeptide ligand, as defined herein. The modified gH glycoprotein may be as disclosed in Gatta et al., 2015, but is not limited to those descriptions. The recombinant herpesvirus of the present invention may, in addition to the chimeric gD, comprise a modified gB and a modified gH glycoprotein, but not limited to those descriptions. The modification(s) of gB and/or gH serve(s) for readdressing the tropism of the herpesvirus to diseased cells, as defined herein.

The recombinant herpesvirus of the present invention may comprise a chimeric gD, but may not comprise a modified gB, or may not comprise a modified gH, or may not comprise a modified gB and a modified gH. Thus, the recombinant herpesvirus of the present invention may not comprise a gB modified to having fused to or inserted a heterologous polypeptide, such as a heterologous polypeptide ligand. Moreover, the recombinant herpesvirus of the present invention may not comprise a gH modified to having fused to or inserted a heterologous polypeptide, such as a heterologous polypeptide ligand. Moreover, the recombinant herpesvirus of the present invention may not comprise a gB modified to having fused to or inserted a heterologous polypeptide, such as a heterologous polypeptide ligand, and may not comprise a gH modified to having fused to or inserted a heterologous polypeptide, such as a heterologous polypeptide ligand.

The recombinant herpesvirus of the present invention may, furthermore, encode one or more molecule(s) that modulate(s), e.g. stimulate(s), the host immune response against a cell, preferably a diseased cell, as defined above. A molecule that modulates, e.g stimulates, the host immune response is also termed "immunotherapy molecule". Thus, the recombinant herpesvirus of the present invention may be a combined oncolytic and immunotherapeutic virus. An immunotherapeutic virus is a virus that encodes molecules that boost the host immune response to a cell, i.e. that modulate, e.g. stimulate, the host immune response so as to be directed against a cell. An example of such a virus is T-VEC (Liu et al., 2003).

Immunotherapy molecules, in addition to the chimeric gD, enable the recombinant virus, besides the specific targeting and killing of a cell via the heterologous peptide or polypeptide ligand, to modulate, e.g. stimulate, a subject's immune system in a specific or unspecific manner. Expression of immunotherapy molecules by the recombinant virus in a subject can induce an immune response which finally results in the killing of diseased cells. Immunotherapy may act specifically wherein the immunotherapy molecules modulate, e.g. stimulate, the subject's immune system against one or some specific antigen(s) present on (a) cell(s). For example, an immunotherapy molecule may be an antibody which is directed against a specific cell surface receptor, e.g. CD20, CD274, and CD279. Once bound to an antigen, antibodies can induce antibody-dependent cell-mediated cytotoxicity, activate the complement system, or prevent a receptor from interacting with its ligand. All that can lead to cell death. Preferred cells are tumor cells. This technique is known and approved in the art. There are multiple antibodies which are approved to treat cancer, including Alemtuzumab, Ipilimumab, Nivolumab, Ofatumumab, and Rituximab. Alternatively, the immunotherapy molecule can act non-specifically by stimulating the subject's immune system. Examples of immunotherapy molecules are inter alias cytokines, chemokines or immune checkpoint regulators. For example, some cytokines have the ability to enhance anti-tumor activity and can be used as passive cancer treatments. The use of cytokines as immunotherapy molecules is known in the art. Examples of cytokines are GM-CSF, interleukin-2, interleukin-12, or interferon-α. GM-CSF is used, for example in the treatment of hormone-refractory prostate cancer or leukemia. Interleukin-2 is used, for example, in the treatment of malignant melanoma and renal cell carcinoma. IL-12 is used in the experimental treatment of glioblastoma. Interferon-α is, for example, used in the treatment of hairy-cell leukemia, AIDS-related Kaposi's sarcoma, follicular lymphoma, chronic myeloid leukemia and malignant melanoma.

The recombinant herpesvirus of the present invention may be attenuated, for example by deletions in or alterations of genes known to attenuate virus virulence, such as the viral genes $y_1 34.5$, UL39, and/or ICP47. The term "attenuated" refers to a weakened or less virulent herpesvirus. Preferred is a conditional attenuation, wherein the attenuation affects only non-diseased cells. More preferred, only the diseased cells such as tumor cells are affected by the full virulence of the herpesvirus. A conditional attenuation can be achieved, for example, by the substitution of the promoter region of the $y_1 34.5$, UL39 and/or ICP47 gene with a promoter of a human gene that is exclusively expressed in diseased cells (e.g. the survivin promoter in tumor cells). Further modifications for a conditional attenuation may include the substitution of regulatory regions responsible for the transcription of IE genes (immediate early genes) like the ICP-4 promoter region with promoter regions of genes exclusively expressed in diseased cells (e.g. the survivin promoter). This change will result in a replication conditional HSV, which is able to replicate in diseased cells but not in normal cells. Additional modification of the virus may include the insertion of sequence elements responsive to microRNAs (miRs), which are abundant in normal but not tumor cells, into the 3' untranslated region of essential HSV genes like ICP4. The result will be again a virus that is replication incompetent only in normal cells.

In a second aspect, the present invention provides a pharmaceutical composition comprising the recombinant herpesvirus of the present invention and a pharmaceutically acceptable carrier, optionally additionally comprising one or more molecule(s) that modulate(s), e.g. stimulate(s), the host immune response against a cell, preferably a diseased cell, as defined above. The recombinant herpesvirus of the present invention can be used as a medicament. For the production of the medicament the herpesvirus may be in a pharmaceutical dosage form comprising the recombinant herpesvirus of the present invention and a mixture of ingredients such as pharmaceutically acceptable carriers which provide desirable characteristics. The pharmaceutical composition comprises one or more suitable pharmaceutically acceptable carrier which is/are known to those skilled in the art. The pharmaceutical composition may additionally comprise one or more molecule(s) that modulate(s), e.g. stimulate(s), the host immune response against a cell. The definition of the one or more molecule(s) that modulate(s), e.g. stimulate(s), the host immune response against a cell, as is referred to above under the first aspect of the present invention.

The pharmaceutical composition can be manufactured for systemic, nasal, parenteral, vaginal, topic, vaginal, intratumoral administration. Parental administration includes subcutaneous, intracutaneous, intramuscular, intravenous or intraperitoneal administration.

The pharmaceutical composition can be formulated as various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories, and dosage forms for topical or transdermal administration such as ointments, pastes, creams, lotions, gels, powders, solutions, sprays, inhalants or patches.

The specific therapeutically effective dose level for any particular subject will depend upon a variety of factors including the activity of the recombinant herpesvirus of the present invention, the dosage form, the age, body weight and sex of the subject, the duration of the treatment and like factors well known in the medical arts.

The total dose of the compounds of this invention administered to a subject in single or in multiple doses may be in amounts, for example, from $10^3$ to $10^{10}$. Single dose compositions may contain such amounts or submultiples thereof to make up the daily dose. The dosages of the recombinant herpesvirus may be defined as the number of plaque forming unit (pfu). Examples of dosages include $10^3$, $10^4$, $10^5$, $10^6$, $10^7$, $10^8$, $10^9$, or $10^{10}$.

The recombinant herpesvirus of the present invention serves to treat diseases whereby diseased cells express specific target molecules on their surface such that they are accessible from the outside of the cell, which target molecules are not produced by a normal cell or are produced by the normal cell to a lower degree. The normal cell may be the respective normal cell. "Respective" means that the diseased and normal cells are of the same origin, however, cells develop into diseased cells due to disease-generating influences, whereas other cells of same origin remain healthy.

In a third aspect, the present invention provides the recombinant herpesvirus of the present invention, optionally in combination with one or more molecule(s) that modulate(s), e.g. stimulate(s), the host immune response against a cell, preferably a diseased cell, as defined above, for use in the treatment of a tumor, infection, degenerative disorder or senescence-associated disease. The recombinant herpesvirus of the present invention and the molecule that modulates, e.g. stimulates, the host immune response against a cell can be present within the same pharmaceutical composition or within different pharmaceutical compositions. If they are present in different pharmaceutical compositions, they may be administered simultaneously, or subsequently, either the herpesvirus before the molecule or the molecule before the herpesvirus. The herpesvirus or the molecule may be administered at different frequencies and/or time points. However, a combined treatment comprises that the herpesvirus and the molecule are administered at time intervals and/or time points that allow the simultaneous treatment of the disease.

The present invention also discloses a method of treating a subject having a tumor, infection, degenerative disorder or senescence-associated disorder by administering a pharmaceutically effective amount of the recombinant herpesvirus of the present invention.

The recombinant herpesvirus of the present invention may be administered to a subject in combination with further treatments which modulates, e.g. stimulate, the host immune response against a cell, preferably a diseased cell, and/or serve to treat the specific disease of the subject. Such further treatments may include other drugs, chemotherapy, radiotherapy, immunotherapy, combined virotherapy, etc.

The present invention also discloses the use of the herpesvirus of the present invention, optionally in combination with one or more molecule(s) that modulate(s), e.g. stimulate(s), the host immune response against a cell, preferably a diseased cell, as defined above, for the preparation of a pharmaceutical composition for the treatment of a tumor, infection, degenerative disorder or senescence-associated disease.

The subjects that are treated by the recombinant herpesvirus of the present invention are preferably humans.

In a fourth aspect, the present invention provides a nucleic acid molecule comprising a nucleic acid coding for the chimeric gD of the present invention having fused or inserted the heterologous peptide ligand and optionally the heterologous polypeptide ligand. The nucleic acid molecule may be the genome of the recombinant herpesvirus of the present invention or a part thereof. Preferably, the nucleic acid molecule encodes the precursor form of the chimeric gD including the signal sequence of the gD glycoprotein. If the chimeric gD was engineered to harbor the ligand fused to its N-terminal amino acid, the corresponding nucleic acid has the nucleic acid sequence of the ligand inserted between the last amino acid of the signal sequence and the first amino acid of the mature protein.

In a fifth aspect, the present invention provides a vector comprising the nucleic acid molecule. Suitable vectors are known in the art and include plasmids, cosmids, artificial chromosomes (e.g. bacterial, yeast or human), bacteriophages, viral vectors (retroviruses, lentiviruses, adenoviruses, adeno-associated viruses), in particular baculovirus vector, or nano-engineered substances (e.g. ormosils). In one embodiment, the vector is modified, in particular by a deletion, insertion and/or mutation of one or more nucleic acid bases, such that its virulence is attenuated, preferably in case of a viral vector, or that it replicates conditionally in diseased cells but not in non-diseased cells. For example, deletion of one or both copies of the $\gamma_1 34.5$ gene, the UL39 gene, the ICP47 gene results in attenuation of the virus. Attenuation or attenuated refers to weakened or less virulent virus.

Moreover, the substitution of the promoter region of the $\gamma_1 34.5$ gene with a promoter of a human gene that is exclusively expressed in diseased cells, e.g. tumor cells (e.g. survivin promoter in tumor cells), which will result in an attenuated phenotype in non-diseased cells and non-attenuated phenotype in diseased cells, is included. Further modifications may include the substitution of regulatory regions responsible for the transcription of IE genes like the ICP-4 promoter region with promoters of genes exclusively expressed in diseased cells (e.g. survivin promoter). This change will produce a replication conditional herpesvirus, able to replicate in diseased cells but not in normal cells. Cell culture cells for propagation of the virus progeny will provide high levels of specific promoter activating proteins to allow for the production of high virus yields.

In a sixth aspect, the present invention provides a polypeptide comprising the chimeric gD, having fused or inserted the heterologous peptide ligand and optionally the heterologous polypeptide ligand.

In a seventh aspect, the present invention provides a cell comprising the recombinant herpesvirus, the nucleic acid molecule comprising a nucleic acid coding for the chimeric gD of the present invention having fused or inserted the heterologous peptide ligand and optionally the heterologous polypeptide ligand, the vector comprising the nucleic acid molecule, or the polypeptide comprising the chimeric gD having fused or inserted the heterologous peptide ligand and optionally the heterologous polypeptide ligand. Preferably, the cell is a cell culture cell. Suitable cell cultures and culturing techniques are well known in the art (Peterson and Goyal, 1988).

In an eighth aspect, the present invention provides a method for infecting a cell using the recombinant herpesvirus of the present invention. The object of the present invention is the provision of a recombinant herpesvirus which infects a cell unwanted in a subject, propagates therein, lyses the cell and, thereby, kills the cell. The method for infecting also serves for growth of the recombinant herpesvirus in a cell present in cell culture. "Infecting" means that the virus enters the cell via fusion of the viral surface membrane with the cell membrane and viral components such as the viral genome are released into the cell. Methods of infecting a cell with a virus are known in the art, e.g. by incubating the virus with the cell to be infected (Florence et al., 1992; Peterson and Goyal, 1988). "Killing" means that the cell is totally eliminated due to the infection of the herpesvirus of the present invention, the production of viral particles within the cell and, finally, the release of the new viral particles by lysing the cell. Cells which carry the target molecule of the ligand on their surface can be used to test the lytic efficacy of the recombinant herpesvirus. For example, the cell may be a diseased cell obtained from a subject, for example a tumor cell. This cell is infected and thereby killed by the recombinant herpesvirus. The successful killing of the cell is indicative of the cell specificity of the recombinant herpesvirus, in order to evaluate the therapeutic success of eliminating cells such as tumor cells from the subject. In a further embodiment, also non-diseased cells may be obtained from the same subject or from a control subject not suffering from the disease, i.e. the cells do not carry the target molecule of the ligand on their surface or carry the target molecule to a lower extent. By this, it can be tested whether and/or to which extent the non-diseased cell is susceptible to infection by the recombinant herpesvirus. In another embodiment, diseased cells comprised in a population of cells (e.g. tissue such as blood) comprising non-diseased cells and diseased cells (for example tumor cells such as leukemia cells) are killed after isolation of the population of cells from a subject (e.g. leukapheresis). This serves to obtain a population of cells free of diseased cells, e.g. blood free of diseased cells such as leukemia cells, in particular for a later transplant of the population of cells into a subject, preferably into the same subject the population of cells was isolated from. In case of blood and leukemia, for example, this method provides for re-infusion of blood free of tumor cells. The method for killing a cell using the recombinant herpesvirus of the present invention may be an in-vitro or in-vivo method.

In a ninth aspect, the present invention provides an in-vitro method for producing a recombinant herpesvirus in a cell present in cell culture using the recombinant herpesvirus of the present invention, preferably wherein the cell expresses or binds as a target molecule an artificial molecule, more preferably the target molecule comprises an antibody, an antibody derivative or an antibody mimetic, still more preferably an scFv, still more preferably an scFv capable of binding to a part of the GCN4 yeast transcription factor, still more preferably an scFv capable of binding to the part of the GCN4 yeast transcription factor as comprised by SEQ ID NO: 12, still more preferably the scFv as comprised by SEQ ID NO: 17, most preferably the molecule identified by the sequence of SEQ ID NO: 18.

The recombinant herpesvirus of the present invention serves the purpose of infecting and killing diseased cells in humans. This requires the provision of the herpesvirus and, therefore, its propagation and production. As propagation of the herpesvirus shall be avoided in diseased cells, so as to avoid the introduction of material such as DNA, RNA and/or protein of diseased cells such as tumor cells in humans, the recombinant herpesvirus has to be engineered to be capable of infecting also non-diseased cells. This requires the retargeting of the recombinant herpesvirus to diseased cells for killing and to non-diseased cells for propagation. Therefore, the ninth aspect of the present invention comprises the modification of gD of the recombinant herpesvirus with more than one, such as 2, 3 or 4, preferably 2, ligands.

Consequently, in an embodiment of the ninth aspect, the recombinant herpesvirus comprises a heterologous peptide ligand, fused to or inserted into gD, capable of binding to a target molecule present on the cell present in cell culture, and an additional ligand which is a heterologous peptide ligand or heterologous polypeptide ligand, preferably a heterologous polypeptide ligand, fused to or inserted into gD, capable of binding to a target molecule present on a diseased cell.

Suitable techniques and conditions for growing herpesvirus in a cell are well known in the art (Florence et al., 1992; Peterson and Goyal, 1988) and include incubating the herpesvirus with the cell and recovering the herpesvirus from the medium of the infected cell culture. The cell by which the recombinant herpesvirus is produced carries a target molecule to which the recombinant herpesvirus binds via the heterologous peptide ligand. Preferably, the target molecule is an artificial target molecule. The artificial target molecule is specifically constructed to bind to the heterologous peptide ligand. Conversely, the ligand is specifically selected and constructed to bind to the artificial target molecule. Thus, the target molecule may be an antibody which is not naturally produced by the target cell, an antibody derivative or an antibody mimetic, preferably an scFv. The heterologous peptide ligand may be a natural polypeptide, preferably a fungal or bacterial polypeptide, such as a polypeptide from the genus *Saccharomyces* such as *Saccharomyces cerevisiae*, or an artificial polypeptide such as a part of the natural polypeptide capable of binding to the target molecule. The cell may be any cultured cell which is suitable for growth of herpesvirus. Preferably, the cell is a non-diseased cell. The cell may be present as a cell line or may be an isolated cell, preferably the cell is present as a cell line. The cell line may be approved for herpesvirus growth. Suitable cell lines are Vero, 293, 293T, HEp-2, HeLa, BHK, or RS cells, most preferably a Vero cell.

A "cultured" cell is a cell which is present in an in vitro cell culture which is maintained and propagated, as known in the art. Cultured cells are grown under controlled conditions, generally outside of their natural environment. Usually, cultured cells are derived from multicellular eukaryotes, especially animal cells. "A cell line approved for growth of herpesvirus" is meant to include any cell line which has been already shown that it can be infected by a herpesvirus, i. e. the virus enters the cell, and is able to propagate and produce the virus. A cell line is a population of cells descended from a single cell and containing the same genetic composition. Preferred cells for propagation and production of the recombinant herpesvirus are Vero, 293, 293T, HEp-2, HeLa, BHK, or RS cells.

In a preferred embodiment of the in-vitro method, the target molecule is an antibody derivative capable of binding to the peptide ligand. More preferably, the heterologous peptide ligand is a part of the GCN4 yeast transcription factor, the target molecule is an antibody derivative capable of binding to the ligand and the cell is a cell which has been modified to express the target molecule. Most preferably, the heterologous peptide ligand is the molecule identified by the sequence of SEQ ID NO: 12, the target molecule is the molecule identified by the sequence of SEQ ID NO: 18 (including the scFv sequence and human nectin-1 (PVRL1) residues Met143 to Val517) and the cell is the Vero cell line which has been modified to express the molecule identified by the sequence of SEQ ID NO: 18, herein named Vero-GCN4R cell line. SEQ ID NO: 19 identifies the nucleotide sequence encoding scFv-GCN4-nectin-1 chimera, as identified by SEQ ID NO: 18. SEQ ID NO: 17 identifies the amino acid sequence of scFv to GCN4 peptide comprising an N-terminal leader peptide, an HA tag sequence, a short GA linker, and the scFv sequence.

The Vero-GCN4R cell line expresses an artificial receptor being an scFv to the GCN4 peptide. The Vero-GCN4R cell line serves the purpose of enabling the cultivation of herpesvirus recombinants retargeted to cancer cells. Growth and production of oncolytic recombinant herpesvirus destined to human use should be avoided in cancer cells, in order to avoid the possible, accidental introduction of tumor-derived material (DNA, RNA, proteins) into humans. At the same time, the herpesvirus should be capable of infecting diseased cells. Therefore, the Vero-GCN4R cell line and a cancer cell-retargeted herpesvirus were constructed. The Vero-GCN4R cell line expresses an artificial receptor made of an scFv to the GCN4 peptide, fused to extracellular domains 2 and 3, transmembrane (TM) and C-tail of nectin-1. The cancer cell retargeted herpesvirus expresses the GCN4 peptide in gD. Consequently, the recombinant herpesvirus is simultaneously retargeted to cancer cells, in order to infect and kill cancer cells, and to the Vero-GCN4R cell line for virus growth and production.

In a particularly preferred embodiment of the ninth aspect, gD comprises a peptide ligand capable of binding to a target molecule present on a cell present in cell culture, whereby the ligand may be an artificial polypeptide, more preferably a part of a natural polypeptide, and still more preferably a part of the GCN4 yeast transcription factor, and a polypeptide ligand capable of binding to a target molecule present on a diseased cell, whereby the polypeptide ligand may be an antibody, an antibody derivative or an antibody mimetic, still more preferably an scFv, and still more preferably an scFv capable of binding to HER2. In the most preferred embodiment, the recombinant herpesvirus comprises a chimeric gD comprising the molecule identified by SEQ ID NO: 12 and an scFv identified by SEQ ID NO: 16. Such herpesvirus is capable of infecting the Vero-GCN4R cell line expressing the molecule identified by the sequence of SEQ ID NO: 18 for propagation and of infecting a tumor cell through HER2 present on the tumor cell for killing the tumor cell.

FIGURES

FIG. 1: Genome organization of R-87, R-89, R-97, R-99 and R-99-2. Sequence arrangement of HSV-1 genome shows the inverted repeat IR sequences as rectangular boxes. The GCN4 peptide, bracketed by upstream and downstream Gly-Ser linkers, is inserted between AA 24 and 25 of gD in R-87 and R-89. The GCN4 peptide, bracketed by upstream and downstream Gly-Ser linkers, is inserted in place of AA 35-39 of gD in R-97, in place of AA 214-223 of gD in R-99, in place of AA 219-223 of gD in R-97, The scFv-HER2 sequence (VL-linker-VH) is inserted in place of AA 35-39 of gD in R-87. The scFv-HER2 sequence (VL-linker-VH) is inserted in place of AA 214-223 of gD in R-89. The scFv-HER2 sequence (VL-linker-VH) is inserted between AA 24 and 25 of gD in R-97, R-99 and R-99-2. All recombinants carry the LOX-P-bracketed p-Belo-BAC and EGFP sequences inserted between UL3-UL4 region.

FIG. 2: Tropism of R-87. R-87 was grown in SK-OV-3 (A) or in Vero-GCN4R (B) cells. J cells express no receptor for wt-HSV. J-HER2, J-nectin-1, J-HVEM only express the indicated receptor. The indicated cells were infected with R-87 and monitored for EGFP by fluorescence microscopy. Cells in panels e, f, g, and h were infected in presence of Herceptin/Trastuzumab at neutralizing dose (28 μg/ml). R-87 infects both the Vero-GCN4R cells (b, f), and the HER2-positive cancer cell line SK-OV-3 (c, g), in addition to the J-HER2 cells (d, h), It also infects wt-Vero cells, which express a simian ortholog of HER2 (a). Herceptin inhibits R-87 infection of wt-Vero, SK-OV-3 and J-HER2 cells (e, g, h), but not of Vero-GCN4R cells (f). R-87 fails to infect J-nectin-1, J-HVEM and -J cells (i, j, k), since it has been detargeted from the gD receptors HVEM and nectin-1.

FIG. 3: Tropism of R-89. R-89 was grown in SK-OV-3 (A) or in Vero-GCN4R (B) cells. J cells express no receptor for wt-HSV. J-HER2, J-nectin-1, J-HVEM only express the indicated receptor. The indicated cells were infected with R-89 and monitored for EGFP by fluorescence microscopy. Cells in panels e, f, g, and h were infected in presence of Herceptin/Trastuzumab at neutralizing dose (28 μg/ml). R-89 infects both the Vero-GCN4R cells (b, f), and the HER2-positive cancer cell line SK-OV-3 (c, g), in addition to the J-HER2 cells (d, h); it infects poorly wt-Vero cells, which express a simian ortholog of HER2 (a). Herceptin inhibits R-89 infection of wt-Vero, SK-OV-3 and J-HER2 cells (e, g, h), but not of Vero-GCN4R cells (f). R-89 fails to infect J-nectin-1, J-HVEM and J cells (i, j, k), since it has been detargeted from the gD receptors HVEM and nectin-1.

FIG. 4: Tropism of R-97. R-97 was grown in SK-OV-3 cells. J cells express no receptor for wt-HSV. J-HER2, J-nectin-1, J-HVEM only express the indicated receptor. The indicated cells were infected with R-97 and monitored for EGFP by fluorescence microscopy. Cells in panels e, f, g, and h were infected in presence of Herceptin/Trastuzumab at neutralizing dose (28 μg/ml). R-97 infects both the Vero-GCN4R cells (b, f), and the HER2-positive cancer cell line SK-OV-3 (c, g), in addition to the J-HER2 cells (d, h); it also infects wt-Vero cells, which express a simian ortholog of HER2 (a). Herceptin inhibits R-97 infection of wt-Vero, SK-OV-3 and J-HER2 cells (e, g, h), but not of Vero-GCN4R cells (f). R-97 fails to infect J-nectin-1, J-HVEM and J cells (i, j, k), since it has been detargeted from gD receptors HVEM and nectin-1.

FIG. 5: Tropism of R-99. R-99 was grown in SK-OV-3 (A) or in Vero-GCN4R (B) cells. J cells express no receptor for wt-HSV. J-HER2, J-nectin-1, J-HVEM only express the indicated receptor. The indicated cells were infected with R-99 and monitored for EGFP by fluorescence microscopy. Cells in panels e, f, g, and h were infected in presence of Herceptin/Trastuzumab at neutralizing dose (28 μg/ml). R-99 infects both the Vero-GCN4R cells (b, f), and the HER2-positive cancer cell line SK-OV-3 (c, g), in addition to the J-HER2 cells (d, h); it also infects wt-Vero cells, which express a simian ortholog of HER2 (a). Herceptin inhibits R-99 infection of wt-Vero, SK-OV-3 and J-HER2 cells (e, g, h), but not of Vero-GCN4R cells (f). R-99 fails to infect J-nectin-1, J-HVEM and J cells (i, j, k), since it has been detargeted from gD receptors HVEM and nectin-1.

FIG. 6: Tropism of R-99-2. R-99-2 was grown in SK-OV-3 cells. J cells express no receptor for wt-HSV. J-HER2, J-nectin-1, J-HVEM only express the indicated receptor. The indicated cells were infected with R-99-2 and monitored for EGFP by fluorescence microscopy. Cells in panels e, f, g, and h were infected in presence of Herceptin/Trastuzumab at neutralizing dose (28 μg/ml). R-99-2 infects both the Vero-GCN4R cells (b, f), and the HER2-positive cancer cell line SK-OV-3 (c, g), in addition to the J-HER2 cells (d, h); it also infects wt-Vero cells, which express a simian ortholog of HER2 (a). Herceptin inhibits R-99-2 infection of wt-Vero, SK-OV-3 and J-HER2 cells (e, g, h), but not of Vero-GCN4R cells (f). R-99-2 fails to infect J-nectin-1, J-HVEM and J cells (i, j, k), since it has been detargeted from gD receptors HVEM and nectin-1.

Figure 7:
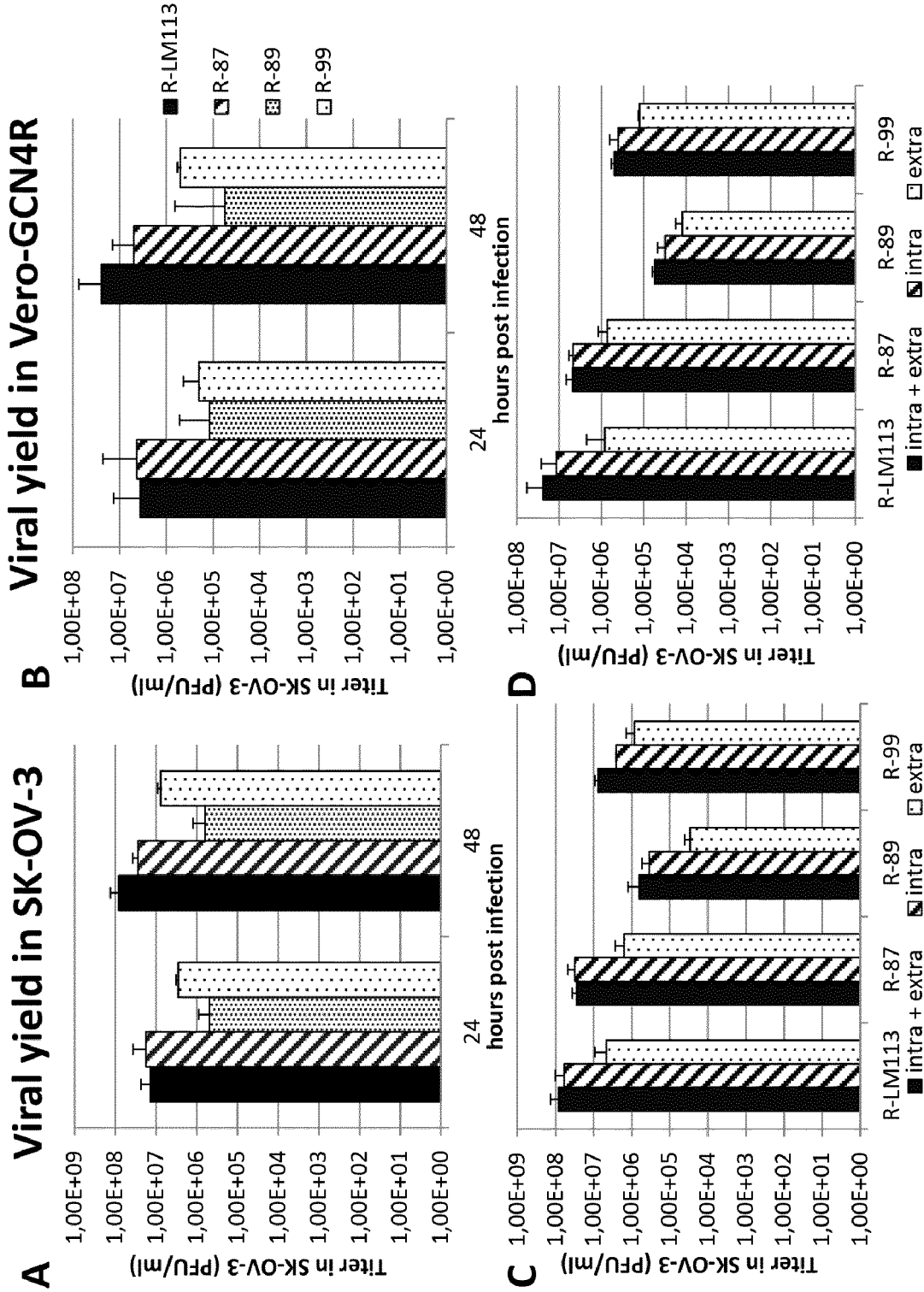

FIG. 7: Yield of recombinants R-87, R-89, R-99, and of R-LM113, in SK-OV-3 cells (A) and in Vero-GCN4R cells (B), and release of progeny virus to the extracellular medium (C, D). The extent of R-87, R-89 and R-99 replication in Vero-GCN4R, or in SK-OV-3 cells was compared to that of R-LM113 virus. Cells were infected with the indicated viruses at MOI 0.1 PFU/cell (inoculum titrated in Vero-GCN4R for replication in Vero-GCN4R, and in SK-OV-3 cells for replication in SK-OV-3 cells). Samples were collected at 24 and 48 hours post infection and progeny virus was titrated in SK-OV-3 cells (A, B). SK-OV-3 (C), or Vero-GCN4R (D) cells were infected with R-87, R-89, R-99 and R-LM113 at MOI 0.1 PFU/cell as in panel A (inoculum was titrated in SK-OV-3 cells). Samples were collected at 48 hours post infection and progeny virions released in the extracellular medium (extra), present in the cell-associated fraction (intra), or cell-associated plus medium (intra+extra) were titrated.

Figure 8:
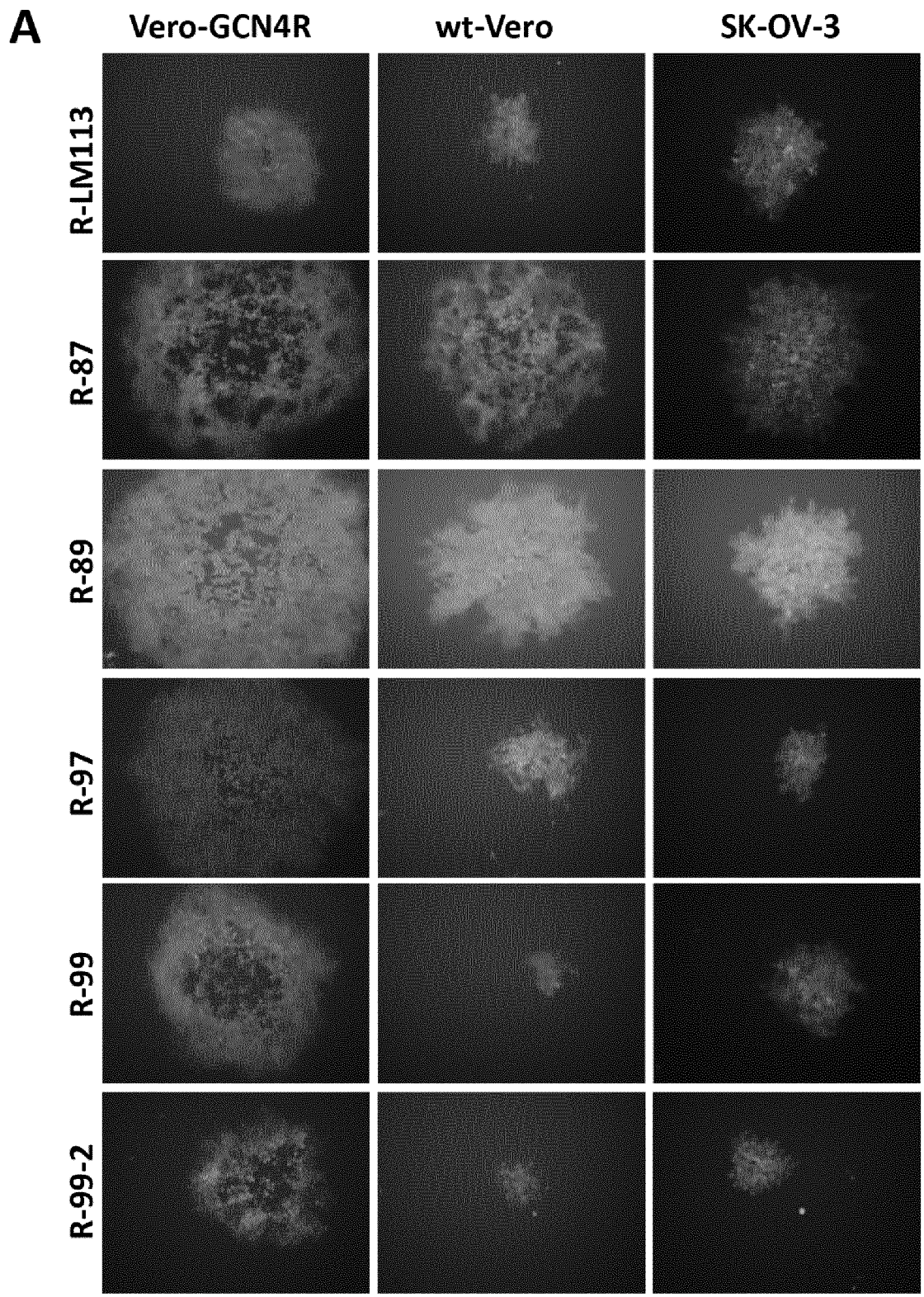
Figure 8:
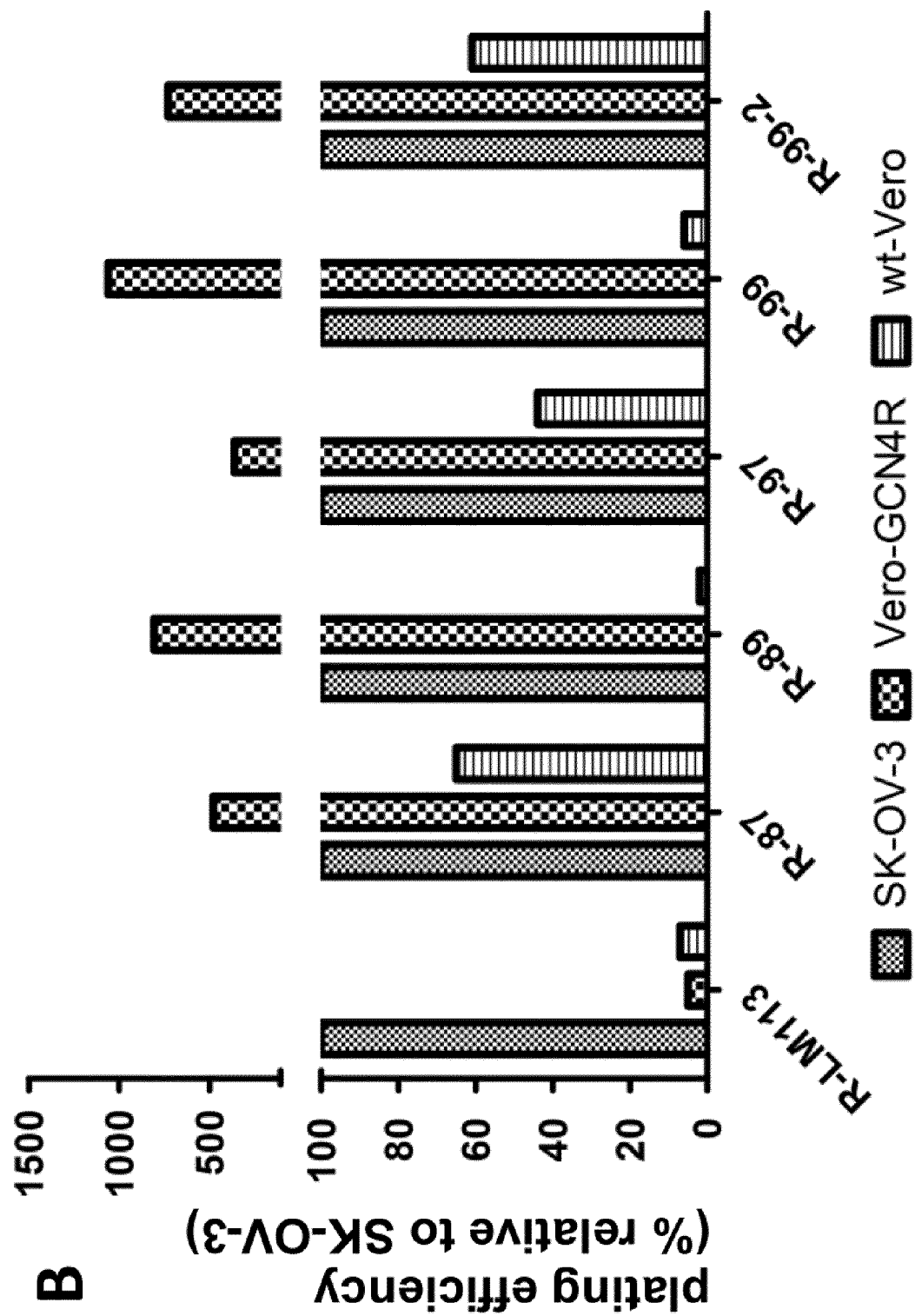

FIG. 8: Plaque size and plating efficiency of R-87, R-89, R-97, R-99 and R-99-2 in different cell lines. (A) Replicate aliquots of R-87, R-89, R-97, R-99, R-99-2 and R-LM113 for comparison, were plated in Vero-GCN4R, wt-Vero, and SK-OV-3 cells. Plaques were scored 3 days later at fluorescence microscope. (B) Relative plating efficiency of R-87, R-89, R-97, R-99, R-99-2 and R-LM113 in different cell lines. The number of scored plaques is expressed as percentage of the plaques scored in SK-OV-3 cells.

Figure 9:
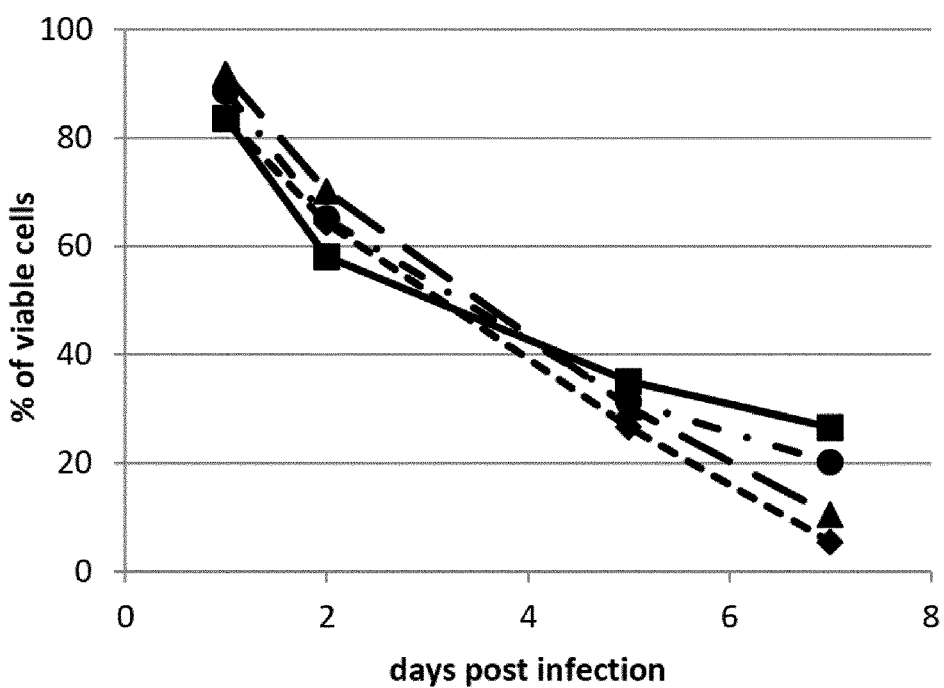
Figure 9:
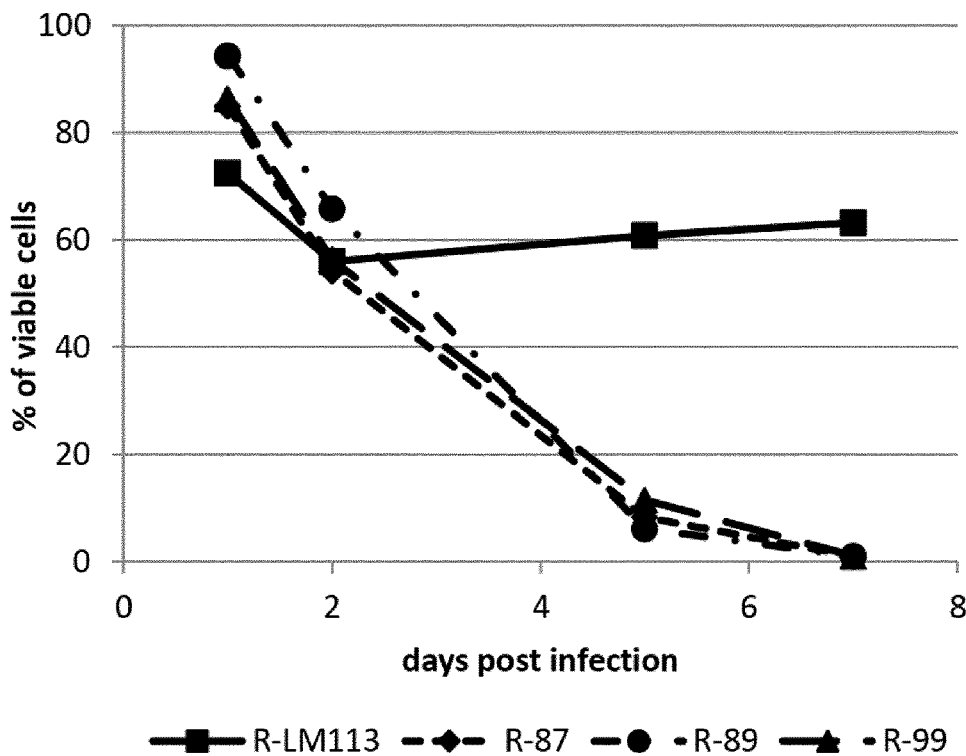

FIG. 9: Cytotoxicity caused by R-87, R-89, R-99, and R-LM113, to SK-OV-3 (A) and Vero-GCN4R cells (B). Cells were infected with the indicated viruses (3 PFU/cell). Cytotoxicity was measured through Alamar-blue assay at the indicated days after infection. It can be seen that all viruses caused cytotoxicity to SK-OV-3 and to Vero-GCN4R, except for R-LM113 in Vero-GCN4R cells, consistent with the fact that this virus is not retargeted to the GCN4R.

SEQUENCES

SEQ ID NO: 1: amino acid sequence of HSV-1 gD wild type, precursor (Human herpesvirus 1 strain F, GenBank accession number: GU734771.1; gD encoded by positions 138281 to 139465).

SEQ ID NO: 2: Nucleotide sequence of chimeric gD-GCN4, scFv HER2 of R-87

SEQ ID NO: 3: Amino acid sequence of the precursor of gD (SEQ ID NO: 1) having inserted the GCN4 peptide between amino acids 24 and 25 of mature gD, after cleavage of the signal sequence (formed by amino acids 1-25), and scFv to HER2 receptor in replacement of amino acids 35 to 39 of mature gD, as encoded by the construct R-87. The GCN4 peptide is flanked by a Ser-Gly linker.

SEQ ID NO: 4: Nucleotide sequence of chimeric gD-GCN4, scFv HER2 of R-89

SEQ ID NO: 5: Amino acid sequence of the precursor of gD (SEQ ID NO: 1) having inserted the GCN4 peptide between amino acids 24 and 25 of mature gD, and scFv to HER2 receptor in replacement of amino acids 214-223 of mature gD, as encoded by the construct R-89. The GCN4 peptide is flanked by a Ser-Gly linker.

SEQ ID NO: 6: Nucleotide sequence of chimeric gD-GCN4, scFv HER2 of R-97

SEQ ID NO: 7: Amino acid sequence of the precursor of gD (SEQ ID NO: 1) having inserted the scFv to HER2 receptor between amino acids 24 and 25 of mature gD, and the GCN4 peptide in replacement of amino acids 35 to 39 of mature gD, as encoded by the construct R-97. The GCN4 peptide is flanked by a Ser-Gly linker.

SEQ ID NO: 8: Nucleotide sequence of chimeric gD-GCN4, scFv HER2 of R-99

SEQ ID NO: 9: Amino acid sequence of the precursor of gD (SEQ ID NO: 1) having inserted the scFv to HER2 receptor between amino acids 24 and 25 of mature gD, and the GCN4 peptide in replacement of amino acids 214 to 223 of mature gD, as encoded by the construct R-99. The GCN4 peptide is flanked by a Ser-Gly linker.

SEQ ID NO: 10: Nucleotide sequence of chimeric gD-GCN4, scFv HER2 of R-99-2

SEQ ID NO: 11: Amino acid sequence of the precursor of gD (SEQ ID NO: 1) having inserted the scFv to HER2 receptor between amino acids 24 and 25 of mature gD, and the GCN4 peptide in replacement of amino acids 219 to 223 of mature gD, as encoded by the construct R-99-2. The GCN4 peptide is flanked by a Ser-Gly linker.

SEQ ID NO: 12: GCN4 peptide—Amino acid sequence of GCN4 peptide including bracketing upstream and downstream GS linkers. The GCN4 epitope is YHLENEVARLKK.

SEQ ID NO: 13: GCN4 epitope

SEQ ID NO: 14: Amino acid sequence of the GCN4 yeast transcription factor UniProtKB-P03069

SEQ ID NO: 15: Genbank accession number AJ585687.1 (gene encoding the GCN4 yeast transcription factor)

SEQ ID NO: 16: Amino acid sequence of scFv HER2 cassette, flanked by two linkers, EN and SSGGGSGSGGS (SEQ ID NO: 54).

SEQ ID NO: 17: amino acid sequence of scFv to GCN4 peptide comprising an N-terminal leader peptide, an HA tag sequence, a short GA linker, and the scFv sequence SEQ ID NO: 18: amino acid sequence encoded by SEQ ID NO: 19; amino acid sequence of the scFv capable of binding to the GCN4 peptide comprising an N-terminal leader peptide, an HA tag sequence, a short GA linker, the scFv sequence from amino acids 33 to 275, a short GSGA linker, and human nectin-1 (PVRL1) residues Met143 to Val517

SEQ ID NO: 19: nucleotide sequence encoding scFv-GCN4-nectin-1 chimera

SEQ ID NO: 20: Primer gD24_galK_f

SEQ ID NO: 21: Primer gD25_galK_r

SEQ ID NO: 22: Primer galK_827_f

SEQ ID NO: 23: Primer galK_1142_r

SEQ ID NO: 24: GCN4 peptide cassette—Nucleotide sequence of GCN4 peptide including bracketing upstream and downstream GS linkers (ggatcc and ggcagc)

SEQ ID NO: 25: Primer gD24_GCN4 JB

SEQ ID NO: 26: Primer gD25_GCN4_rB

SEQ ID NO: 27: Nucleotide sequence of chimeric gD-GCN4 of R-81

SEQ ID NO: 28: Amino acid sequence of the precursor of gD (SEQ ID NO: 1) having inserted the GCN4 peptide between amino acids 24 and 25 of mature gD, as encoded by the construct R-81. The GCN4 peptide is flanked by a Ser-Gly linker.

SEQ ID NO: 29: Primer gD_ext_f

SEQ ID NO: 30: Primer gD_ext_r

SEQ ID NO: 31: Primer galK_gD35_F

SEQ ID NO: 32: Primer galK_gD39_R

SEQ ID NO: 33: Nucleotide sequence of scFv HER2 cassette
SEQ ID NO: 34: Primer gD-34-scFvHER2-F
SEQ ID NO: 35: Primer gD-40-scFvHER2-R
SEQ ID NO: 36: Primer scFv_456_r
SEQ ID NO: 37: Primer galK_gD214_F
SEQ ID NO: 38: Primer galK_gD223_R
SEQ ID NO: 39: Primer gD213-scFvHER2f
SEQ ID NO: 40: Primer gD224-scFvHER2r
SEQ ID NO: 41: Primer gDintforw
SEQ ID NO: 42: Primer gD24-scFvHer2-F
SEQ ID NO: 43: Primer gD25-scFvHer2-R
SEQ ID NO: 44: Primer gD213-GCN4-F
SEQ ID NO: 45: Primer gD224-GCN4-R
SEQ ID NO: 46: Primer HSV 139688 r
SEQ ID NO: 47: primer gD35-galK-F
SEQ ID NO: 48: primer gD39-galK-R
SEQ ID NO: 49: primer gD35-GCN4-F
SEQ ID NO: 50: primer gD39-GCN4-R
SEQ ID NO: 51: primer scFv4D5 651_f
SEQ ID NO: 52: primer gDintrev
SEQ ID NO: 53: primer gD219-GCN4-F

EXAMPLES

Example 1

Construction of HSV recombinants R-87, R-89, R-97, R-99, R-99-2
expressing genetically modified forms of gD, carrying (i) a GCN4 peptide inserted between AA 24 and 25 of gD (R-87 and R-89), or in place of AA 35-39 (R-97), or in place of AA 214-223 (R-99), or in place of AA 219-223 (R-99-2); (ii) a deletion of gD encompassing AA 35-39 (R-87), a deletion of gD encompassing AA 214-223 (R-89, and R-99), a deletion of gD encompassing AA 219-223 (R-99-2); (iii) the replacement of AA 35-39 deleted sequences (R-87) and the replacement of AA 214-223 deleted sequences (R-89) with scFv to HER2; (iv) an scFv to HER2 inserted between AA 24 and 25 of gD (R-97, R-99 and R-99-2).

A) As a preliminary step to the engineering of R-87 and R-89, the invertors constructed R-81, carrying the insertion of GCN4 peptide between AA 24 and 25 of HSV gD.

The inventors engineered R-81 by insertion of the sequence encoding the GCN4 peptide between AA 24 and 25 of mature gD, corresponding to AA 49 and 50 of precursor gD, prior to cleavage of the signal sequence, which encompasses AA 1 to 25.

The starting genome was the BAC LM55, which carries LOX-P-bracketed pBeloBAC11 and eGFP sequences inserted between $U_L3$ and $U_L4$ of HSV-1 genome (Menotti et al., 2008). The engineering was performed by means of galK recombineering. Briefly, in order to insert the GCN4 peptide in gD, the galK cassette with homology arms to gD was amplified by means of primers gD24_galK_f CTCT-CAAGATGGCCGACCCCAATCGCTTTCGCGGCAAA-GACCTTCCGGTCCCT GTTGACAATTAAT-CATCGGCA (SEQ ID NO: 20) and gD25_galK_r TGGATGTGGTACACGCGCCGGACCCCCG-GAGGGTCGGTCAGCTGGTCCAGTC AGCACTGTCCTGCTCCTT (SEQ ID NO: 21) using pGalK as template. This cassette was electroporated in SW102 bacteria carrying the BAC LM55 BG. The recombinant clones carrying the galK cassette were selected on plates containing M63 medium (15 mM $(NH_4)_2SO_4$, 100 mM $KH_2PO_4$, 1.8 μg $FeSO_4.H_2O$, adjusted to pH7) supplemented with 1 mg/L D-biotin, 0.2% galactose, 45 mg/L L-leucine, 1 mM $MgSO_4.7H_2O$ and 12 μg/ml chloramphenicol. In order to exclude galK false positive bacterial colonies, they were streaked also on MacConkey agar base plates supplemented with 1% galactose and 12 μg/ml chloramphenicol and checked by colony PCR with primer galK_827_f GCGTGATGTCACCATTGAAG (SEQ ID NO: 22) and galK_1142_r TATTGTTCAGCGACAGCTTG (SEQ ID NO: 23). Next, the GCN4 peptide cassette (SEQ ID NO: 24, encoding SEQ ID NO: 12) with the downstream and upstream Ser-Gly linkers and bracketed by homology arms to gD was generated through the annealing and extension of primers gD24_GCN4 JB CTCTCAAGATGGCCGACCC-CAATCGCTTTCGCGGCAAAGACCTTCCGGTCGGA TCCAAGAACTACCACCTGGAGAACGAGGTGGCCA-GACTGAAGAAGCTGGTGGG CAGC (SEQ ID NO: 25) and gD25_GCN4_rB TGGATGTGGTA-CACGCGCCGGACCCCCG-GAGGGTCGGTCAGCTGGTCCAGGC TGCC-CACCAGCTTCTTCAGTCTGGCCACCTCGTTCT-CCAGGTGGTAGTTCTTGG ATCC (SEQ ID NO: 26) which introduce a silent restriction site for the BamHI endonuclease, useful for screening of colonies by means of restriction analysis. The recombinant genome (SEQ ID NO: 27) encodes the chimeric gD (SEQ ID NO: 28), which carries the GCN4 peptide including one downstream and one upstream Ser-Gly linker with the sequence GS. The recombinant clones carrying the excision of the galK cassette and the insertion of the sequence of choice, GCN4 peptide, were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 μg/ml chloramphenicol. Bacterial colonies were checked for the presence of sequence of choice by means of colony PCR with primers gD_ext_f TCCATACCGACCACACCGACGAATCCC (SEQ ID NO: 29) and gD_ext_r GAGTTTGATACCAGACTGACCGTG (SEQ ID NO: 30).

B) R-87

Insertion of GCN4 peptide between AA 24 and 25 of HSV gD, deletion of AA 35-39, replaced by scFv to HER2 receptor.

The inventors engineered R-87 (FIG. 1) by insertion of the sequence encoding the GCN4 peptide between AA 24 and 25 of mature gD, corresponding to AA 49 and 50 of precursor gD, prior to cleavage of the signal sequence, which encompasses AA 1-25, and by deletion of AA 35-39, replaced by scFv.

The starting genome was the BAC 81, which carries GCN4 peptide between AA 24 and 25 of HSV gD, LOX-P-bracketed pBeloBAC11 and EGFP sequences inserted between $U_L3$ and $U_L4$ of HSV-1 genome, as described above. The engineering was performed by means of galK recombineering. Briefly, in order to insert the scFv in gD Δ AA 35-39, the galK cassette with homology arms to gD was amplified by means of primers galK_gD35_F TGAAGAAGCTGGTGGGCAGCCTGGACCAGCT-GACCGACCCTCCGGGGGTCCC TGTTGACAATTAAT-CATCGGCA (SEQ ID NO: 31) and galK_gD39_R GTGATCGGGAGGCTGGGGGGCTG-GAACGGGTCTGGTAGGCCCGCCTGGATTC AGCACTGTCCTGCTCCTT (SEQ ID NO: 32) using pGalK as template. This cassette was electroporated in SW102 bacteria carrying the BAC 81 BG. The recombinant clones carrying the galK cassette were selected on plates containing M63 medium (15 mM $(NH_4)_2SO_4$, 100 mM $KH_2PO_4$, 1.8 μg $FeSO_4.H_2O$, adjusted to pH7) supplemented with 1 mg/L D-biotin, 0.2% galactose, 45 mg/L L-leucine, 1 mM $MgSO_4.7H_2O$ and 12 μg/ml chloramphenicol. In order to exclude galK false positive bacterial colonies, they were streaked also on MacConkey agar base plates supplemented with 1% galactose and 12 μg/ml chloramphenicol and checked by colony PCR with primer galK_827_f GCGTGATGTCACCATTGAAG (SEQ ID NO: 22) and galK_1142_r TATTGTTCAGCGACAGCTTG (SEQ ID NO: 23). Next, the scFv HER2 cassette (SEQ ID NO: 33, encoding SEQ ID NO: 16) bracketed by homology arms to gD was amplified by means of primers gD-34-scFvHER2-F TGAAGAAGCTGGTGGGCAGCCTGGACC-AGCTGACCGACCCTCCGGGGGTCGA GAATTCCGA-TATCCAGAT (SEQ ID NO: 34) and gD-40-scFvHER2-R GTGATCGGGAGGCTGGGGGGCTG-GAACGGGTCTGGTAGGCCCGCCTGGATGG ATC-CACCGGAACCAGAGC (SEQ ID NO: 35). The recombinant genome (SEQ ID NO: 2) encodes the chimeric gD (SEQ ID NO: 3), which carries the GCN4 peptide including one downstream and one upstream Ser-Gly linker with the sequence GS in position 24 to 25 and the scFv to HER2 receptor in replacement of AA 35 to 39. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM MgSO$_4$.7H$_2$O and 12 μg/ml chloramphenicol. Bacterial colonies were checked for the presence of sequence of choice by means of colony PCR with primers gD_ext_f TCCATACCGACCACACCGACGAATCCC (SEQ ID NO: 29) and scFv_456_r AGCTGCACAGGACAAACGGAGTGAGCCCCC (SEQ ID NO: 36).

To reconstitute the recombinant virus R-87, 500 ng of recombinant BAC DNA was transfected into the Vero-GCN4R cell line and SK-OV-3 cell line by means of Lipofectamine 2000 (Life Technologies), and then grown in these cells. Virus growth was monitored by green fluorescence. The structure of the recombinants was verified by sequencing the entire gD. Virus stocks were generated in Vero-GCN4R cells and titrated in Vero-GCN4R and SK-OV-3.

C) R-89

Insertion of GCN4 peptide between AA 24 and 25 of HSV gD, deletion of AA 214 to 223, replaced by scFv to HER2 receptor.

The inventors engineered R-89 (FIG. 1) by insertion of the sequence encoding the GCN4 peptide between AA 24 and 25 of mature gD, corresponding to AA 49 and 50 of precursor gD, prior to cleavage of the signal sequence, which encompasses AA 1-25, and by deletion of AA 214-223, replaced by scFv to HER2.

The starting genome was the BAC 81, which carries GCN4 peptide between AA 24 and 25 of HSV gD, LOX-P-bracketed pBeloBAC11 and EGFP sequences inserted between U$_L$3 and U$_L$4 of HSV-1 genome, as described above. The engineering was performed by means of galK recombineering. Briefly, in order to insert the scFv in gD ΔAA 214-223, the galK cassette with homology arms to gD was amplified by means of primers galK_gD214_F CCTACCAGCAGGGGGTGACGGTGGACAGCATCGG-GATGCTGCCCCGCTTCCC TGTTGACAATTAAT-CATCGGCA (SEQ ID NO: 37) and galK_gD223_R CTCGTGTATGGGGCCTTGGGCCCGTGCCACCCGGC-GATCTTCAAGCTGTATCA GCACTGTCCTGCTCCTT (SEQ ID NO: 38) using pGalK as template. This cassette was electroporated in SW102 bacteria carrying the BAC 81 BG. The recombinant clones carrying the galK cassette were selected on plates containing M63 medium (15 mM (NH$_4$)$_2$SO$_4$, 100 mM KH$_2$PO$_4$, 1.8 μg FeSO$_4$.H$_2$O, adjusted to pH7) supplemented with 1 mg/L D-biotin, 0.2% galactose, 45 mg/L L-leucine, 1 mM MgSO$_4$.7H$_2$O and 12 μg/ml chloramphenicol. In order to exclude galK false positive bacterial colonies, they were streaked also on MacConkey agar base plates supplemented with 1% galactose and 12 μg/ml chloramphenicol and checked by colony PCR with primer galK_827_f GCGTGATGTCACCATTGAAG (SEQ ID NO: 22) and galK_1142_r TAT-TGTTCAGCGACAGCTTG (SEQ ID NO: 23). Next, the scFv HER2 cassette (SEQ ID NO: 33, encoding SEQ ID NO: 16) bracketed by homology arms to gD was amplified by means of primers gD213-scFvHER2f CCTACCAGCAGGGGGTGACGGTGGACAGCATCGG-GATGCTGCCCCGCTTCGA GAATTCCGATATCCAGAT (SEQ ID NO: 39) and gD224-scFvHER2r CTCGTGTATGGGGCCTTGGGCCCGTGCCACCCGGC-GATCTTCAAGCTGTAGGA TCCACCGGAACCAGAGC (SEQ ID NO: 40). The recombinant genome (SEQ ID NO: 4) encodes the chimeric gD (SEQ ID NO: 5), which carries the GCN4 peptide including one downstream and one upstream Ser-Gly linker with the sequence GS between positions 24 to 25 and the scFv to HER2 receptor in replacement of AA 214 to 223. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM MgSO$_4$.7H$_2$O and 12 μg/ml chloramphenicol. Bacterial colonies were checked for the presence of sequence of choice by means of colony PCR with primers gDintforw CCCTACAACCTGACCATCGCTTGG (SEQ ID NO: 41) and scFv_456_r AGCTGCACAGGACAAACGGAGTGAGCCCCC (SEQ ID NO: 36).

To reconstitute the recombinant virus R-89, 500 ng of recombinant BAC DNA was transfected into the Vero-GCN4R cell line and SK-OV-3 cell line by means of Lipofectamine 2000 (Life Technologies), and then grown in these cells. Virus growth was monitored by green fluorescence. The structure of the recombinants was verified by sequencing the entire gD. Virus stocks were generated in Vero-GCN4R cells and titrated in Vero-GCN4R and SK-OV-3.

D) R-97

Insertion of scFv to HER2 receptor between AA 24 and 25 of HSV gD, deletion of AA 35-39, replaced by GCN4 peptide.

The inventors engineered R-97 (FIG. 1) by insertion of the sequence encoding the scFv to HER2 receptor between AA 24 and 25 of mature gD, corresponding to AA 49 and 50 of precursor gD, prior to cleavage of the signal sequence, which encompasses AA 1-25, and by deletion of AA 35-39, replaced by GCN4 peptide.

The starting genome was the BAC LM55, which carries LOX-P-bracketed pBeloBAC11 and EGFP sequences inserted between U$_L$3 and U$_L$4 of HSV-1 genome (Menotti et al., 2008). The engineering was performed by means of galK recombineering. Briefly, in order to insert the scFv in gD, the galK cassette was inserted between AA 24 and 25, as described above in R-81. Next, the scFv HER2 cassette (SEQ ID NO: 33, encoding SEQ ID NO: 16) bracketed by homology arms to gD was amplified by means of primers gD24-scFvHer2-F CTCTCAAGATGGCCGACCC-CAATCGCTTTCGCGGCAAAGACCTTCCGGTCGAG AATTCCGATATCCAGATG (SEQ ID NO: 42) and gD25-scFvHer2-R TGGATGTGGTA- CACGCGCCGGACCCCCG-
GAGGGTCGGTCAGCTGGTCCAGGG
ATCCACCGGAACCAGAGC (SEQ ID NO: 43). The recombinant genome (BAC 91) encodes the chimeric gD, which carries the scFv to HER2 receptor between AA 24 to 25. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 µg/ml chloramphenicol. Bacterial colonies were checked for the presence of sequence of choice by means of colony PCR with primers gD_ext_f TCCATACCGACCACACCGACGAATCCC (SEQ ID NO: 29) and scFv_456_r AGCTGCACAGGACAAACGGAGT-GAGCCCCC (SEQ ID NO: 36).

Then, in order to insert the GCN4 peptide in gD Δ AA 35-39, the galK cassette with homology arms to gD was amplified by means of primers gD35-galK-F GCTCTGGTTCCGGTg-
GaTCCCTGGACCAGCTGACCGACCCTCCGGGGG-TCCCT GTTGACAATTAATCATCGGCA (SEQ ID NO: 47) and gD39-galK-R GTGATCGG-GAGGCTGGGGGGCTG-
GAACGGGTCTGGTAGGCCCGCCTGGATTC AGCACTGTCCTGCTCCTT (SEQ ID NO: 48) using pGalK as template. This cassette was electroporated in SW102 bacteria carrying the BAC 91 BG. The recombinant clones carrying the galK cassette were selected on plates containing M63 medium (15 mM $(NH_4)_2SO_4$, 100 mM $KH_2PO_4$, 1.8 µg $FeSO_4.H_2O$, adjusted to pH7) supplemented with 1 mg/L D-biotin, 0.2% galactose, 45 mg/L L-leucine, 1 mM $MgSO_4.7H_2O$ and 12 µg/ml chloramphenicol. In order to exclude galK false positive bacterial colonies, they were streaked also on MacConkey agar base plates supplemented with 1% galactose and 12 µg/ml chloramphenicol and checked by colony PCR with primer galK_827_f GCGTGATGTCACCATTGAAG (SEQ ID NO: 22) and galK_1142_r TATTGTTCAGCGACAGCTTG (SEQ ID NO: 23). Next, the GCN4 peptide cassette (SEQ ID NO: 24, encoding SEQ ID NO: 12) with the downstream and upstream Ser-Gly linkers bracketed by homology arms to gD was amplified by means of primers gD35-GCN4-F GCTCTGGTTCCGGTg-
GaTCCCTGGACCAGCTGACCGACCCTCCGGGGGTCG-GA TCCAAGAACTACCACCTG-
GAGAACGAGGTGGCCAGACTGAAGAAGCTGGTGGG CAGC (SEQ ID NO: 49) and gD39-GCN4-R GTGATCGG-GAGGCTGGGGGGCTG-
GAACGGGTCTGGTAGGCCCGCCTGGATGC TGCC-CACCAGCTTCTTCAGTCTGGCCACCTCGTTCTCC-AGGTGGTAGTTCTTGG ATCC (SEQ ID NO: 50). The recombinant genome (SEQ ID NO: 6) encodes the chimeric gD (SEQ ID NO: 7), which carries the scFv to HER2 receptor between AA 24 to 25 and the GCN4 peptide including one downstream and one upstream Ser-Gly linker with the sequence GS in replacement of AA 35 to 39. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 µg/ml chloramphenicol. Bacterial colonies were checked for the presence of sequence of choice by means of colony PCR with primers scFv4D5 651_f GGACACTGCCGTCTATTATTGTAGCCGCT (SEQ ID NO: 51) and primer gDintrev CCAGTCGTTTATCTT-CACGAGCCG (SEQ ID NO: 52). To reconstitute the recombinant virus R-97, 500 ng of recombinant BAC DNA was transfected into the Vero-GCN4R cell line and SK-OV-3 cell line by means of Lipofectamine 2000 (Life Technologies), and then grown in these cells. Virus growth was monitored by green fluorescence. The structure of the recombinants was verified by sequencing the entire gD.

E) R-99

Insertion of scFv to HER2 receptor between AA 24 and 25 of HSV gD, deletion of AA 214-223, replaced by GCN4 peptide.

The inventors engineered R-99 (FIG. 1) by insertion of the sequence encoding the scFv to HER2 receptor between AA 24 and 25 of mature gD, corresponding to AA 49 and 50 of precursor gD, prior to cleavage of the signal sequence, which encompasses AA 1-25, and by deletion of AA 214-223, replaced by GCN4 peptide.

The starting genome was the BAC 91, which carries the scFv to HER2 receptor between AA 24 to 25 of gD, LOX-P-bracketed pBeloBAC11 and EGFP sequences inserted between $U_L3$ and $U_L4$ of HSV-1 genome, whose construction was described above. In order to insert the GCN4 peptide in gD Δ AA 214-223, the galK cassette with homology arms to gD was amplified by means of primers galK_gD214_F CCTACCAGCAGGGGGTGACGGTGGACAGCATCGG-GATGCTGCCCCGCTTCCC TGTTGACAATTAAT-CATCGGCA (SEQ ID NO: 37) and galK_gD223_R CTCGTGTATGGGGCCTTGGGCCCGTGCCACCCGGC-GATCTTCAAGCTGTATCA GCACTGTCCTGCTCCTT (SEQ ID NO: 38) using pGalK as template. This cassette was electroporated in SW102 bacteria carrying the BAC 91 BG. The recombinant clones carrying the galK cassette were selected on plates containing M63 medium (15 mM $(NH_4)_2SO_4$, 100 mM $KH_2PO_4$, 1.8 µg $FeSO_4.H_2O$, adjusted to pH7) supplemented with 1 mg/L D-biotin, 0.2% galactose, 45 mg/L L-leucine, 1 mM $MgSO_4.7H_2O$ and 12 µg/ml chloramphenicol. In order to exclude galK false positive bacterial colonies, they were streaked also on MacConkey agar base plates supplemented with 1% galactose and 12 µg/ml chloramphenicol and checked by colony PCR with primer galK_827_f GCGTGATGTCACCATTGAAG (SEQ ID NO: 22) and galK_1142_r TAT-TGTTCAGCGACAGCTTG (SEQ ID NO: 23). Next, the GCN4 peptide cassette (SEQ ID NO: 24, encoding SEQ ID NO: 12) with the downstream and upstream Ser-Gly linkers bracketed by homology arms to gD was amplified by means of primers gD213-GCN4-F CCTACCAGCAGGGGGTGACGGTGGACAGCATCGG-GATGCTGCCCCGCTTCGG ATCCAAGAACTAC-CACCTGGAGAACGAGGTGGCCAGACT-GAAGAAGCTGGTGG GCAGC (SEQ ID NO: 44) and gD224-GCN4-R
CTCGTGTATGGGGCCTTGGGCCCGTGCCACCCGGC-GATCTTCAAGCTGTAGCT GCC-CACCAGCTTCTTCAGTCTGGC-
CACCTCGTTCTCCAGGTGGTAGTTCTTGGA TCC (SEQ ID NO: 45). The recombinant genome (SEQ ID NO: 8) encodes the chimeric gD (SEQ ID NO: 9), which carries the scFv to HER2 receptor between AA 24 to 25 and the GCN4 peptide including one downstream and one upstream Ser-Gly linker with the sequence GS in replacement of AA 214 to 223. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 µg/ml chloramphenicol. Bacterial colonies were checked for the presence of sequence of choice by means of colony PCR with primers gDintforw CCCTACAACCTGACCATCGCTTGG (SEQ ID NO: 41) and HSV_139688_r CCGACTTATCGACTGTCCACCTTTCCC (SEQ ID NO: 46).

To reconstitute the recombinant virus R-99, 500 ng of recombinant BAC DNA was transfected into the Vero-GCN4R cell line and SK-OV-3 cell line by means of Lipofectamine 2000 (Life Technologies), and then grown in these cells. Virus growth was monitored by green fluorescence. The structure of the recombinants was verified by sequencing the entire gD. Virus stocks were generated in Vero-GCN4R cells and titrated in Vero-GCN4R and SK-OV-3.

F) R-99-2

Insertion of scFv to HER2 receptor between AA 24 and 25 of HSV gD, deletion of AA 219-223, replaced by GCN4 peptide.

The inventors engineered R-99-2 (FIG. 1) by insertion of the sequence encoding the scFv to HER2 receptor between AA 24 and 25 of mature gD, corresponding to AA 49 and 50 of precursor gD, prior to cleavage of the signal sequence, which encompasses AA 1-25, and by deletion of AA 219-223, replaced by GCN4 peptide.

The starting genome was the BAC 91, which carries the scFv to HER2 receptor between AA 24 to 25 of gD, LOX-P-bracketed pBeloBAC11 and EGFP sequences inserted between $U_L3$ and $U_L4$ of HSV-1 genome, whose construction was described above. In order to insert the GCN4 peptide in gD Δ AA 219-223, the galK cassette with homology arms to gD was amplified by means of primers galK_gD214_F CCTACCAGCAGGGGGTGACGGTGGACAGCATCGGGATGCTGCCCCGCTTCCC TGTTGACAATTAATCATCGGCA (SEQ ID NO: 37) and galK_gD223_R CTCGTGTATGGGGCCTTGGGCCCGTGCCACCCGGCGATCTTCAAGCTGTATCA GCACTGTCCTGCTCCTT (SEQ ID NO: 38) using pGalK as template. This cassette was electroporated in SW102 bacteria carrying the BAC 91 BG. The recombinant clones carrying the galK cassette were selected on plates containing M63 medium (15 mM (NH$_4$)$_2$SO$_4$, 100 mM KH$_2$PO$_4$, 1.8 μg FeSO$_4$.H$_2$O, adjusted to pH7) supplemented with 1 mg/L D-biotin, 0.2% galactose, 45 mg/L L-leucine, 1 mM MgSO$_4$.7H$_2$O and 12 μg/ml chloramphenicol. In order to exclude galK false positive bacterial colonies, they were streaked also on MacConkey agar base plates supplemented with 1% galactose and 12 μg/ml chloramphenicol and checked by colony PCR with primer galK_827_f GCGTGATGTCACCATTGAAG (SEQ ID NO: 22) and galK_1142_r TATTGTTCAGCGACAGCTTG (SEQ ID NO: 23). Next, the GCN4 peptide cassette (SEQ ID NO: 24, encoding SEQ ID NO: 12) with the downstream and upstream Ser-Gly linkers bracketed by homology arms to gD was amplified by means of primers gD219-GCN4-F CCTACCAGCAGGGGGTGACGGTGGACAGCATCGGGATGCTGCCCCGCTTCATC CCCGAGAACCAGCGCGGATCCAAGAACTACCACCTGGAGAACGAGGTGGCCA GACTGAAGAAGCTGG (SEQ ID NO: 53) and gD224-GCN4-R CTCGTGTATGGGGCCTTGGGCCCGTGCCACCCGGCGATCTTCAAGCTGTAGCT GCCCACCAGCTTCTTCAGTCTGGCCACCTCGTTCTCCAGGTGGTAGTTCTTGGA TCC (SEQ ID NO: 45). The recombinant genome (SEQ ID NO: 10) encodes the chimeric gD (SEQ ID NO: 11), which carries the scFv to HER2 receptor between AA 24 to 25 and the GCN4 peptide including one downstream and one upstream Ser-Gly linker with the sequence GS in replacement of AA 219 to 223. The recombinant clones carrying the excision of the galK cassette and the insertion of the sequence of choice were selected on plates containing M63 medium (see above) supplemented with 1 mg/L D-biotin, 0.2% deoxy-2-galactose, 0.2% glycerol, 45 mg/L L-leucine, 1 mM MgSO$_4$.7H$_2$O and 12 μg/ml chloramphenicol. Bacterial colonies were checked for the presence of sequence of choice by means of colony PCR with primers gDintforw CCCTACAACCTGACCATCGCTTGG (SEQ ID NO: 41) and HSV_139688_r CCGACTTATCGACTGTCCACCTTTCCC (SEQ ID NO: 46)

To reconstitute the recombinant virus R-99-2, 500 ng of recombinant BAC DNA was transfected into the Vero-GCN4R cell line and SK-OV-3 cell line by means of Lipofectamine 2000 (Life Technologies), and then grown in these cells. Virus growth was monitored by green fluorescence. The structure of the recombinants was verified by sequencing the entire gD.

Example 2. Double Tropism of R-87 for Vero-GCN4R and for the HER-2 Positive SK-OV-3 and J-HER2 Cells It has previously been shown that the insertion of scFv-HER2 in gD confers to the recombinant virus R-LM113 the ability to enter cells through the HER2 receptor, and that R-LM113 is detargeted from the natural gD receptors nectin-1 and HVEM, because of the deletion of the gD region between AA 6-38.

Figure 2:
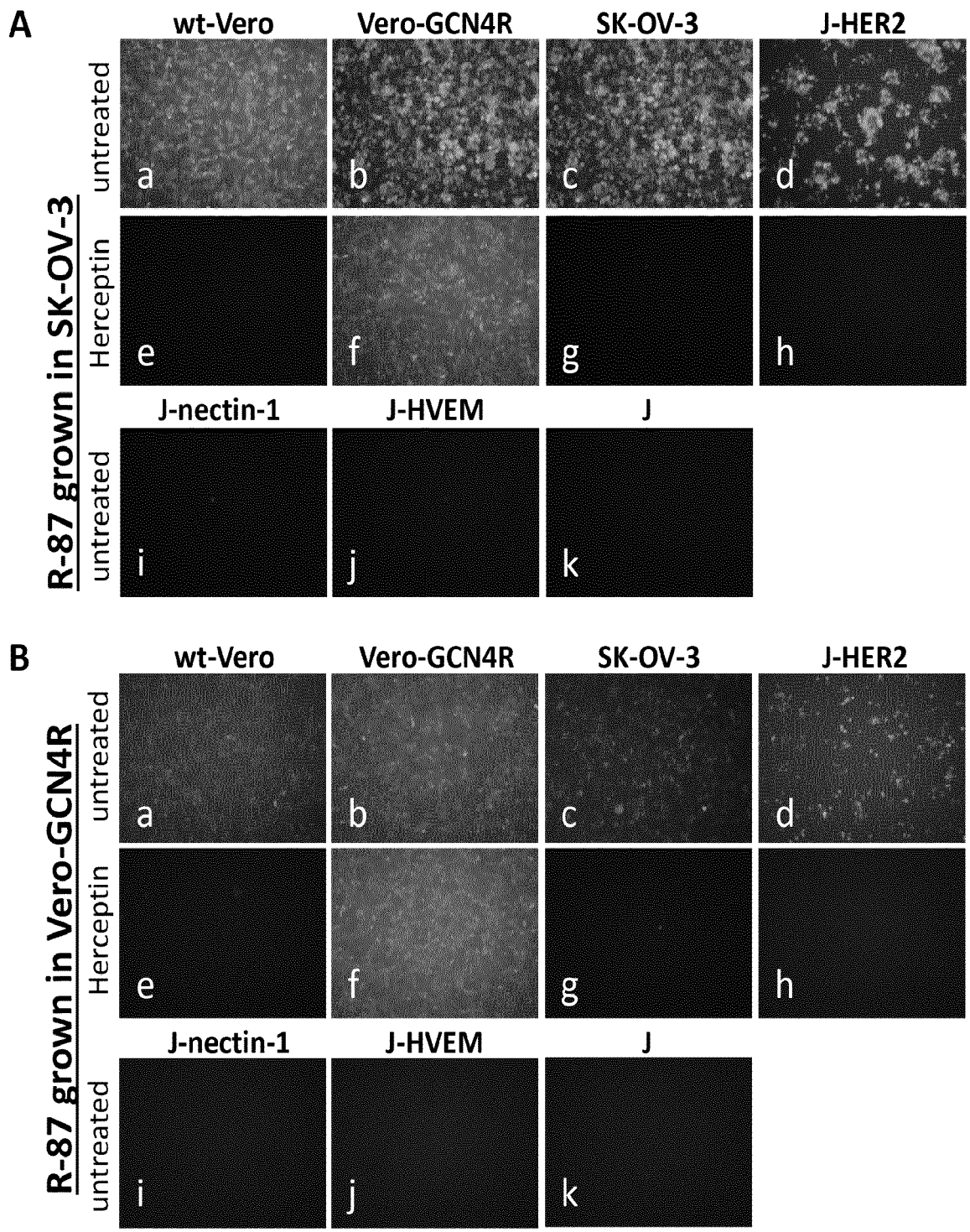

To verify whether the insertion of the GCN4 peptide between AA 24 and 25 of gD enables R-87 to infect the Vero-GCN4R cells, the inventors made use of Vero-GCN4R cell line and, for comparison, its wt counterpart, wt-Vero. To verify that R-87 is able to infect through the HER2 receptor, the inventors made use of the J-HER2 cells, which express HER2 as the sole receptor, and of the HER2-positive cancer cells, SK-OV-3 cells. To verify that R-87 is detargeted from nectin-1 and HVEM, the inventors made use of J-nectin-1 and J-HVEM, which express only the indicated receptor. Cells were infected with R-87 grown in SK-OV-3 (FIG. 2 A) or in Vero-GCN4R (FIG. 2 B) cells. Where indicated, infection was carried out in the presence of MAb to HER2, named Herceptin, at the concentration of 28 μg/ml. Infection was carried out at 1 PFU/cell, and was monitored 24 hours later by fluorescence microscopy. As shown in FIGS. 2 A and B, R-87 infected Vero-GCN4R, J-HER2, and SK-OV-3 cells. R-87 also infected the wt-Vero cells, as expected given that these cells express the simian ortholog of HER-2. Infection of J-HER2, SK-OV-3, wt-Vero was inhibited by Herceptin, indicating that it occurred through HER2. By contrast infection of Vero-GCN4R was not inhibited by Herceptin, indicating that it occurred through the GCN4 peptide and not through HER2. The pattern of infection was undistinguishable whether the R-87 was grown in SK-OV-3 or Vero-GCN4R cells, clearly demonstrating that infection specificities of R-87 was not modified depending on whether it was grown in either one or the other cell line.

Figure 3:
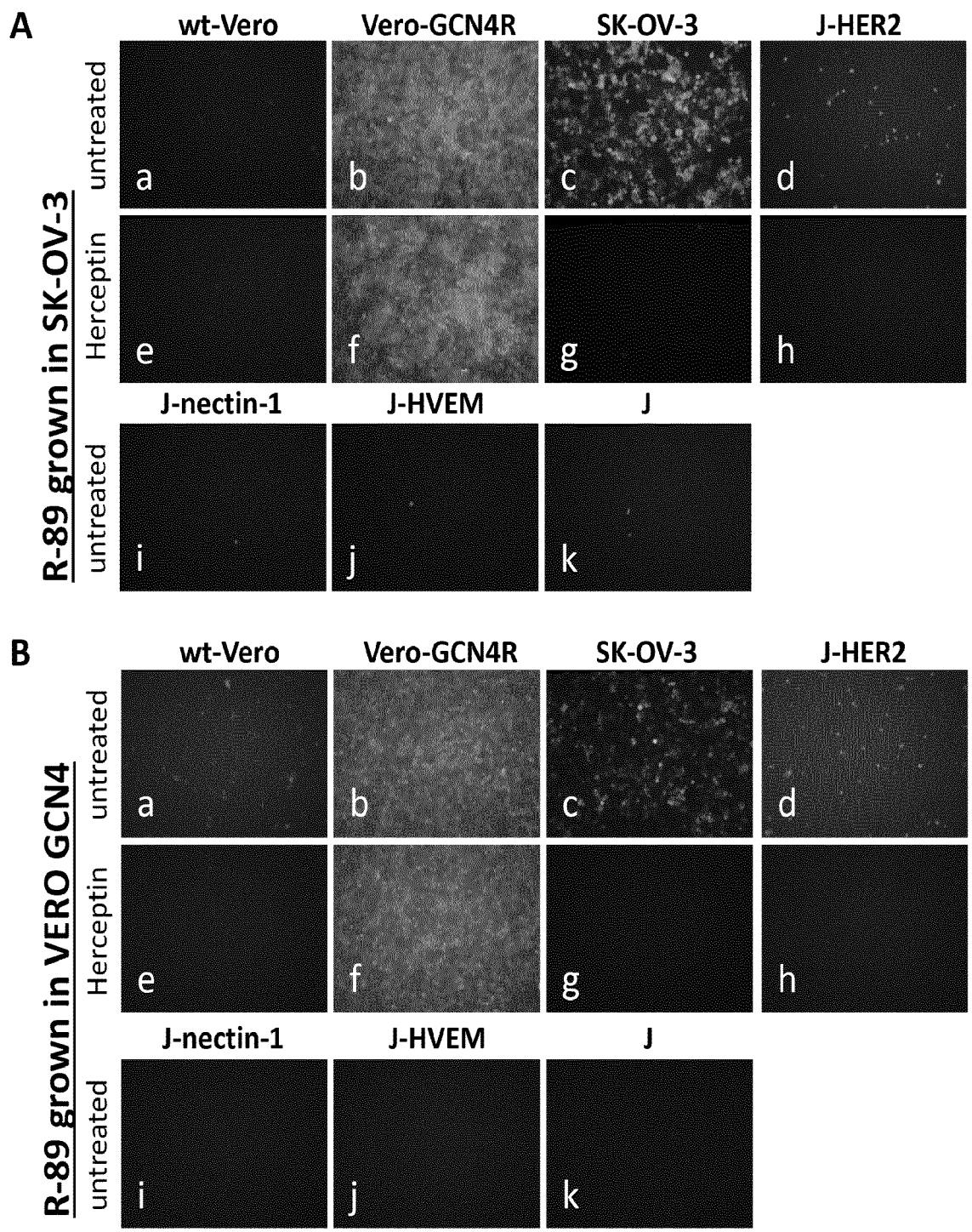
Figure 4:
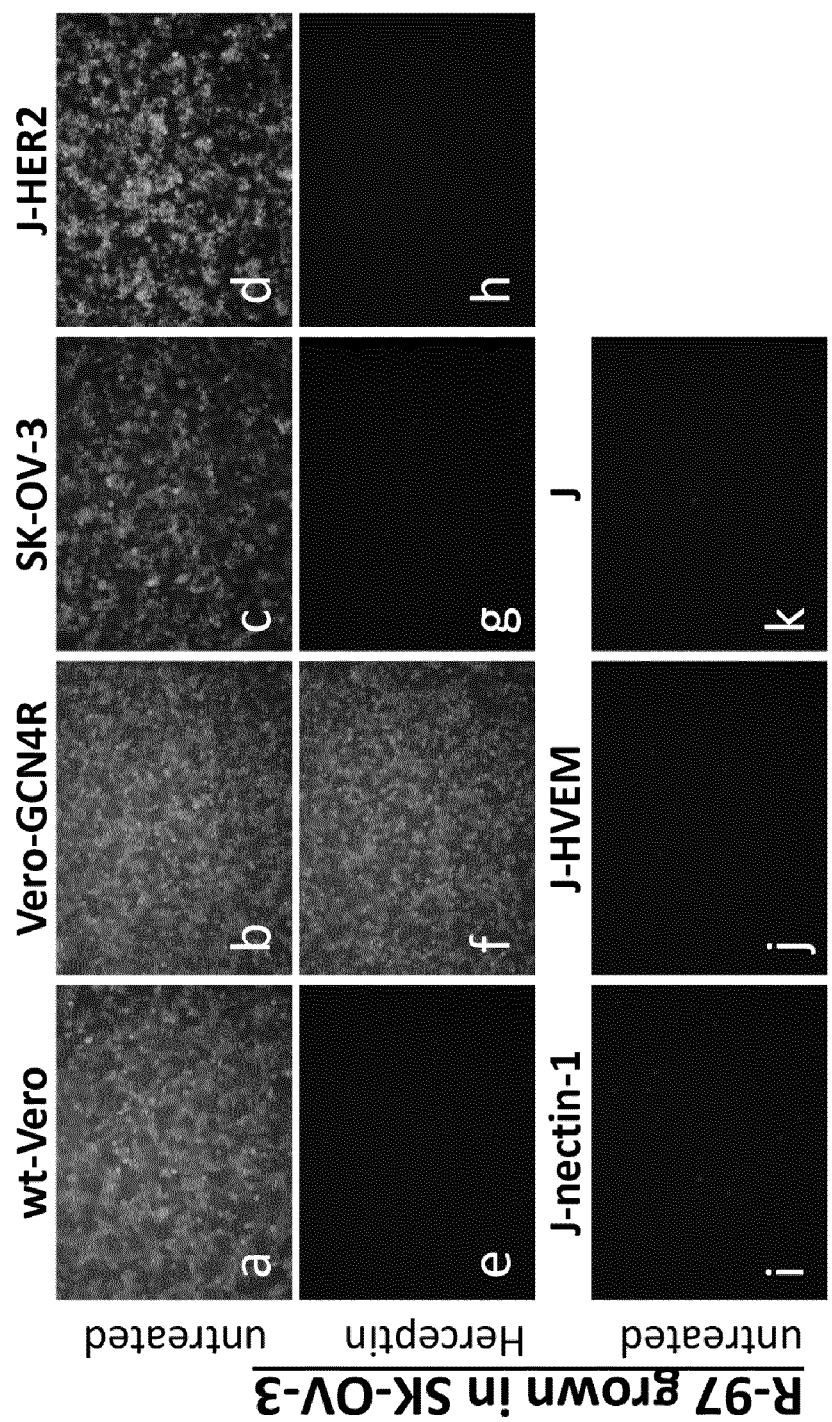
Figure 5:
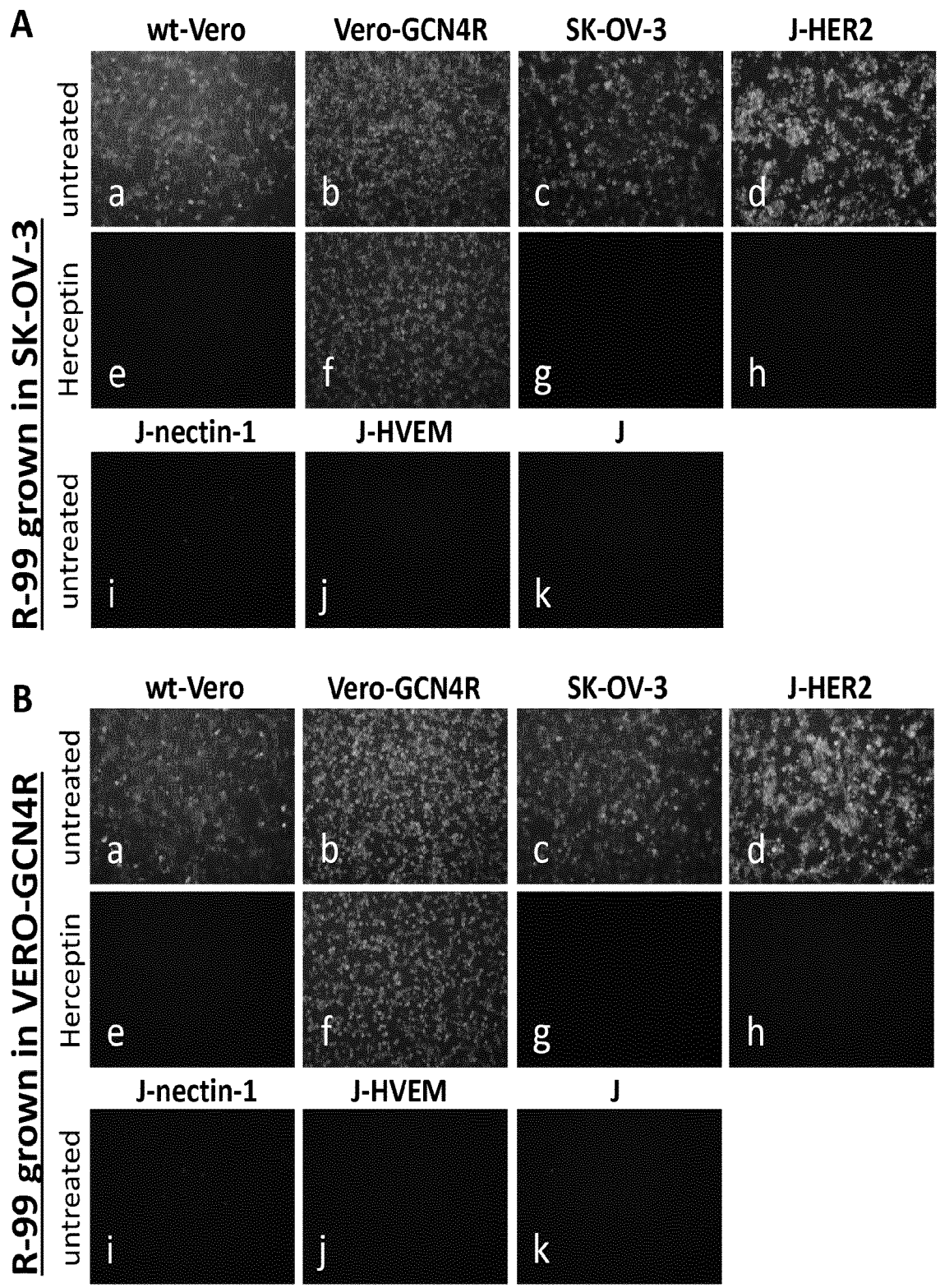
Figure 6:
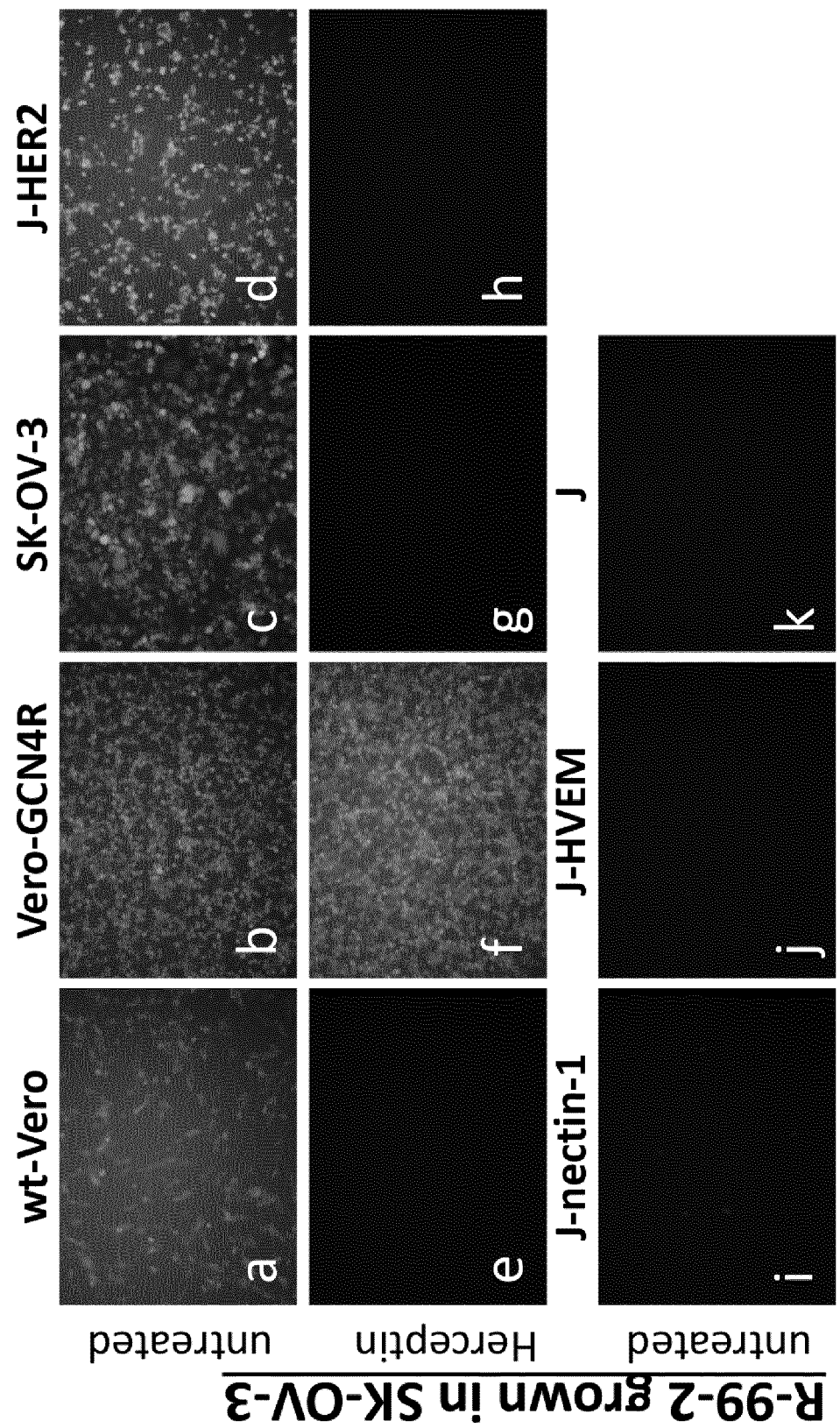

Example 3. Double Tropism of R-89 for Vero-GCN4R and for the HER-2 Positive SK-OV-3 and J-HER2 Cells To verify whether the insertion of the GCN4 peptide between AA 24 and 25 of gD enables R-89 to infect the Vero-GCN4R cells, the inventors made use of Vero-GCN4R cell line and, for comparison, its wt counterpart, wt-Vero. To verify that R-89 is able to infect through the HER2 receptor, the inventors made use of the J-HER2 cells, which express HER2 as the sole receptor, and of the HER2-positive cancer cells, SK-OV-3 cells. To verify that R-89 is detargeted from nectin-1 and HVEM, the inventors made use of J-nectin-1 and J-HVEM, which express only the indicated receptor. Cells were infected with R-89 grown in SK-OV-3 (FIG. 3 A) or in Vero-GCN4R (FIG. 3 B) cells. Where indicated, infection was carried out in the presence of MAb to HER2, named Herceptin, at the concentration of 28 µg/ml. Infection was carried out at 1 PFU/cell, and was monitored 24 hours later by fluorescence microscopy. As shown in FIGS. 3 A and B, R-89 infected Vero-GCN4R, J-HER2, and SK-OV-3 cells. R-89 infected poorly the wt-Vero cells and J-HER2. Infection of SK-OV-3, wt-Vero and J-HER2 was inhibited by Herceptin, indicating that it occurred through HER2. By contrast infection of Vero-GCN4R was not inhibited by Herceptin, indicating that it occurred through the GCN4 peptide and not through HER2. The pattern of infection was undistinguishable whether the R-89 was grown in SK-OV-3 or Vero-GCN4R cells, clearly demonstrating that infection specificities of R-89 was not modified depending on whether it was grown in either one or the other cell line.

Example 4. Double Tropism of R-97 for Vero-GCN4R and for the HER-2 Positive SK-OV-3 and J-HER2 Cells To verify whether the insertion of the GCN4 peptide instead of AA 35-39 of gD enables R-97 to infect the Vero-GCN4R cells, the inventors made use of Vero-GCN4R cell line and, for comparison, its wt counterpart, wt-Vero. To verify that R-97 is able to infect through the HER2 receptor, the inventors made use of the J-HER2 cells, which express HER2 as the sole receptor, and of the HER2-positive cancer cells, SK-OV-3 cells. To verify that R-97 is detargeted from nectin-1 and HVEM, the inventors made use of J-nectin-1 and J-HVEM, which express only the indicated receptor. Cells were infected with R-97 grown in SK-OV-3 cells. Where indicated, infection was carried out in the presence of MAb to HER2, named Herceptin, at the concentration of 28 μg/ml. Infection was carried out at 1 PFU/cell, and was monitored 24 hours later by fluorescence microscopy. As shown in FIG. 4, R-97 infected Vero-GCN4R, J-HER2, and SK-OV-3 cells. R-97 also infected the wt-Vero cells, as expected given that these cells express the simian ortholog of HER-2. Infection of J-HER2, SK-OV-3, wt-Vero was inhibited by Herceptin, indicating that it occurred through HER2. By contrast infection of Vero-GCN4R was not inhibited by Herceptin, indicating that it occurred through the GCN4 peptide and not through HER2.

Example 5. Double Tropism of R-99 for Vero-GCN4R and for the HER-2 Positive SK-OV-3 and J-HER2 Cells To verify whether the insertion of the GCN4 peptide instead of AA 214-223 of gD enables R-99 to infect the Vero-GCN4R cells, the inventors made use of Vero-GCN4R cell line and, for comparison, its wt counterpart, wt-Vero. To verify that R-99 is able to infect through the HER2 receptor, the inventors made use of the J-HER2 cells, which express HER2 as the sole receptor, and of the HER2-positive cancer cells, SK-OV-3 cells. To verify that R-99 is detargeted from nectin-1 and HVEM, the inventors made use of J-nectin-1 and J-HVEM, which express only the indicated receptor. Cells were infected with R-99 grown in SK-OV-3 (FIG. 5 A) or in Vero-GCN4R (FIG. 5 B) cells. Where indicated, infection was carried out in the presence of MAb to HER2, named Herceptin, at the concentration of 28 μg/ml. Infection was carried out at 1 PFU/cell, and was monitored 24 hours later by fluorescence microscopy. As shown in FIG. 5 A, R-99 infected Vero-GCN4R, J-HER2, and SK-OV-3 cells. R-99 also infected the wt-Vero cells, as expected given that these cells express the simian ortholog of HER-2. Infection of J-HER2, SK-OV-3, wt-Vero was inhibited by Herceptin, indicating that it occurred through HER2. By contrast infection of Vero-GCN4R was not inhibited by Herceptin, indicating that it occurred through the GCN4 peptide and not through HER2.

Example 6. Double Tropism of R-99-2 for Vero-GCN4R and for the HER-2 Positive SK-OV-3 and J-HER2 Cells To verify whether the insertion of the GCN4 peptide instead of AA 219-223 of gD enables R-99-2 to infect the Vero-GCN4R cells, the inventors made use of Vero-GCN4R cell line and, for comparison, its wt counterpart, wt-Vero. To verify that R-99-2 is able to infect through the HER2 receptor, the inventors made use of the J-HER2 cells, which express HER2 as the sole receptor, and of the HER2-positive cancer cells, SK-OV-3 cells. To verify that R-99-2 is detargeted from nectin-1 and HVEM, the inventors made use of J-nectin-1 and J-HVEM, which express only the indicated receptor. Cells were infected with R-99-2 grown in SK-OV-3 cells (FIG. 6). Where indicated, infection was carried out in the presence of MAb to HER2, named Herceptin, at the concentration of 28 μg/ml. Infection was carried out at 1 PFU/cell, and was monitored 24 hours later by fluorescence microscopy. As shown in FIG. 6, R-99-2 infected Vero-GCN4R, J-HER2, and SK-OV-3 cells. R-99-2 also infected the wt-Vero cells, as expected given that these cells express the simian ortholog of HER-2. Infection of J-HER2, SK-OV-3, wt-Vero was inhibited by Herceptin, indicating that it occurred through HER2. By contrast infection of Vero-GCN4R was not inhibited by Herceptin, indicating that it occurred through the GCN4 peptide and not through HER2.

Example 7. Extent of R-87, R-89, and R-99 Replication in SK-OV-3 (A) and in Vero-GCN4R (B) Cells, as Compared to that of the Recombinant R-LM113 which Carries the scFv to HER2 in gD, in Place of Deletion Between AA 6-38

The inventors compared the extent of replication of R-87, and R-89, R-99 to that of R-LM113 in SK-OV-3 (FIG. 7 A) or in Vero-GCN4R cells (FIG. 7 B). R-LM113 virus carries the scFv-HER2 inserted in gD in place of sequences 6-38 and does not carry the GCN4 peptide. SK-OV-3 (A) or Vero-GCN4R (B) cells were infected at MOI 0.1 PFU/cell, with the indicated viruses (inoculum titrated in the respective cell line), for 90 min at 37° C. Unabsorbed virus was inactivated by means of an acidic wash (40 mM citric acid, 10 mM KCl, 135 mM NaCl [pH 3]). Replicate cultures were frozen at the indicated times (24 and 48 h) after infection, and the progeny was titrated in SK-OV-3 cells. It can be seen from FIGS. 7 A and B that R-87 grew to similar titers as R-LM113. In contrast, R-89 grew about one-two log less than R-87 at 24 h. R-99 grew at intermediate levels.

The inventors measured the extent of progeny virus release to the extracellular medium of SK-OV-3 (C) or Vero-GCN4R (D) cells, infected at 0.1 PFU/cell as experiment shown in panels A and B, respectively. At 48 h after infection, replicate cultures were frozen as whole lysates plus medium (intra+extra). Alternatively, medium (extra) and cell-associated (intra) fractions were separated and frozen. Progeny virus was titrated in SK-OV-3 cells. It can be seen that the efficiency of progeny release in the extracellular medium was similar for all three viruses.

Example 8. Plating Efficiency of R-87, R-89, R-97, R-99 and R-99-2 in Different Cell Lines The inventors compared the ability of R-87, R-89, R-97, R-99 and R-99-2 to form plaques in different cell lines, with respect to plaque size (FIG. 8 A), and to number of plaques (FIG. 8 B). (A) Replicate aliquots of R-87, R-89, R-97, R-99 and R-99-2 were plated in Vero-GCN4R, wt-Vero, SK-OV-3 cells. Typical examples of relative plaque size of R-87, R-89, R-97, R-99 and R-99-2 in different cells are shown. By this parameter R-87 and R-89 exhibited the largest plaques size in Vero-GCN4R, as well as in SK-OV-3 cells. (B) Replicate aliquots of R-87, R-89, R-97, R-99 and R-99-2 were plated in Vero-GCN4R, wt-Vero, SK-OV-3 cells. The number of plaques was scored 3 days later. For each virus, the number of plaques scored in a given cell line was expressed relative to the number of plaques scored in SK-OV-3 cells, made equal to 100. It can be seen that R-87, R-89, R-97, R-99 and R-99-2 exhibited a high number of plaques in Vero-GCN4R cells.

Example 9

The SK-OV-3 (A) and Vero-GCN4R (B) were seeded in 96 well plates 8×10³ cells/well, and exposed to R-87, R-89, R-99, and R-LM113 for comparison, or mock-infected for 90 min at 37° C. The input multiplicity of infection (as titrated in the correspondent cell line) was 3 PFU/cell for the SK-OV-3 and Vero-GCN4R. Alamar-Blue (10 µl/well, Life Technologies) was added to the culture media at the indicated days after infection, and incubated for 4 h at 37° C. prior to plates reading. Plates were read at 560 and 600 nm with GloMax Discover System (Promega). For each time point, cell viability was expressed as the percentage of Alamar-Blue reduction in infected versus uninfected cells, excluding for each samples the contribution of medium alone. All viruses caused similar cytotoxicity to SK-OV-3 and to Vero-GCN4R cells, except for R-LM113 which was much less cytotoxic to Vero-GCN4R cells, in agreement with its lack of retargeting to this cell.

REFERENCES

Arndt K. and Fin G. R., PNAS 1986, 83, 8516-8520
Douglas J. T. et al., Nat Biotechnol, 1999, 17, 470-475
Florence G. et al., Virology: A Laboratory Manual, 1992, ISBN-13: 978-0121447304
Gatta V. et al., PLOS Pathogens, 2015, DOI: 10.1371/journal.ppat.1004907
Hope I. A and Struhl K., EMBO J, 1987, 6, 2781-2784
Josan J. S. et al., Bioconjug Chem, 2011, 22, 1270-1278;
Karlin S. and Altschul S. F., PNAS, 1990, 87, 2264-2268
Karlin S. and Altschul S. F., PNAS, 1993, 90, 5873-5877
Liu B. L. et al., Gene Ther, 2003, 10, 292-303
Menotti L et al. J Virol. 2008, 82, 10153-10161, DOI: 10.1128/JVI.01133-08. Epub 2008 Aug. 6
Nakamura T. et al., Nat Biotechnol, 2005, 23, 209-214. Epub 2005 Jan. 30
Needleman S. B. and Wunsch C. D., J Mol Biol, 1970, 48, 443-453
Pearson W. R. and Lipman D. J., PNAS, 1988, 85, 2444-2448
Peterson R. B. and Goyal S. M., Comp Immunol Microbiol Infect Dis. 1988, 11, 93-98
Shallal H. M. et al., Bioconjug Chem, 2014, 25, 393-405
Sandri-Goldin R. M. et al., Alpha Herpesviruses: Molecular and Cellular Biology, Caister Academic Press, 2006
Smith T. F. and Waterman M. S., Add APL Math, 1981, 2, 482-489
Uchida et al, Mol Ther 2013, 21, 561-569
Xhou G and Roizman, B, J Virol, 2005, 79, 5272-77
Xu L. et al., PNAS, 2012, 109, 21295-21300

SEQUENCE LISTING

<160> NUMBER OF SEQ ID NOS: 53

<210> SEQ ID NO 1
<211> LENGTH: 394
<212> TYPE: PRT
<213> ORGANISM: Herpes simplex virus 1

<400> SEQUENCE: 1

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95
```

```
Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Asp Pro Glu Asp Ser Ala Leu Leu
    290                 295                 300

Glu Asp Pro Val Gly Thr Val Ala Pro Gln Ile Pro Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390

<210> SEQ ID NO 2
<211> LENGTH: 2010
<212> TYPE: DNA
<213> ORGANISM: Artificial sequence
<220> FEATURE:
<223> OTHER INFORMATION: Nucleotide sequence of chimeric gD-GCN4, scFv
      HER2 of R-87

<400> SEQUENCE: 2 atggggggggg ctgccgccag gttgggggcc gtgattttgt tgtcgtcat agtgggcctc      60 catgggtcc gcggcaaata tgccttggcg gatgcctctc tcaagatggc cgaccccaat     120
cgctttcgcg gcaaagacct tccggtcgga tccaagaact accacctgga gaacgaggtg     180
gccagactga agaagctggt gggcagcctg accagctga ccgaccctcc ggggggtcgag     240 aattccgata tccagatgac ccagtccccg agctccctgt ccgcctctgt gggcgatagg     300
gtcaccatca cctgccgtgc cagtcaggat gtgaatactg ctgtagcctg gtatcaacag     360
```

```
aaaccaggaa aagctccgaa gcttctgatt tactcggcat ccttcctcta ctctggagtc    420
ccttctcgct tctctggtag ccgttccggg acggatttca ctctgaccat cagcagtctg    480
cagccggaag acttcgcaac ttattactgt cagcaacatt atactactcc tcccacgttc    540
ggacagggta ccaaggtgga gatcaaatcg gatatgccga tggctgatcc gaaccgtttc    600
cgcggtaaga acctggtttt tcattctgag gttcagctgg tggagtctgg cggtggcctg    660
gtgcagccag ggggctcact ccgtttgtcc tgtgcagctt ctggcttcaa cattaaagac    720
acctatatac actgggtgcg tcaggccccg gtaagggcc tggaatgggt tgcaaggatt    780
tatcctacga atggttatac tagatatgcc gatagcgtca agggccgttt cactataagc    840
gcagacacat ccaaaaacac agcctaccta caaatgaaca gcttaagagc tgaggacact    900
gccgtctatt attgtagccg ctggggaggg acggcttct atgctatgga ctactggggt    960
caaggaacac tagtcaccgt ctcctcgagt ggcggtggct ctggttccgg tggatccatc   1020
caggcgggcc taccagaccc gttccagccc ccagcctcc cgatcacggt ttactacgcc   1080
gtgttggagc gcgcctgccg cagcgtgctc ctaaacgcac cgtcggaggc cccccagatt   1140
gtccgcgggg cctccgaaga cgtccggaaa caaccctaca acctgaccat cgcttggttt   1200
cggatgggag gcaactgtgc tatccccatc acggtcatgg agtacaccga atgctcctac   1260
aacaagtctc tgggggcctg tcccatccga acgcagcccc gctggaacta ctatgacagc   1320
ttcagcgccg tcagcgagga taacctgggg ttcctgatgc acgccccgc gtttgagacc   1380 gccggcacgt acctgcggct cgtgaagata aacgactgga cggagattac acagtttatc   1440
ctggagcacc gagccaaggg ctcctgtaag tacgccctcc cgctgcgcat cccccgtca   1500 gcctgcctgt cccccaggc ctaccagcag ggggtgacgg tggacagcat cgggatgctg   1560
ccccgcttca tccccgagaa ccagcgcacc gtcgccgtat acagcttgaa gatcgccggg   1620
tggcacgggc caaggccccc atacacgagc accctgctgc cccggagct gtccgagacc   1680 cccaacgcca cgcagccaga actcgccccg gaagaccccg aggattcggc cctcttggag   1740
gaccccgtgg ggacggtggc cgcgcaaatc ccaccaaact ggcacatacc gtcgatccag   1800
gacgccgcga cgccttacca tccccggcc accccgaaca catgggcct gatcgccggc   1860 gcggtgggcg gcagtctcct ggcagccctg tcatttgcg gaattgtgta ctggatgcgc   1920
cgccgcactc aaaaagcccc aaagcgcata cgcctccccc acatccggga agacgaccag   1980
ccgtcctcgc accagccctt gttttactag                                    2010
```

<210> SEQ ID NO 3
<211> LENGTH: 669
<212> TYPE: PRT
<213> ORGANISM: Artificial sequence
<220> FEATURE:
<223> OTHER INFORMATION: Amino acid sequence of the precursor of gD
      having inserted the GCN4 peptide and scFv to HER2 receptor as
      encoded by the construct R-87.

<400> SEQUENCE: 3

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Gly Ser Lys Asn Tyr His Leu Glu Asn Glu Val Ala Arg Leu Lys

```
            50                  55                  60
Lys Leu Val Gly Ser Leu Asp Gln Leu Thr Asp Pro Pro Gly Val Glu
 65                  70                  75                  80

Asn Ser Asp Ile Gln Met Thr Gln Ser Pro Ser Ser Leu Ser Ala Ser
                 85                  90                  95

Val Gly Asp Arg Val Thr Ile Thr Cys Arg Ala Ser Gln Asp Val Asn
                100                 105                 110

Thr Ala Val Ala Trp Tyr Gln Gln Lys Pro Gly Lys Ala Pro Lys Leu
            115                 120                 125

Leu Ile Tyr Ser Ala Ser Phe Leu Tyr Ser Gly Val Pro Ser Arg Phe
        130                 135                 140

Ser Gly Ser Arg Ser Gly Thr Asp Phe Thr Leu Thr Ile Ser Ser Leu
145                 150                 155                 160

Gln Pro Glu Asp Phe Ala Thr Tyr Tyr Cys Gln Gln His Tyr Thr Thr
                165                 170                 175

Pro Pro Thr Phe Gly Gln Gly Thr Lys Val Glu Ile Lys Ser Asp Met
            180                 185                 190

Pro Met Ala Asp Pro Asn Arg Phe Arg Gly Lys Asn Leu Val Phe His
        195                 200                 205

Ser Glu Val Gln Leu Val Glu Ser Gly Gly Gly Leu Val Gln Pro Gly
210                 215                 220

Gly Ser Leu Arg Leu Ser Cys Ala Ala Ser Gly Phe Asn Ile Lys Asp
225                 230                 235                 240

Thr Tyr Ile His Trp Val Arg Gln Ala Pro Gly Lys Gly Leu Glu Trp
                245                 250                 255

Val Ala Arg Ile Tyr Pro Thr Asn Gly Tyr Thr Arg Tyr Ala Asp Ser
            260                 265                 270

Val Lys Gly Arg Phe Thr Ile Ser Ala Asp Thr Ser Lys Asn Thr Ala
        275                 280                 285

Tyr Leu Gln Met Asn Ser Leu Arg Ala Glu Asp Thr Ala Val Tyr Tyr
        290                 295                 300

Cys Ser Arg Trp Gly Gly Asp Gly Phe Tyr Ala Met Asp Tyr Trp Gly
305                 310                 315                 320

Gln Gly Thr Leu Val Thr Val Ser Ser Gly Gly Gly Ser Gly Ser
                325                 330                 335

Gly Gly Ser Ile Gln Ala Gly Leu Pro Asp Pro Phe Gln Pro Pro Ser
            340                 345                 350

Leu Pro Ile Thr Val Tyr Tyr Ala Val Leu Glu Arg Ala Cys Arg Ser
        355                 360                 365

Val Leu Leu Asn Ala Pro Ser Glu Ala Pro Gln Ile Val Arg Gly Ala
        370                 375                 380

Ser Glu Asp Val Arg Lys Gln Pro Tyr Asn Leu Thr Ile Ala Trp Phe
385                 390                 395                 400

Arg Met Gly Gly Asn Cys Ala Ile Pro Ile Thr Val Met Glu Tyr Thr
                405                 410                 415

Glu Cys Ser Tyr Asn Lys Ser Leu Gly Ala Cys Pro Ile Arg Thr Gln
            420                 425                 430

Pro Arg Trp Asn Tyr Tyr Asp Ser Phe Ser Ala Val Ser Glu Asp Asn
        435                 440                 445

Leu Gly Phe Leu Met His Ala Pro Ala Phe Glu Thr Ala Gly Thr Tyr
        450                 455                 460

Leu Arg Leu Val Lys Ile Asn Asp Trp Thr Glu Ile Thr Gln Phe Ile
465                 470                 475                 480
```

```
Leu Glu His Arg Ala Lys Gly Ser Cys Lys Tyr Ala Leu Pro Leu Arg
            485                 490                 495

Ile Pro Pro Ser Ala Cys Leu Ser Pro Gln Ala Tyr Gln Gln Gly Val
            500                 505                 510

Thr Val Asp Ser Ile Gly Met Leu Pro Arg Phe Ile Pro Glu Asn Gln
            515                 520                 525

Arg Thr Val Ala Val Tyr Ser Leu Lys Ile Ala Gly Trp His Gly Pro
            530                 535                 540

Lys Ala Pro Tyr Thr Ser Thr Leu Leu Pro Pro Glu Leu Ser Glu Thr
545                 550                 555                 560

Pro Asn Ala Thr Gln Pro Glu Leu Ala Pro Glu Asp Pro Glu Asp Ser
            565                 570                 575

Ala Leu Leu Glu Asp Pro Val Gly Thr Val Ala Pro Gln Ile Pro Pro
            580                 585                 590

Asn Trp His Ile Pro Ser Ile Gln Asp Ala Ala Thr Pro Tyr His Pro
            595                 600                 605

Pro Ala Thr Pro Asn Asn Met Gly Leu Ile Ala Gly Ala Val Gly Gly
            610                 615                 620

Ser Leu Leu Ala Ala Leu Val Ile Cys Gly Ile Val Tyr Trp Met Arg
625                 630                 635                 640

Arg Arg Thr Gln Lys Ala Pro Lys Arg Ile Arg Leu Pro His Ile Arg
            645                 650                 655

Glu Asp Asp Gln Pro Ser Ser His Gln Pro Leu Phe Tyr
            660                 665

<210> SEQ ID NO 4
<211> LENGTH: 1995
<212> TYPE: DNA
<213> ORGANISM: Artificial sequence
<220> FEATURE:
<223> OTHER INFORMATION: Nucleotide sequence of chimeric gD-GCN4, scFv
      HER2 of R-89

<400> SEQUENCE: 4 atggggggggg ctgccgccag ttgggggcc gtgattttgt tgtcgtcat agtgggcctc        60 catgggtcc gcggcaaata tgccttggcg gatgcctctc tcaagatggc cgaccccaat       120
cgctttcgcg gcaaagacct tccggtcgga tccaagaact accacctgga gaacgaggtg      180
gccagactga agaagctggt gggcagcctg accagctga ccgaccctcc ggggtccgg       240 cgcgtgtacc acatccaggc gggcctacca gaccgttcc agccccccag cctcccgatc      300
acggtttact acgccgtgtt ggagcgcgcc tgccgcagcg tgctcctaaa cgcaccgtcg      360
gaggcccccc agattgtccg cggggcctcc gaagacgtcc ggaaacaacc ctacaacctg      420
accatcgctt ggtttcggat gggaggcaac tgtgctatcc ccatcacggt catggagtac      480
accgaatgct cctacaacaa gtctctgggg gcctgtccca tccgaacgca gcccgctgg      540 aactactatg acagcttcag cgccgtcagc gaggataacc tggggttcct gatgcacgcc      600
cccgcgtttg agaccgccgg cacgtacctg cggctcgtga agataaacga ctggacggag      660
attacacagt ttatcctgga gcaccgagcc aagggctcct gtaagtacgc cctcccgctg      720 cgcatcccc cgtcagcctg cctgtccccc caggcctacc agcagggggt gacggtggac      780
agcatcggga tgctgccccg cttcgagaat ccgatatcc agatgaccca gtccccgagc      840
tccctgtccg cctctgtggg cgatagggtc accatcacct gccgtgccag tcaggatgtg      900
aatactgctg tagcctggta tcaacagaaa ccaggaaaag ctccgaagct tctgatttac      960
```

```
tcggcatcct tcctctactc tggagtccct tctcgcttct ctggtagccg ttccgggacg    1020
gatttcactc tgaccatcag cagtctgcag ccggaagact tcgcaactta ttactgtcag    1080
caacattata ctactcctcc cacgttcgga cagggtacca aggtggagat caaatcggat    1140
atgccgatgg ctgatccgaa ccgtttccgc ggtaagaacc tggttttca ttctgaggtt     1200 cagctggtgg agtctggcgg tggcctggtg cagccagggg gctcactccg tttgtcctgt    1260
gcagcttctg gcttcaacat taaagacacc tatatacact gggtgcgtca ggcccccggt    1320
aagggcctgg aatgggttgc aaggatttat cctacgaatg ttatactag atatgccgat     1380 agcgtcaagg gccgtttcac tataagcgca gacacatcca aaaacacagc ctacctacaa    1440
atgaacagct taagagctga ggacactgcc gtctattatt gtagccgctg ggaggggac     1500 ggcttctatg ctatggacta ctggggtcaa ggaacactag tcaccgtctc ctcgagtggc    1560
ggtggctctg gttccggtgg atcctacagc ttgaagatcg ccgggtggca cgggcccaag    1620
gccccataca cgagcaccct gctgcccccg gagctgtccg agaccccaa cgccacgcag      1680 ccagaactcg ccccggaaga ccccgaggat tcggccctct tggaggaccc cgtggggacg    1740
gtggcgccgc aaatcccacc aaactggcac ataccgtcga tccaggacgc cgcgacgcct    1800
taccatcccc cggccacccc gaacaacatg gcctgatcg ccggcgcggt gggcggcagt     1860
ctcctggcag ccctggtcat ttgcggaatt gtgtactgga tgcgccgccg cactcaaaaa    1920
gccccaaagc gcatacgcct cccccacatc cgggaagacg accagccgtc ctcgcaccag    1980
cccttgtttt actag                                                     1995
```

<210> SEQ ID NO 5
<211> LENGTH: 664
<212> TYPE: PRT
<213> ORGANISM: Artificial sequence
<220> FEATURE:
<223> OTHER INFORMATION: Amino acid sequence of the precursor of gD
      having inserted the GCN4 peptide  and scFv to HER2 receptor as
      encoded by the construct R-89.

<400> SEQUENCE: 5

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Gly Ser Lys Asn Tyr His Leu Glu Asn Glu Val Ala Arg Leu Lys
    50                  55                  60

Lys Leu Val Gly Ser Leu Asp Gln Leu Thr Asp Pro Pro Gly Val Arg
65                  70                  75                  80

Arg Val Tyr His Ile Gln Ala Gly Leu Pro Asp Pro Phe Gln Pro Pro
                85                  90                  95

Ser Leu Pro Ile Thr Val Tyr Tyr Ala Val Leu Glu Arg Ala Cys Arg
            100                 105                 110

Ser Val Leu Leu Asn Ala Pro Ser Glu Ala Pro Gln Ile Val Arg Gly
        115                 120                 125

Ala Ser Glu Asp Val Arg Lys Gln Pro Tyr Asn Leu Thr Ile Ala Trp
    130                 135                 140

Phe Arg Met Gly Gly Asn Cys Ala Ile Pro Ile Thr Val Met Glu Tyr
145                 150                 155                 160
```

```
Thr Glu Cys Ser Tyr Asn Lys Ser Leu Gly Ala Cys Pro Ile Arg Thr
                165                 170                 175
Gln Pro Arg Trp Asn Tyr Tyr Asp Ser Phe Ser Ala Val Ser Glu Asp
            180                 185                 190
Asn Leu Gly Phe Leu Met His Ala Pro Ala Phe Glu Thr Ala Gly Thr
        195                 200                 205
Tyr Leu Arg Leu Val Lys Ile Asn Asp Trp Thr Glu Ile Thr Gln Phe
    210                 215                 220
Ile Leu Glu His Arg Ala Lys Gly Ser Cys Lys Tyr Ala Leu Pro Leu
225                 230                 235                 240
Arg Ile Pro Pro Ser Ala Cys Leu Ser Pro Gln Ala Tyr Gln Gln Gly
                245                 250                 255
Val Thr Val Asp Ser Ile Gly Met Leu Pro Arg Phe Glu Asn Ser Asp
            260                 265                 270
Ile Gln Met Thr Gln Ser Pro Ser Ser Leu Ser Ala Ser Val Gly Asp
        275                 280                 285
Arg Val Thr Ile Thr Cys Arg Ala Ser Gln Asp Val Asn Thr Ala Val
    290                 295                 300
Ala Trp Tyr Gln Gln Lys Pro Gly Lys Ala Pro Lys Leu Leu Ile Tyr
305                 310                 315                 320
Ser Ala Ser Phe Leu Tyr Ser Gly Val Pro Ser Arg Phe Ser Gly Ser
                325                 330                 335
Arg Ser Gly Thr Asp Phe Thr Leu Thr Ile Ser Ser Leu Gln Pro Glu
            340                 345                 350
Asp Phe Ala Thr Tyr Tyr Cys Gln Gln His Tyr Thr Thr Pro Pro Thr
        355                 360                 365
Phe Gly Gln Gly Thr Lys Val Glu Ile Lys Ser Asp Met Pro Met Ala
    370                 375                 380
Asp Pro Asn Arg Phe Arg Gly Lys Asn Leu Val Phe His Ser Glu Val
385                 390                 395                 400
Gln Leu Val Glu Ser Gly Gly Gly Leu Val Gln Pro Gly Gly Ser Leu
                405                 410                 415
Arg Leu Ser Cys Ala Ala Ser Gly Phe Asn Ile Lys Asp Thr Tyr Ile
            420                 425                 430
His Trp Val Arg Gln Ala Pro Gly Lys Gly Leu Glu Trp Val Ala Arg
        435                 440                 445
Ile Tyr Pro Thr Asn Gly Tyr Thr Arg Tyr Ala Asp Ser Val Lys Gly
    450                 455                 460
Arg Phe Thr Ile Ser Ala Asp Thr Ser Lys Asn Thr Ala Tyr Leu Gln
465                 470                 475                 480
Met Asn Ser Leu Arg Ala Glu Asp Thr Ala Val Tyr Tyr Cys Ser Arg
                485                 490                 495
Trp Gly Gly Asp Gly Phe Tyr Ala Met Asp Tyr Trp Gly Gln Gly Thr
            500                 505                 510
Leu Val Thr Val Ser Ser Gly Gly Ser Gly Ser Gly Gly Ser
        515                 520                 525
Tyr Ser Leu Lys Ile Ala Gly Trp His Gly Pro Lys Ala Pro Tyr Thr
    530                 535                 540
Ser Thr Leu Leu Pro Pro Glu Leu Ser Glu Thr Pro Asn Ala Thr Gln
545                 550                 555                 560
Pro Glu Leu Ala Pro Glu Asp Pro Glu Asp Ser Ala Leu Leu Glu Asp
                565                 570                 575
Pro Val Gly Thr Val Ala Pro Gln Ile Pro Pro Asn Trp His Ile Pro
```

```
                  580             585             590
Ser Ile Gln Asp Ala Ala Thr Pro Tyr His Pro Pro Ala Thr Pro Asn
            595                 600             605

Asn Met Gly Leu Ile Ala Gly Ala Val Gly Gly Ser Leu Leu Ala Ala
            610                 615             620

Leu Val Ile Cys Gly Ile Val Tyr Trp Met Arg Arg Thr Gln Lys
625                 630             635                 640

Ala Pro Lys Arg Ile Arg Leu Pro His Ile Arg Glu Asp Asp Gln Pro
                645             650                 655

Ser Ser His Gln Pro Leu Phe Tyr
            660
```

<210> SEQ ID NO 6
<211> LENGTH: 2010
<212> TYPE: DNA
<213> ORGANISM: Artificial sequence
<220> FEATURE:
<223> OTHER INFORMATION: Nucleotide sequence of chimeric gD-GCN4, scFv HER2 of R-97

<400> SEQUENCE: 6

| | | | | | |
|---|---|---|---|---|---|
| atggggggg | ctgccgccag | gttgggggcc | gtgattttgt | tgtcgtcat | agtgggcctc | 60 |
| catgggtcc | gcggcaaata | tgccttggcg | gatgcctctc | tcaagatggc | cgaccccaat | 120 |
| cgctttcgcg | gcaaagacct | tccggtcgag | aattccgata | tccagatgac | ccagtccccg | 180 |
| agctccctgt | ccgcctctgt | gggcgatagg | gtcaccatca | cctgccgtgc | cagtcaggat | 240 |
| gtgaatactg | ctgtagcctg | gtatcaacag | aaaccaggaa | aagctccgaa | gcttctgatt | 300 |
| tactcggcat | ccttcctcta | ctctggagtc | ccttctcgct | tctctggtag | ccgttccggg | 360 |
| acggatttca | ctctgaccat | cagcagtctg | cagccggaag | acttcgcaac | ttattactgt | 420 |
| cagcaacatt | atactactcc | tcccacgttc | ggacagggta | ccaaggtgga | gatcaaatcg | 480 |
| gatatgccga | tggctgatcc | gaaccgtttc | gcggtaagaa | acctggtttt | tcattctgag | 540 |
| gttcagctgg | tggagtctgg | cggtggcctg | gtgcagccag | ggggctcact | ccgtttgtcc | 600 |
| tgtgcagctt | ctggcttcaa | cattaaagac | acctatatac | actgggtgcg | tcaggccccg | 660 |
| ggtaagggcc | tggaatgggt | tgcaaggatt | tatcctacga | atggttatac | tagatatgcc | 720 |
| gatagcgtca | agggccgttt | cactataagc | gcagacacat | ccaaaaacac | agcctaccta | 780 |
| caaatgaaca | gcttaagagc | tgaggacact | gccgtctatt | attgtagccg | ctggggaggg | 840 |
| gacggcttct | atgctatgga | ctactggggt | caaggaacac | tagtcaccgt | ctcctcgagt | 900 |
| ggcggtggct | ctggttccgg | tggatccctg | accagctgac | cgaccctcc | ggggtcgga | 960 |
| tccaagaact | accacctgga | gaacgaggtg | gccagactga | agaagctggt | gggcagcatc | 1020 |
| caggcgggcc | taccagaccc | gttccagccc | cccagcctcc | cgatcacggt | ttactacgcc | 1080 |
| gtgttggagc | gcgcctgccg | cagcgtgctc | ctaaacgcac | cgtcggaggc | ccccagatt | 1140 |
| gtccgcgggg | cctccgaaga | cgtccggaaa | caacccctaca | acctgaccat | cgcttggttt | 1200 |
| cggatgggag | gcaactgtgc | tatccccatc | acggtcatgg | agtacaccga | atgctcctac | 1260 |
| aacaagtctc | tggggccctg | tcccatccga | acgcagcccc | gctggaacta | ctatgacagc | 1320 |
| ttcagcgccg | tcagcgagga | taacctgggg | ttcctgatgc | acgccccgc | gtttgagacc | 1380 |
| gccggcacgt | acctgcggct | cgtgaagata | aacgactgga | cggagattac | acagtttatc | 1440 |
| ctggagcacc | gagccaaggg | ctcctgtaag | tacgccctcc | cgctgcgcat | cccccgtca | 1500 |
| gcctgcctgt | ccccccaggc | ctaccagcag | ggggtgacgg | tggacagcat | cgggatgctg | 1560 |

```
cccgcttca tccccgagaa ccagcgcacc gtcgccgtat acagcttgaa gatcgccggg    1620
tggcacgggc ccaaggcccc atacacgagc accctgctgc cccggagct gtccgagacc    1680 cccaacgcca cgcagccaga actcgccccg gaagaccccg aggattcggc cctcttggag    1740
gaccccgtgg ggacggtggc gccgcaaatc ccaccaaact ggcacatacc gtcgatccag    1800
gacgccgcga cgccttacca tcccccggcc accccgaaca acatgggcct gatcgccggc    1860
gcggtgggcg gcagtctcct ggcagccctg gtcatttgcg gaattgtgta ctggatgcgc    1920
cgccgcactc aaaaagcccc aaagcgcata cgcctccccc acatccggga agacgaccag    1980
ccgtcctcgc accagcccett gttttactag                                    2010
```

<210> SEQ ID NO 7
<211> LENGTH: 669
<212> TYPE: PRT
<213> ORGANISM: Artificial sequence
<220> FEATURE:
<223> OTHER INFORMATION: Amino acid sequence of the precursor of gD
      having inserted the scFv to HER2 receptor and the GCN4 peptide as
      encoded by the construct R-97

<400> SEQUENCE: 7

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20

Tyr Tyr Cys Ser Arg Trp Gly Gly Asp Gly Phe Tyr Ala Met Asp Tyr
            275                 280                 285

Trp Gly Gln Gly Thr Leu Val Thr Val Ser Ser Ser Gly Gly Gly Ser
        290                 295                 300

Gly Ser Gly Gly Ser Leu Asp Gln Leu Thr Asp Pro Pro Gly Val Gly
305                 310                 315                 320

Ser Lys Asn Tyr His Leu Glu Asn Glu Val Ala Arg Leu Lys Lys Leu
                325                 330                 335

Val Gly Ser Ile Gln Ala Gly Leu Pro Asp Pro Phe Gln Pro Pro Ser
            340                 345                 350

Leu Pro Ile Thr Val Tyr Ala Val Leu Glu Arg Ala Cys Arg Ser
            355                 360                 365

Val Leu Leu Asn Ala Pro Ser Glu Ala Pro Gln Ile Val Arg Gly Ala
        370                 375                 380

Ser Glu Asp Val Arg Lys Gln Pro Tyr Asn Leu Thr Ile Ala Trp Phe
385                 390                 395                 400

Arg Met Gly Gly Asn Cys Ala Ile Pro Ile Thr Val Met Glu Tyr Thr
                405                 410                 415

Glu Cys Ser Tyr Asn Lys Ser Leu Gly Ala Cys Pro Ile Arg Thr Gln
            420                 425                 430

Pro Arg Trp Asn Tyr Tyr Asp Ser Phe Ser Ala Val Ser Glu Asp Asn
        435                 440                 445

Leu Gly Phe Leu Met His Ala Pro Ala Phe Glu Thr Ala Gly Thr Tyr
450                 455                 460

Leu Arg Leu Val Lys Ile Asn Asp Trp Thr Glu Ile Thr Gln Phe Ile
465                 470                 475                 480

Leu Glu His Arg Ala Lys Gly Ser Cys Lys Tyr Ala Leu Pro Leu Arg
                485                 490                 495

Ile Pro Pro Ser Ala Cys Leu Ser Pro Gln Ala Tyr Gln Gln Gly Val
            500                 505                 510

Thr Val Asp Ser Ile Gly Met Leu Pro Arg Phe Ile Pro Glu Asn Gln
        515                 520                 525

Arg Thr Val Ala Val Tyr Ser Leu Lys Ile Ala Gly Trp His Gly Pro
530                 535                 540

Lys Ala Pro Tyr Thr Ser Thr Leu Leu Pro Pro Glu Leu Ser Glu Thr
545                 550                 555                 560

Pro Asn Ala Thr Gln Pro Glu Leu Ala Pro Glu Asp Pro Glu Asp Ser
                565                 570                 575

Ala Leu Leu Glu Asp Pro Val Gly Thr Val Ala Pro Gln Ile Pro Pro
            580                 585                 590

Asn Trp His Ile Pro Ser Ile Gln Asp Ala Ala Thr Pro Tyr His Pro
        595                 600                 605

Pro Ala Thr Pro Asn Asn Met Gly Leu Ile Ala Gly Ala Val Gly Gly
610                 615                 620

Ser Leu Leu Ala Ala Leu Val Ile Cys Gly Ile Val Tyr Trp Met Arg
625                 630                 635                 640

Arg Arg Thr Gln Lys Ala Pro Lys Arg Ile Arg Leu Pro His Ile Arg
                645                 650                 655

Glu Asp Asp Gln Pro Ser Ser His Gln Pro Leu Phe Tyr
            660                 665

<210> SEQ ID NO 8
<211> LENGTH: 1995

<212> TYPE: DNA
<213> ORGANISM: Artificial sequence
<220> FEATURE:
<223> OTHER INFORMATION: Nucleotide sequence of chimeric gD-GCN4, scFv
      HER2 of R-99

<400> SEQUENCE: 8

| | | | | | | |
|---|---|---|---|---|---|---|
| atggggggggg | ctgccgccag | gttggggggcc | gtgattttgt | ttgtcgtcat | agtgggcctc | 60 |
| catgggggtcc | gcggcaaata | tgccttggcg | gatgcctctc | tcaagatggc | cgaccccaat | 120 |
| cgctttcgcg | gcaaagacct | tccggtcgag | aattccgata | tccagatgac | ccagtccccg | 180 |
| agctccctgt | ccgcctctgt | gggcgatagg | gtcaccatca | cctgccgtgc | cagtcaggat | 240 |
| gtgaatactg | ctgtagcctg | gtatcaacag | aaaccaggaa | aagctccgaa | gcttctgatt | 300 |
| tactcggcat | cctcctctctcta | ctctggagtc | ccttctcgct | tctctggtag | ccgttccggg | 360 |
| acggatttca | ctctgaccat | cagcagtctg | cagccggaag | acttcgcaac | ttattactgt | 420 |
| cagcaacatt | atactactcc | tcccacgttc | ggacagggta | ccaaggtgga | gatcaaatcg | 480 |
| gatatgccga | tggctgatcc | gaaccgtttc | cgcggtaaga | acctggtttt | tcattctgag | 540 |
| gttcagctgg | tggagtctgg | cggtggcctg | gtgcagccag | ggggctcact | ccgtttgtcc | 600 |
| tgtgcagctt | ctggcttcaa | cattaaagac | acctatatac | actgggtgcg | tcaggccccg | 660 |
| ggtaagggcc | tggaatgggt | tgcaaggatt | tatcctacga | atggttatac | tagatatgcc | 720 |
| gatagcgtca | agggccgttt | cactataagc | gcagacacat | ccaaaaacac | agcctaccta | 780 |
| caaatgaaca | gcttaagagc | tgaggacact | gccgtctatt | attgtagccg | ctggggaggg | 840 |
| gacggcttct | atgctatgga | ctactggggt | caaggaacac | tagtcaccgt | ctcctcgagt | 900 |
| ggcggtggct | ctggttccgg | tggatccctg | accagctga | ccgaccctcc | ggggggtccgg | 960 |
| cgcgtgtacc | acatccaggc | gggcctacca | gaccccgttcc | agcccccccag | cctcccgatc | 1020 |
| acggtttact | acgccgtgtt | ggagcgcgcc | tgccgcagcg | tgctcctaaa | cgcaccgtcg | 1080 |
| gaggccccc | agattgtccg | cggggcctcc | gaagacgtcc | ggaaacaacc | ctacaacctg | 1140 |
| accatcgctt | ggtttcggat | gggaggcaac | tgtgctatcc | ccatcacggt | catggagtac | 1200 |
| accgaatgct | cctacaacaa | gtctctgggg | gcctgtccca | tccgaacgca | gccccgctgg | 1260 |
| aactactatg | acagcttcag | cgccgtcagc | gaggataacc | tggggttcct | gatgcacgcc | 1320 |
| cccgcgtttg | agaccgccgg | cacgtacctg | cggctcgtga | agataaacga | ctggacggag | 1380 |
| attacacagt | ttatcctgga | gcaccgagcc | aagggctcct | gtaagtacgc | cctcccgctg | 1440 |
| cgcatccccc | cgtcagcctg | cctgtccccc | caggcctacc | agcagggggt | gacggtggac | 1500 |
| agcatcggga | tgctgccccg | cttcggatcc | aagaactacc | acctggagaa | cgaggtggcc | 1560 |
| agactgaaga | gctggtgggg | cagctacagc | ttgaagatcg | ccgggtggca | cgggcccaag | 1620 |
| gccccataca | cgagcaccct | gctgcccccg | gagctgtccg | agaccccaa | cgccacgcag | 1680 |
| ccagaactcg | ccccggaaga | ccccgaggat | tcggccctct | ggaggacccc | cgtggggacg | 1740 |
| gtggcgccgc | aaatcccacc | aaactggcac | ataccgtcga | tccaggacgc | cgcgacgcct | 1800 |
| taccatcccc | cggccacccc | gaacaacatg | ggcctgatcg | ccggcgcggt | gggcggcagt | 1860 |
| ctcctggcag | ccctggtcat | ttgcggaatt | gtgtactgga | tgcgccgccg | cactcaaaaa | 1920 |
| gccccaaagc | gcatacgcct | ccccccacatc | cgggaagacg | accagccgtc | ctcgcaccag | 1980 |
| cccttgtttt | actag | | | | | 1995 |

<210> SEQ ID NO 9
<211> LENGTH: 664

```
<212> TYPE: PRT
<213> ORGANISM: Artificial sequence
<220> FEATURE:
<223> OTHER INFORMATION: Amino acid sequence of the precursor of gD
      having inserted the scFv to HER2 receptor and the GCN4 peptide as
      encoded by the construct R-99.

<400> SEQUENCE: 9
```

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
                20                  25                  30

Ser Leu Lys Met Ala Asp Pro Asn Arg Phe Arg Gly Lys Asp Leu Pro
            35                  40                  45

Val Glu Asn Ser Asp Ile Gln Met Thr Gln Ser Pro Ser Ser Leu Ser
50                  55                  60

Ala Ser Val Gly Asp Arg Val Thr Ile Thr Cys Arg Ala Ser Gln Asp
65                  70                  75                  80

Val Asn Thr Ala Val Ala Trp Tyr Gln Gln Lys Pro Gly Lys Ala Pro
                85                  90                  95

Lys Leu Leu Ile Tyr Ser Ala Ser Phe Leu Tyr Ser Gly Val Pro Ser
            100                 105                 110

Arg Phe Ser Gly Ser Arg Ser Gly Thr Asp Phe Thr Leu Thr Ile Ser
        115                 120                 125

Ser Leu Gln Pro Glu Asp Phe Ala Thr Tyr Tyr Cys Gln Gln His Tyr
    130                 135                 140

Thr Thr Pro Pro Thr Phe Gly Gln Gly Thr Lys Val Glu Ile Lys Ser
145                 150                 155                 160

Asp Met Pro Met Ala Asp Pro Asn Arg Phe Arg Gly Lys Asn Leu Val
                165                 170                 175

Phe His Ser Glu Val Gln Leu Val Glu Ser Gly Gly Gly Leu Val Gln
            180                 185                 190

Pro Gly Gly Ser Leu Arg Leu Ser Cys Ala Ala Ser Gly Phe Asn Ile
        195                 200                 205

Lys Asp Thr Tyr Ile His Trp Val Arg Gln Ala Pro Gly Lys Gly Leu
    210                 215                 220

Glu Trp Val Ala Arg Ile Tyr Pro Thr Asn Gly Tyr Thr Arg Tyr Ala
225                 230                 235                 240

Asp Ser Val Lys Gly Arg Phe Thr Ile Ser Ala Asp Thr Ser Lys Asn
                245                 250                 255

Thr Ala Tyr Leu Gln Met Asn Ser Leu Arg Ala Glu Asp Thr Ala Val
            260                 265                 270

Tyr Tyr Cys Ser Arg Trp Gly Gly Asp Gly Phe Tyr Ala Met Asp Tyr
        275                 280                 285

Trp Gly Gln Gly Thr Leu Val Thr Val Ser Ser Gly Gly Gly Ser
    290                 295                 300

Gly Ser Gly Gly Ser Leu Asp Gln Leu Thr Asp Pro Pro Gly Val Arg
305                 310                 315                 320

Arg Val Tyr His Ile Gln Ala Gly Leu Pro Asp Pro Phe Gln Pro Pro
                325                 330                 335

Ser Leu Pro Ile Thr Val Tyr Tyr Ala Val Leu Glu Arg Ala Cys Arg
            340                 345                 350

Ser Val Leu Leu Asn Ala Pro Ser Glu Ala Pro Gln Ile Val Arg Gly
        355                 360                 365

Ala Ser Glu Asp Val Arg Lys Gln Pro Tyr Asn Leu Thr Ile Ala Trp

```
            370               375               380
Phe Arg Met Gly Gly Asn Cys Ala Ile Pro Ile Thr Val Met Glu Tyr
385               390               395               400

Thr Glu Cys Ser Tyr Asn Lys Ser Leu Gly Ala Cys Pro Ile Arg Thr
            405               410               415

Gln Pro Arg Trp Asn Tyr Tyr Asp Ser Phe Ser Ala Val Ser Glu Asp
            420               425               430

Asn Leu Gly Phe Leu Met His Ala Pro Ala Phe Glu Thr Ala Gly Thr
            435               440               445

Tyr Leu Arg Leu Val Lys Ile Asn Asp Trp Thr Glu Ile Thr Gln Phe
450               455               460

Ile Leu Glu His Arg Ala Lys Gly Ser Cys Lys Tyr Ala Leu Pro Leu
465               470               475               480

Arg Ile Pro Pro Ser Ala Cys Leu Ser Pro Gln Ala Tyr Gln Gln Gly
            485               490               495

Val Thr Val Asp Ser Ile Gly Met Leu Pro Arg Phe Gly Ser Lys Asn
            500               505               510

Tyr His Leu Glu Asn Glu Val Ala Arg Leu Lys Lys Leu Val Gly Ser
            515               520               525

Tyr Ser Leu Lys Ile Ala Gly Trp His Gly Pro Lys Ala Pro Tyr Thr
530               535               540

Ser Thr Leu Leu Pro Pro Glu Leu Ser Glu Thr Pro Asn Ala Thr Gln
545               550               555               560

Pro Glu Leu Ala Pro Glu Asp Pro Glu Asp Ser Ala Leu Leu Glu Asp
            565               570               575

Pro Val Gly Thr Val Ala Pro Gln Ile Pro Pro Asn Trp His Ile Pro
            580               585               590

Ser Ile Gln Asp Ala Ala Thr Pro Tyr His Pro Ala Thr Pro Asn
            595               600               605

Asn Met Gly Leu Ile Ala Gly Ala Val Gly Gly Ser Leu Leu Ala Ala
            610               615               620

Leu Val Ile Cys Gly Ile Val Tyr Trp Met Arg Arg Thr Gln Lys
625               630               635               640

Ala Pro Lys Arg Ile Arg Leu Pro His Ile Arg Glu Asp Asp Gln Pro
            645               650               655

Ser Ser His Gln Pro Leu Phe Tyr
            660

<210> SEQ ID NO 10
<211> LENGTH: 2013
<212> TYPE: DNA
<213> ORGANISM: Artificial sequence
<220> FEATURE:
<223> OTHER INFORMATION: Nucleotide sequence of chimeric gD-GCN4, scFv
      HER2 of R-99-2

<400> SEQUENCE: 10
atgggggggg ctgccgccag gttgggggcc gtgattttgt ttgtcgtcat agtgggcctc      60 catgggtcc gcggcaaata tgccttggcg gatgcctctc tcaagatggc cgaccccaat     120
cgctttcgcg gcaaagacct tccggtcgag aattccgata tccagatgac ccagtccccg     180
agctccctgt ccgcctctgt gggcgatagg gtcaccatca cctgccgtgc cagtcaggat     240
gtgaatactg ctgtagcctg gtatcaacag aaaccaggaa aagctccgaa gcttctgatt     300
tactcggcat ccttcctcta ctctggagtc ccttctcgct tctctggtag ccgttccggg     360
```

```
acggatttca ctctgaccat cagcagtctg cagccggaag acttcgcaac ttattactgt    420
cagcaacatt atactactcc tcccacgttc ggacagggta ccaaggtgga gatcaaatcg    480
gatatgccga tggctgatcc gaaccgtttc cgcggtaaga acctggtttt tcattctgag    540
gttcagctgg tggagtctgg cggtggcctg gtgcagccag ggggctcact ccgtttgtcc    600
tgtgcagctt ctggcttcaa cattaaagac acctatatac actgggtgcg tcaggccccg    660
ggtaagggcc tggaatgggt tgcaaggatt tatcctacga atggttatac tagatatgcc    720
gatagcgtca agggccgttt cactataagc gcagacacat ccaaaaacac agcctaccta    780
caaatgaaca gcttaagagc tgaggacact gccgtctatt attgtagccg ctggggaggg    840
gacggcttct atgctatgga ctactggggt caaggaacac tagtcaccgt ctcctcgagt    900
ggcggtggct ctggttccgg tggatccctg accagctga ccgaccctcc ggggtccgg    960 cgcgtgtacc acatccaggc gggcctacca gacccgttcc agcccccag cctcccgatc   1020 acggtttact acgccgtgtt ggagcgcgcc tgccgcagcg tgctcctaaa cgcaccgtcg   1080
gaggcccccc agattgtccg cggggcctcc gaagacgtcc ggaaacaacc ctacaacctg   1140
accatcgctt ggtttcggat gggaggcaac tgtgctatcc ccatcacggt catggagtac   1200
accgaatgct cctacaacaa gtctctgggg gcctgtccca tccgaacgca gccccgctgg   1260
aactactatg acagcttcag cgccgtcagc gaggataacc tggggttcct gatgcacgcc   1320
cccgcgtttg agaccgccgg cacgtacctg cggctcgtga agataaacga ctggacggag   1380
attacacagt ttatcctgga gcaccgagcc aagggctcct gtaagtacgc cctcccgctg   1440
cgcatccccc cgtcagcctg cctgtccccc aggcctacc agcaggggt gacggtggac   1500 agcatcggga tgctgccccg cttcatcccc gagaaccagc gcggatccaa gaactaccac   1560
ctggagaacg aggtggccag actgaagaag ctggtgggca gctacagctt gaagatcgcc   1620
gggtggcacg ggcccaaggc cccatacacg agcaccctgc tgcccccgga gctgtccgag   1680 accccccaacg ccacgcagcc agaactcgcc ccggaagacc ccgaggattc ggccctcttg   1740
gaggaccccg tggggacggt ggcgccgcaa atcccaccaa actggcacat accgtcgatc   1800
caggacgccg cgacgcctta ccatcccccg gccaccccga caacatggg cctgatcgcc   1860 ggcgcggtgg gcggcagtct cctggcagcc ctggtcattt gcggaattgt gtactggatg   1920
cgccgccgca ctcaaaaagc cccaaagcgc atacgcctcc cccacatccg gaagacgac   1980 cagccgtcct cgcaccagcc cttgtttac tag                                  2013
```

<210> SEQ ID NO 11
<211> LENGTH: 670
<212> TYPE: PRT
<213> ORGANISM: Artificial sequence
<220> FEATURE:
<223> OTHER INFORMATION: Amino acid sequence of the precursor of gD
      having inserted the scFv to HER2 receptor and the GCN4 peptide as encoded by the construct R-99-2

<400> SEQUENCE: 11

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Glu Asn Ser Asp Ile Gln Met Thr Gln Ser Pro Ser Ser Leu Ser
    50                  55                  60
```

```
Ala Ser Val Gly Asp Arg Val Thr Ile Thr Cys Arg Ala Ser Gln Asp
 65                  70                  75                  80

Val Asn Thr Ala Val Ala Trp Tyr Gln Gln Lys Pro Gly Lys Ala Pro
                 85                  90                  95

Lys Leu Leu Ile Tyr Ser Ala Ser Phe Leu Tyr Ser Gly Val Pro Ser
            100                 105                 110

Arg Phe Ser Gly Ser Arg Ser Gly Thr Asp Phe Thr Leu Thr Ile Ser
        115                 120                 125

Ser Leu Gln Pro Glu Asp Phe Ala Thr Tyr Tyr Cys Gln Gln His Tyr
130                 135                 140

Thr Thr Pro Pro Thr Phe Gly Gln Gly Thr Lys Val Glu Ile Lys Ser
145                 150                 155                 160

Asp Met Pro Met Ala Asp Pro Asn Arg Phe Arg Gly Lys Asn Leu Val
                165                 170                 175

Phe His Ser Glu Val Gln Leu Val Glu Ser Gly Gly Gly Leu Val Gln
            180                 185                 190

Pro Gly Gly Ser Leu Arg Leu Ser Cys Ala Ala Ser Gly Phe Asn Ile
        195                 200                 205

Lys Asp Thr Tyr Ile His Trp Val Arg Gln Ala Pro Gly Lys Gly Leu
210                 215                 220

Glu Trp Val Ala Arg Ile Tyr Pro Thr Asn Gly Tyr Thr Arg Tyr Ala
225                 230                 235                 240

Asp Ser Val Lys Gly Arg Phe Thr Ile Ser Ala Asp Thr Ser Lys Asn
                245                 250                 255

Thr Ala Tyr Leu Gln Met Asn Ser Leu Arg Ala Glu Asp Thr Ala Val
            260                 265                 270

Tyr Tyr Cys Ser Arg Trp Gly Gly Asp Gly Phe Tyr Ala Met Asp Tyr
        275                 280                 285

Trp Gly Gln Gly Thr Leu Val Thr Val Ser Ser Gly Gly Gly Gly Ser
290                 295                 300

Gly Ser Gly Gly Ser Leu Asp Gln Leu Thr Asp Pro Pro Gly Val Arg
305                 310                 315                 320

Arg Val Tyr His Ile Gln Ala Gly Leu Pro Asp Pro Phe Gln Pro Pro
                325                 330                 335

Ser Leu Pro Ile Thr Val Tyr Tyr Ala Val Leu Glu Arg Ala Cys Arg
            340                 345                 350

Ser Val Leu Leu Asn Ala Pro Ser Glu Ala Pro Gln Ile Val Arg Gly
        355                 360                 365

Ala Ser Glu Asp Val Arg Lys Gln Pro Tyr Asn Leu Thr Ile Ala Trp
370                 375                 380

Phe Arg Met Gly Gly Asn Cys Ala Ile Pro Ile Thr Val Met Glu Tyr
385                 390                 395                 400

Thr Glu Cys Ser Tyr Asn Lys Ser Leu Gly Ala Cys Pro Ile Arg Thr
                405                 410                 415

Gln Pro Arg Trp Asn Tyr Tyr Asp Ser Phe Ser Ala Val Ser Glu Asp
            420                 425                 430

Asn Leu Gly Phe Leu Met His Ala Pro Ala Phe Glu Thr Ala Gly Thr
        435                 440                 445

Tyr Leu Arg Leu Val Lys Ile Asn Asp Trp Thr Glu Ile Thr Gln Phe
450                 455                 460

Ile Leu Glu His Arg Ala Lys Gly Ser Cys Lys Tyr Ala Leu Pro Leu
465                 470                 475                 480
```

```
Arg Ile Pro Pro Ser Ala Cys Leu Ser Pro Gln Ala Tyr Gln Gln Gly
                485                 490                 495

Val Thr Val Asp Ser Ile Gly Met Leu Pro Arg Phe Ile Pro Glu Asn
        500                 505                 510

Gln Arg Gly Ser Lys Asn Tyr His Leu Glu Asn Glu Val Ala Arg Leu
            515                 520                 525

Lys Lys Leu Val Gly Ser Tyr Ser Leu Lys Ile Ala Gly Trp His Gly
        530                 535                 540

Pro Lys Ala Pro Tyr Thr Ser Thr Leu Leu Pro Glu Leu Ser Glu
545                 550                 555                 560

Thr Pro Asn Ala Thr Gln Pro Glu Leu Ala Pro Glu Asp Pro Glu Asp
                565                 570                 575

Ser Ala Leu Leu Glu Asp Pro Val Gly Thr Val Ala Pro Gln Ile Pro
            580                 585                 590

Pro Asn Trp His Ile Pro Ser Ile Gln Asp Ala Ala Thr Pro Tyr His
                595                 600                 605

Pro Pro Ala Thr Pro Asn Asn Met Gly Leu Ile Ala Gly Ala Val Gly
            610                 615                 620

Gly Ser Leu Leu Ala Ala Leu Val Ile Cys Gly Ile Val Tyr Trp Met
625                 630                 635                 640

Arg Arg Arg Thr Gln Lys Ala Pro Lys Arg Ile Arg Leu Pro His Ile
                645                 650                 655

Arg Glu Asp Asp Gln Pro Ser Ser His Gln Pro Leu Phe Tyr
            660                 665                 670

<210> SEQ ID NO 12
<211> LENGTH: 20
<212> TYPE: PRT
<213> ORGANISM: Artificial sequence
<220> FEATURE:
<223> OTHER INFORMATION: GCN4 peptide

<400> SEQUENCE: 12

Gly Ser Lys Asn Tyr His Leu Glu Asn Glu Val Ala Arg Leu Lys Lys
1               5                   10                  15

Leu Val Gly Ser
            20

<210> SEQ ID NO 13
<211> LENGTH: 12
<212> TYPE: PRT
<213> ORGANISM: Artificial sequence
<220> FEATURE:
<223> OTHER INFORMATION: GCN4 epitope

<400> SEQUENCE: 13

Tyr His Leu Glu Asn Glu Val Ala Arg Leu Lys Lys
1               5                   10

<210> SEQ ID NO 14
<211> LENGTH: 281
<212> TYPE: PRT
<213> ORGANISM: Saccharomyces cerevisiae

<400> SEQUENCE: 14

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30
```

Thr Ser Thr Ala Lys Pro Met Val Gly Gln Leu Ile Phe Asp Lys Phe
    35                  40                  45

Ile Lys Thr Glu Glu Asp Pro Ile Ile Lys Gln Asp Thr Pro Ser Asn
50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
                100                 105                 110

Leu Glu Asp Asn Ser Lys Glu Trp Thr Ser Leu Phe Asp Asn Asp Ile
            115                 120                 125

Pro Val Thr Thr Asp Asp Val Ser Leu Ala Asp Lys Ala Ile Glu Ser
        130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
    210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
            260                 265                 270

Arg Leu Lys Lys Leu Val Gly Glu Arg
        275                 280

<210> SEQ ID NO 15
<211> LENGTH: 846
<212> TYPE: DNA
<213> ORGANISM: Saccharomyces cerevisiae

<400> SEQUENCE: 15
atgtccgaat atcagccaag tttatttgct ttaaatccaa tgggtttctc accattggat      60
ggttctaaat caaccaacga aaatgtatct gcttccactt ctactgccaa accaatggtt     120
ggccaattga tttttgataa attcatcaag actgaagagg atccaattat caaacaggat     180
accccttcga accttgattt tgattttgct cttccacaaa cggcaactgc acctgatgcc     240
aagaccgttt tgccaattcc ggagctagat gccgctgtag tggaatcttt cttttcgtca     300
agcactgatt caactccaat gtttgagtat gaaaacctag aagacaactc taagaatgg      360 acatccttgt ttgacaatga cattccagtt accactgacg atgtttcatt ggctgataag     420
gcaattgaat ccactgaaga gtttctctg gtaccatcca atctggaagt ctcgacaact      480
tcattcttac ccactcctgt tctagaagat gctaaactga ctcaaacaag aaaggttaag     540
aaaccaaatt cagtcgttaa gaagtcacat catgttggaa aggatgacga atcgagactg     600
gatcatctag gtgttgttgc ttacaaccgc aaacagcgtt cgattccact ttctccaatt     660
gtgcccgaat ccagtgatcc tgctgctcta aaacgtgcta gaaacactga agccgccagg     720

```
cgttctcgtg cgagaaagtt gcaaagaatg aaacaacttg aagacaaggt tgaagaattg    780
ctttcgaaaa attatcactt ggaaaatgag gttgccagat taaagaaatt agttggcgaa    840
cgctga                                                               846
```

```
<210> SEQ ID NO 16
<211> LENGTH: 260
<212> TYPE: PRT
<213> ORGANISM: Artificial sequence
<220> FEATURE:
<223> OTHER INFORMATION: Amino acid sequence of scFv HER2 cassette

<400> SEQUENCE: 16
```

Glu Asn Ser Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Ser Asp
            100                 105                 110

Met Pro Met Ala Asp Pro Asn Arg Phe Arg Gly Lys Asn Leu Val Phe
        115                 120                 125

His Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Asn Ile Lys
145                 150                 155                 160

Asp Thr Tyr Ile His Trp Val Arg Gln Ala Pro Gly Lys Gly Leu Glu
                165                 170                 175

Trp Val Ala Arg Ile Tyr Pro Thr Asn Gly Tyr Thr Arg Tyr Ala Asp
            180                 185                 190

Ser Val Lys Gly Arg Phe Thr Ile Ser Ala Asp Thr Ser Lys Asn Thr
        195                 200                 205

Ala Tyr Leu Gln Met Asn Ser Leu Arg Ala Glu Asp Thr Ala Val Tyr
    210                 215                 220

Tyr Cys Ser Arg Trp Gly Gly Asp Gly Phe Tyr Ala Met Asp Tyr Trp
225                 230                 235                 240

Gly Gln Gly Thr Leu Val Thr Val Ser Ser Gly Gly Gly Ser
                245                 250                 255

Ser Gly Gly Ser
            260

```
<210> SEQ ID NO 17
<211> LENGTH: 275
<212> TYPE: PRT
<213> ORGANISM: Artificial sequence
<220> FEATURE:
<223> OTHER INFORMATION: Amino acid sequence of scFv to GCN4 peptide

<400> SEQUENCE: 17
```

Met Glu Thr Asp Thr Leu Leu Leu Trp Val Leu Leu Leu Trp Val Pro

```
  1               5                  10                 15
Gly Ser Thr Gly Asp Tyr Pro Tyr Asp Val Pro Asp Tyr Ala Gly Ala
                20                 25                 30

Asp Ala Val Val Thr Gln Glu Ser Ala Leu Thr Thr Ser Pro Gly Glu
                35                 40                 45

Thr Val Thr Leu Thr Cys Arg Ser Ser Thr Gly Ala Val Thr Thr Ser
            50                 55                 60

Asn Tyr Ala Ser Trp Val Gln Glu Lys Pro Asp His Leu Phe Thr Gly
65                  70                 75                 80

Leu Ile Gly Gly Thr Asn Asn Arg Ala Pro Gly Val Pro Ala Arg Phe
                85                 90                 95

Ser Gly Ser Leu Ile Gly Asp Lys Ala Ala Leu Thr Ile Thr Gly Ala
                100                105                110

Gln Thr Glu Asp Glu Ala Ile Tyr Phe Cys Ala Leu Trp Tyr Ser Asn
                115                120                125

His Trp Val Phe Gly Gly Gly Thr Lys Leu Thr Val Leu Gly Gly Gly
            130                135                140

Gly Gly Ser Gly Gly Gly Ser Gly Gly Gly Ser Gly Gly Gly
145                 150                155                160

Gly Ser Asp Val Gln Leu Gln Gln Ser Gly Pro Gly Leu Val Ala Pro
                165                170                175

Ser Gln Ser Leu Ser Ile Thr Cys Thr Val Ser Gly Phe Ser Leu Thr
            180                185                190

Asp Tyr Gly Val Asn Trp Val Arg Gln Ser Pro Gly Lys Gly Leu Glu
                195                200                205

Trp Leu Gly Val Ile Trp Gly Asp Gly Ile Thr Asp Tyr Asn Ser Ala
            210                215                220

Leu Lys Ser Arg Leu Ser Val Thr Lys Asp Asn Ser Lys Ser Gln Val
225                 230                235                240

Phe Leu Lys Met Asn Ser Leu Gln Ser Gly Asp Ser Ala Arg Tyr Tyr
                245                250                255

Cys Val Thr Gly Leu Phe Asp Tyr Trp Gly Gln Gly Thr Thr Leu Thr
                260                265                270

Val Ser Ser
      275

<210> SEQ ID NO 18
<211> LENGTH: 654
<212> TYPE: PRT
<213> ORGANISM: Artificial sequence
<220> FEATURE:
<223> OTHER INFORMATION: Amino acid sequence of the scFv to GCN4 peptide
      comprising human nectin-1 residues

<400> SEQUENCE: 18

Met Glu Thr Asp Thr Leu Leu Leu Trp Val Leu Leu Leu Trp Val Pro
1               5                  10                 15

Gly Ser Thr Gly Asp Tyr

-continued

```
Leu Ile Gly Gly Thr Asn Asn Arg Ala Pro Gly Val Pro Ala Arg Phe
                85                  90                  95

Ser Gly Ser Leu Ile Gly Asp Lys Ala Ala Leu Thr Ile Thr Gly Ala
            100                 105                 110

Gln Thr Glu Asp Glu Ala Ile Tyr Phe Cys Ala Leu Trp Tyr Ser Asn
        115                 120                 125

His Trp Val Phe Gly Gly Gly Thr Lys Leu Thr Val Leu Gly Gly Gly
    130                 135                 140

Gly Gly Ser Gly Gly Gly Gly Ser Gly Gly Gly Gly Ser Gly Gly Gly
145                 150                 155                 160

Gly Ser Asp Val Gln Leu Gln Gln Ser Gly Pro Gly Leu Val Ala Pro
            165                 170                 175

Ser Gln Ser Leu Ser Ile Thr Cys Thr Val Ser Gly Phe Ser Leu Thr
            180                 185                 190

Asp Tyr Gly Val Asn Trp Val Arg Gln Ser Pro Gly Lys Gly Leu Glu
        195                 200                 205

Trp Leu Gly Val Ile Trp Gly Asp Gly Ile Thr Asp Tyr Asn Ser Ala
    210                 215                 220

Leu Lys Ser Arg Leu Ser Val Thr Lys Asp Asn Ser Lys Ser Gln Val
225                 230                 235                 240

Phe Leu Lys Met Asn Ser Leu Gln Ser Gly Asp Ser Ala Arg Tyr Tyr
                245                 250                 255

Cys Val Thr Gly Leu Phe Asp Tyr Trp Gly Gln Gly Thr Thr Leu Thr
            260                 265                 270

Val Ser Ser Gly Ser Gly Ala Met Ala Lys Pro Thr Asn Trp Ile Glu
        275                 280                 285

Gly Thr Gln Ala Val Leu Arg Ala Lys Lys Gly Gln Asp Asp Lys Val
    290                 295                 300

Leu Val Ala Thr Cys Thr Ser Ala Asn Gly Lys Pro Pro Ser Val Val
305                 310                 315                 320

Ser Trp Glu Thr Arg Leu Lys Gly Glu Ala Glu Tyr Gln Glu Ile Arg
                325                 330                 335

Asn Pro Asn Gly Thr Val Thr Val Ile Ser Arg Tyr Arg Leu Val Pro
            340                 345                 350

Ser Arg Glu Ala His Gln Gln Ser Leu Ala Cys Ile Val Asn Tyr His
        355                 360                 365

Met Asp Arg Phe Lys Glu Ser Leu Thr Leu Asn Val Gln Tyr Glu Pro
    370                 375                 380

Glu Val Thr Ile Glu Gly Phe Asp Gly Asn Trp Tyr Leu Gln Arg Met
385                 390                 395                 400

Asp Val Lys Leu Thr Cys Lys Ala Asp Ala Asn Pro Pro Ala Thr Glu
                405                 410                 415

Tyr His Trp Thr Thr Leu Asn Gly Ser Leu Pro Lys Gly Val Glu Ala
            420                 425                 430

Gln Asn Arg Thr Leu Phe Phe Lys Gly Pro Ile Asn Tyr Ser Leu Ala
        435                 440                 445

Gly Thr Tyr Ile Cys Glu Ala Thr Asn Pro Ile Gly Thr Arg Ser Gly
    450                 455                 460

Gln Val Glu Val Asn Ile Thr Glu Phe Pro Tyr Thr Pro Ser Pro Pro
465                 470                 475                 480

Glu His Gly Arg Arg Ala Gly Pro Val Pro Thr Ala Ile Ile Gly Gly
                485                 490                 495

Val Ala Gly Ser Ile Leu Leu Val Leu Ile Val Val Gly Gly Ile Val
```

-continued

```
            500                 505                 510

Val Ala Leu Arg Arg Arg Arg His Thr Phe Lys Gly Asp Tyr Ser Thr
        515                 520                 525

Lys Lys His Val Tyr Gly Asn Gly Tyr Ser Lys Ala Gly Ile Pro Gln
    530                 535                 540

His His Pro Pro Met Ala Gln Asn Leu Gln Tyr Pro Asp Asp Ser Asp
545                 550                 555                 560

Asp Glu Lys Lys Ala Gly Pro Leu Gly Gly Ser Ser Tyr Glu Glu Glu
                565                 570                 575

Glu Glu Glu Glu Glu Gly Gly Gly Gly Gly Glu Arg Lys Val Gly Gly
            580                 585                 590

Pro His Pro Lys Tyr Asp Glu Asp Ala Lys Arg Pro Tyr Phe Thr Val
        595                 600                 605

Asp Glu Ala Glu Ala Arg Gln Asp Gly Tyr Gly Asp Arg Thr Leu Gly
    610                 615                 620

Tyr Gln Tyr Asp Pro Glu Gln Leu Asp Leu Ala Glu Asn Met Val Ser
625                 630                 635                 640

Gln Asn Asp Gly Ser Phe Ile Ser Lys Lys Glu Trp Tyr Val
                645                 650

<210> SEQ ID NO 19
<211> LENGTH: 1965
<212> TYPE: DNA
<213> ORGANISM: Artificial sequence
<220> FEATURE:
<223> OTHER INFORMATION: Nucleotide sequence encoding the amino acid
      sequence of the scFv to GCN4 peptide comprising human nectin-1
      residues

<400> SEQUENCE: 19
atggaaaccg acacccttct tttgtgggtg cttcttcttt gggtgcccgg gagcaccggg     60
gactacccct acgacgtgcc cgactacgcc ggggctgatg ccgtggtgac ccaggagagc    120
gccttgacca caagccccgg ggagaccgtg accttgacct gtagaagcag cacaggggcc    180
gttacaacct ctaactacgc cagctgggtt caggagaagc ccgaccacct tttcaccgga    240
cttatcggag ggaccaacaa cagagccccc ggggtgcctg ctagattcag cgggagcctt    300
attggggaca aggccgccct taccattacc ggggctcaga ccgaagacga ggctatctac    360
ttctgtgctc tttggtacag caaccattgg gtgttcggag gcgggacaaa gcttacagtg    420
cttggaggcg gtggaggcag cggcggaggt gggtctggtg gagggggctc tgggggaggc    480
ggtagcgacg tgcagcttca gcagagcggg cccgggcttg tggcccccctc tcagtctctt    540 agcataacgt gcaccgtgag cgggttcagc cttaccgact atggggttaa ctgggtgaga    600
cagtctcctg ggaaggggct tgagtggttg ggagttatct ggggagacgg aatcaccgac    660
tacaacagcg ccttgaagag cagactttct gtgacaaagg acaactctaa gagccaggtg    720
ttccttaaga tgaacagcct tcagagcggg gactctgcca gatactactg cgtgacaggg    780
cttttcgact actggggaca agggaccacc ttgaccgtga gcagcggaag cggagccatg    840
gccaagccca ccaactggat cgaggggaca caggccgtgc ttagagccaa gaaggggcag    900
gacgacaagg ttcttgttgc tacttgcacc agcgccaacg gaaagccccc cagcgtggtg    960
agctgggaga caagattgaa aggggaggcc gagtatcagg agatcagaaa ccctaacggg   1020
accgtgaccg tgatcagcag atacagactt gtgcctagca gagaggccca ccagcagagc   1080
cttgcctgca tcgttaacta ccacatggac agattcaagg agagccttac acttaacgtg   1140
```

```
cagtacgaac ccgaggtgac catcgagggg ttcgacggga actggtacct tcagagaatg    1200
gacgtgaagc ttacctgcaa ggccgacgcc aaccctcccg ccaccgagta ccactggacc    1260
acccttaacg ggagccttcc caaaggggtg gaggcccaga acagaaccct tttcttcaag    1320
gggcccatca attacagcct tgccgggacc tacatctgcg aggccaccaa ccccatcggg    1380
accagaagcg gtcaagtgga ggtgaacatc accgagttcc cctacacccc cagcccaccc    1440
gagcacggga aagagctggg gcccgttccc accgccatca tcggagggt ggccgggagc     1500 atcttgcttg tgcttatcgt ggtgggtggg attgtggtgg cccttagaag aagaagacat    1560
accttcaaag gggactacag caccaagaag cacgtgtacg ggaacgggta cagcaaggcc    1620
ggaatccctc agcaccatcc acctatggcc cagaaccttc agtaccccga cgacagcgac    1680
gatgagaaga aggctgggcc ccttggtggg agcagctacg aagaggagga agaagaggaa    1740
gagggtggcg gcggtggaga gagaaaagtg ggagggcctc atcccaaata cgacgaggac    1800
gccaagagac cctacttcac cgtggacgag gccgaggcca gacaggacgg gtacggggac    1860
agaaaccctt ggtaccagta cgaccccgag cagttggact tggccgagaa catggtgagc    1920
cagaacgacg gaagcttcat ctctaagaag gagtggtacg tgtga                   1965

<210> SEQ ID NO 20
<211> LENGTH: 74
<212> TYPE: DNA
<213> ORGANISM: Artificial sequence
<220> FEATURE:
<223> OTHER INFORMATION: Primer gD24_galK_f

<400> SEQUENCE: 20
ctctcaagat ggccgacccc aatcgctttc gcggcaaaga ccttccggtc cctgttgaca    60
attaatcatc ggca                                                     74

<210> SEQ ID NO 21
<211> LENGTH: 70
<212> TYPE: DNA
<213> ORGANISM: Artificial sequence
<220> FEATURE:
<223> OTHER INFORMATION: Primer gD25_galK_r

<400> SEQUENCE: 21
tggatgtggt acacgcgccg gacccccgga gggtcggtca gctggtccag tcagcactgt    60
cctgctcctt                                                          70

<210> SEQ ID NO 22
<211> LENGTH: 20
<212> TYPE: DNA
<213> ORGANISM: Artificial sequence
<220> FEATURE:
<223> OTHER INFORMATION: Primer galK_827_f

<400> SEQUENCE: 22
gcgtgatgtc accattgaag                                               20

<210> SEQ ID NO 23
<211> LENGTH: 20
<212> TYPE: DNA
<213> ORGANISM: Artificial sequence
<220> FEATURE:
<223> OTHER INFORMATION: Primer galK_1142_r

<400> SEQUENCE: 23
tattgttcag cgacagcttg                                               20
```

<210> SEQ ID NO 24
<211> LENGTH: 60
<212> TYPE: DNA
<213> ORGANISM: Artificial sequence
<220> FEATURE:
<223> OTHER INFORMATION: GCN4 peptide cassette

<400> SEQUENCE: 24

```
ggatccaaga actaccacct ggagaacgag gtggccagac tgaagaagct ggtgggcagc      60
```

<210> SEQ ID NO 25
<211> LENGTH: 110
<212> TYPE: DNA
<213> ORGANISM: Artificial sequence
<220> FEATURE:
<223> OTHER INFORMATION: Primer gD24_GCN4_fB

<400> SEQUENCE: 25

```
ctctcaagat ggccgacccc aatcgctttc gcggcaaaga ccttccggtc ggatccaaga      60
actaccacct ggagaacgag gtggccagac tgaagaagct ggtgggcagc                110
```

<210> SEQ ID NO 26
<211> LENGTH: 110
<212> TYPE: DNA
<213> ORGANISM: Artificial sequence
<220> FEATURE:
<223> OTHER INFORMATION: Primer gD25_GCN4_rB

<400> SEQUENCE: 26

```
tggatgtggt acacgcgccg gaccccggga gggtcggtca gctggtccag gctgcccacc      60
agcttcttca gtctggccac ctcgttctcc aggtggtagt tcttggatcc                110
```

<210> SEQ ID NO 27
<211> LENGTH: 1245
<212> TYPE: DNA
<213> ORGANISM: Artificial sequence
<220> FEATURE:
<223> OTHER INFORMATION: Nucleotide sequence of chimeric gD-GCN4 of R-81

<400> SEQUENCE: 27

```
atggggggg ctgccgccag gttgggggcc gtgattttgt ttgtcgtcat agtgggcctc      60 catgggtcc gcggcaaata tgccttggcg gatgcctctc tcaagatggc cgaccccaat     120
cgctttcgcg gcaaagacct tccggtcgga tccaagaact accacctgga gaacgaggtg     180
gccagactga agaagctggt gggcagcctg accagctga ccgaccctcc ggggtccgg      240 cgcgtgtacc acatccaggc gggcctacca gacccgttcc agccccccag cctcccgatc     300
acggtttact acgccgtgtt ggagcgcgcc tgccgcagcg tgctcctaaa cgcaccgtcg     360
gaggcccccc agattgtccg cggggcctcc gaagacgtcc ggaaacaacc ctacaacctg     420
accatcgctt ggtttcggat gggaggcaac tgtgctatcc ccatcacggt catggagtac     480
accgaatgct cctacaacaa gtctctgggg gcctgtccca tccgaacgca gccccgctgg     540
aactactatg acagcttcag cgccgtcagc gaggataacc tggggttcct gatgcacgcc     600
cccgcgtttg agaccgccgg cacgtacctg cggctcgtga agataaacga ctggacggag     660
attacacagt ttatcctgga gcaccgagcc aagggctcct gtaagtacgc cctcccgctg     720
cgcatccccc cgtcagcctg cctgtccccc caggcctacc agcaggggt gacggtggac     780 agcatcggga tgctgccccg cttcatcccc gagaaccagc gcaccgtcgc cgtatacagc     840
```

```
ttgaagatcg ccgggtggca cgggcccaag gccccataca cgagcaccct gctgccccg      900 gagctgtccg agaccccaa cgccacgcag ccagaactcg ccccggaaga ccccgaggat      960
tcggccctct tggaggaccc cgtggggacg gtggcgccgc aaatcccacc aaactggcac   1020
ataccgtcga tccaggacgc cgcgacgcct taccatcccc cggccacccc gaacaacatg  1080
ggcctgatcg ccggcgcggt gggcggcagt ctcctggcag ccctggtcat ttgcggaatt  1140
gtgtactgga tgcgccgccg cactcaaaaa gccccaaagc gcatacgcct ccccacatc   1200 cgggaagacg accagccgtc ctcgcaccag cccttgtttt actag                   1245
```

<210> SEQ ID NO 28
<211> LENGTH: 414
<212> TYPE: PRT
<213> ORGANISM: Artificial sequence
<220> FEATURE:
<223> OTHER INFORMATION: Amino acid sequence of the precursor of gD
      having inserted the GCN4 peptide, as encoded by the construct R-81

<400> SEQUENCE: 28

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Gly Ser Lys Asn Tyr His Leu Glu Asn Glu Val Ala Arg Leu Lys
    50                  55                  60

Lys Leu Val Gly Ser Leu Asp Gln Leu Thr Asp Pro Pro Gly Val Arg
65                  70                  75                  80

Arg Val Tyr His Ile Gln Ala Gly Leu Pro Asp Pro Phe Gln Pro Pro
                85                  90                  95

Ser Leu Pro Ile Thr Val Tyr Tyr Ala Val Leu Glu Arg Ala Cys Arg
            100                 105                 110

Ser Val Leu Leu Asn Ala Pro Ser Glu Ala Pro Gln Ile Val Arg Gly
        115                 120                 125

Ala Ser Glu Asp Val Arg Lys Gln Pro Tyr Asn Leu Thr Ile Ala Trp
    130                 135                 140

Phe Arg Met Gly Gly Asn Cys Ala Ile Pro Ile Thr Val Met Glu Tyr
145                 150                 155                 160

Thr Glu Cys Ser Tyr Asn Lys Ser Leu Gly Ala Cys Pro Ile Arg Thr
                165                 170                 175

Gln Pro Arg Trp Asn Tyr Tyr Asp Ser Phe Ser Ala Val Ser Glu Asp
            180                 185                 190

Asn Leu Gly Phe Leu Met His Ala Pro Ala Phe Glu Thr Ala Gly Thr
        195                 200                 205

Tyr Leu Arg Leu Val Lys Ile Asn Asp Trp Thr Glu Ile Thr Gln Phe
    210                 215                 220

Ile Leu Glu His Arg Ala Lys Gly Ser Cys Lys Tyr Ala Leu Pro Leu
225                 230                 235                 240

Arg Ile Pro Pro Ser Ala Cys Leu Ser Pro Gln Ala Tyr Gln Gln Gly
                245                 250                 255

Val Thr Val Asp Ser Ile Gly Met Leu Pro Arg Phe Ile Pro Glu Asn
            260                 265                 270

Gln Arg Thr Val Ala Val Tyr Ser Leu Lys Ile Ala Gly Trp His Gly
        275                 280                 285
```

```
Pro Lys Ala Pro Tyr Thr Ser Thr Leu Leu Pro Pro Glu Leu Ser Glu
    290                 295                 300

Thr Pro Asn Ala Thr Gln Pro Glu Leu Ala Pro Glu Asp Pro Glu Asp
305                 310                 315                 320

Ser Ala Leu Leu Glu Asp Pro Val Gly Thr Val Ala Pro Gln Ile Pro
                325                 330                 335

Pro Asn Trp His Ile Pro Ser Ile Gln Asp Ala Ala Thr Pro Tyr His
            340                 345                 350

Pro Pro Ala Thr Pro Asn Asn Met Gly Leu Ile Ala Gly Ala Val Gly
        355                 360                 365

Gly Ser Leu Leu Ala Ala Leu Val Ile Cys Gly Ile Val Tyr Trp Met
370                 375                 380

Arg Arg Arg Thr Gln Lys Ala Pro Lys Arg Ile Arg Leu Pro His Ile
385                 390                 395                 400

Arg Glu Asp Asp Gln Pro Ser Ser His Gln Pro Leu Phe Tyr
                405                 410

<210> SEQ ID NO 29
<211> LENGTH: 27
<212> TYPE: DNA
<213> ORGANISM: Artificial sequence
<220> FEATURE:
<223> OTHER INFORMATION: Primer gD_ext_f

<400> SEQUENCE: 29
tccataccga ccacaccgac gaatccc                                        27

<210> SEQ ID NO 30
<211> LENGTH: 24
<212> TYPE: DNA
<213> ORGANISM: Artificial sequence
<220> FEATURE:
<223> OTHER INFORMATION: Primer gD_ext_r

<400> SEQUENCE: 30
gagtttgata ccagactgac cgtg                                           24

<210> SEQ ID NO 31
<211> LENGTH: 74
<212> TYPE: DNA
<213> ORGANISM: Artificial sequence
<220> FEATURE:
<223> OTHER INFORMATION: Primer galK_gD35_F

<400> SEQUENCE: 31
tgaagaagct ggtgggcagc ctggaccagc tgaccgaccc tccgggggtc cctgttgaca    60
attaatcatc ggca                                                     74

<210> SEQ ID NO 32
<211> LENGTH: 70
<212> TYPE: DNA
<213> ORGANISM: Artificial sequence
<220> FEATURE:
<223> OTHER INFORMATION: Primer galK_gD39_R

<400> SEQUENCE: 32
gtgatcggga ggctgggggg ctggaacggg tctggtaggc ccgcctggat tcagcactgt    60
cctgctcctt                                                          70

<210> SEQ ID NO 33
<211> LENGTH: 780
```

<212> TYPE: DNA
<213> ORGANISM: Artificial sequence
<220> FEATURE:
<223> OTHER INFORMATION: Nucleotide sequence of scFv HER2 cassette

<400> SEQUENCE: 33

```
gagaattccg atatccagat gacccagtcc ccgagctccc tgtccgcctc tgtgggcgat    60
agggtcacca tcacctgccg tgccagtcag gatgtgaata ctgctgtagc ctggtatcaa   120
cagaaaccag gaaaagctcc gaagcttctg atttactcgg catccttcct ctactctgga   180
gtcccttctc gcttctctgg tagccgttcc gggacggatt tcactctgac catcagcagt   240
ctgcagccgg aagacttcgc aacttattac tgtcagcaac attatactac tcctcccacg   300
ttcggacagg gtaccaaggt ggagatcaaa tcggatatgc cgatggctga tccgaaccgt   360
ttccgcggta agaacctggt ttttcattct gaggttcagc tggtggagtc tggcggtggc   420
ctggtgcagc cagggggctc actccgtttg tcctgtgcag cttctggctt caacattaaa   480
gacacctata tacactgggt gcgtcaggcc ccgggtaagg gcctggaatg ggttgcaagg   540
atttatccta cgaatggtta tactagatat gccgatagcg tcaagggccg tttcactata   600
agcgcagaca catccaaaaa cacagcctac ctacaaatga acagcttaag agctgaggac   660
actgccgtct attattgtag ccgctgggga ggggacggct tctatgctat ggactactgg   720
ggtcaaggaa cactagtcac cgtctcctcg agtggcggtg gctctggttc cggtggatcc   780
```

<210> SEQ ID NO 34
<211> LENGTH: 70
<212> TYPE: DNA
<213> ORGANISM: Artificial sequence
<220> FEATURE:
<223> OTHER INFORMATION: Primer gD-34-scFvHER2-F

<400> SEQUENCE: 34

```
tgaagaagct ggtgggcagc ctggaccagc tgaccgaccc tccggggggtc gagaattccg    60
atatccagat                                                           70
```

<210> SEQ ID NO 35
<211> LENGTH: 70
<212> TYPE: DNA
<213> ORGANISM: Artificial sequence
<220> FEATURE:
<223> OTHER INFORMATION: Primer gD-40-scFvHER2-R

<400> SEQUENCE: 35

```
gtgatcggga ggctgggggg ctggaacggg tctggtaggc ccgcctggat ggatccaccg    60
gaaccagagc                                                           70
```

<210> SEQ ID NO 36
<211> LENGTH: 30
<212> TYPE: DNA
<213> ORGANISM: Artificial sequence
<220> FEATURE:
<223> OTHER INFORMATION: Primer scFv_456_r

<400> SEQUENCE: 36

```
agctgcacag gacaaacgga gtgagccccc                                     30
```

<210> SEQ ID NO 37
<211> LENGTH: 74
<212> TYPE: DNA
<213> ORGANISM: Artificial sequence
<220> FEATURE:

<223> OTHER INFORMATION: Primer galK_gD214_F

<400> SEQUENCE: 37
cctaccagca gggggtgacg gtggacagca tcgggatgct gccccgcttc cctgttgaca         60
attaatcatc ggca                                                          74

<210> SEQ ID NO 38
<211> LENGTH: 70
<212> TYPE: DNA
<213> ORGANISM: Artificial sequence
<220> FEATURE:
<223> OTHER INFORMATION: Primer galK_gD223_R

<400> SEQUENCE: 38
ctcgtgtatg gggccttggg cccgtgccac ccggcgatct tcaagctgta tcagcactgt         60
cctgctcctt                                                               70

<210> SEQ ID NO 39
<211> LENGTH: 70
<212> TYPE: DNA
<213> ORGANISM: Artificial sequence
<220> FEATURE:
<223> OTHER INFORMATION: Primer gD213-scFvHER2f

<400> SEQUENCE: 39
cctaccagca gggggtgacg gtggacagca tcgggatgct gccccgcttc gagaattccg         60
atatccagat                                                               70

<210> SEQ ID NO 40
<211> LENGTH: 70
<212> TYPE: DNA
<213> ORGANISM: Artificial sequence
<220> FEATURE:
<223> OTHER INFORMATION: Primer gD224-scFvHER2r

<400> SEQUENCE: 40
ctcgtgtatg gggccttggg cccgtgccac ccggcgatct tcaagctgta ggatccaccg         60
gaaccagagc                                                               70

<210> SEQ ID NO 41
<211> LENGTH: 24
<212> TYPE: DNA
<213> ORGANISM: Artificial sequence
<220> FEATURE:
<223> OTHER INFORMATION: Primer gDintforw

<400> SEQUENCE: 41
ccctacaacc tgaccatcgc ttgg                                               24

<210> SEQ ID NO 42
<211> LENGTH: 71
<212> TYPE: DNA
<213> ORGANISM: Artificial sequence
<220> FEATURE:
<223> OTHER INFORMATION: Primer gD24-scFvHer2-F

<400> SEQUENCE: 42
ctctcaagat ggccgacccc aatcgctttc gcggcaaaga ccttccggtc gagaattccg         60
atatccagat g                                                             71

<210> SEQ ID NO 43
<211> LENGTH: 70

```
<212> TYPE: DNA
<213> ORGANISM: Artificial sequence
<220> FEATURE:
<223> OTHER INFORMATION: Primer gD25-scFvHer2-R

<400> SEQUENCE: 43
tggatgtggt acacgcgccg gaccccggga gggtcggtca gctggtccag ggatccaccg      60
gaaccagagc                                                            70

<210> SEQ ID NO 44
<211> LENGTH: 110
<212> TYPE: DNA
<213> ORGANISM: Artificial sequence
<220> FEATURE:
<223> OTHER INFORMATION: Primer gD213-GCN4-F

<400> SEQUENCE: 44
cctaccagca gggggtgacg gtggacagca tcgggatgct gccccgcttc ggatccaaga      60
actaccacct ggagaacgag gtggccagac tgaagaagct ggtgggcagc                110

<210> SEQ ID NO 45
<211> LENGTH: 110
<212> TYPE: DNA
<213> ORGANISM: Artificial sequence
<220> FEATURE:
<223> OTHER INFORMATION: Primer gD224-GCN4-R

<400> SEQUENCE: 45
ctcgtgtatg gggccttggg cccgtgccac ccggcgatct tcaagctgta gctgcccacc      60
agcttcttca gtctggccac ctcgttctcc aggtggtagt tcttggatcc                110

<210> SEQ ID NO 46
<211> LENGTH: 27
<212> TYPE: DNA
<213> ORGANISM: Artificial sequence
<220> FEATURE:
<223> OTHER INFORMATION: Primer HSV_139688_r

<400> SEQUENCE: 46
ccgacttatc gactgtccac ctttccc                                         27

<210> SEQ ID NO 47
<211> LENGTH: 74
<212> TYPE: DNA
<213> ORGANISM: Artificial sequence
<220> FEATURE:
<223> OTHER INFORMATION: Primer gD35-galK-F

<400> SEQUENCE: 47
gctctggttc cggtggatcc ctggaccagc tgaccgaccc tccggggtc cctgttgaca      60 attaatcatc ggca                                                       74

<210> SEQ ID NO 48
<211> LENGTH: 70
<212> TYPE: DNA
<213> ORGANISM: Artificial sequence
<220> FEATURE:
<223> OTHER INFORMATION: Primer gD39-galK-R

<400> SEQUENCE: 48
gtgatcggga ggctgggggg ctggaacggg tctggtaggc ccgcctggat tcagcactgt      60
cctgctcctt                                                            70
```

```
<210> SEQ ID NO 49
<211> LENGTH: 110
<212> TYPE: DNA
<213> ORGANISM: Artificial sequence
<220> FEATURE:
<223> OTHER INFORMATION: Primer gD35-GCN4-F

<400> SEQUENCE: 49
gctctggttc cggtggatcc ctggaccagc tgaccgaccc tccggggggtc ggatccaaga    60 actaccacct ggagaacgag gtggccagac tgaagaagct ggtgggcagc              110

<210> SEQ ID NO 50
<211> LENGTH: 110
<212> TYPE: DNA
<213> ORGANISM: Artificial sequence
<220> FEATURE:
<223> OTHER INFORMATION: Primer gD39-GCN4-R

<400> SEQUENCE: 50
gtgatcggga ggctgggggg ctggaacggg tctggtaggc ccgcctggat gctgcccacc    60
agcttcttca gtctggccac ctcgttctcc aggtggtagt tcttggatcc              110

<210> SEQ ID NO 51
<211> LENGTH: 29
<212> TYPE: DNA
<213> ORGANISM: Artificial sequence
<220> FEATURE:
<223> OTHER INFORMATION: Primer scFv4D5 651_f

<400> SEQUENCE: 51
ggacactgcc gtctattatt gtagccgct                                      29

<210> SEQ ID NO 52
<211> LENGTH: 24
<212> TYPE: DNA
<213> ORGANISM: Artificial sequence
<220> FEATURE:
<223> OTHER INFORMATION: Primer gDintrev

<400> SEQUENCE: 52
ccagtcgttt atcttcacga gccg                                           24

<210> SEQ ID NO 53
<211> LENGTH: 120
<212> TYPE: DNA
<213> ORGANISM: Artificial sequence
<220> FEATURE:
<223> OTHER INFORMATION: Primer gD219-GCN4-F

<400> SEQUENCE: 53
cctaccagca gggggtgacg gtggacagca tcgggatgct gccccgcttc atccccgaga    60
accagcgcgg atccaagaac taccacctgg agaacgaggt ggccagactg aagaagctgg   120
```

The invention claimed is:

1. A recombinant herpesvirus comprising a modified glycoprotein D (gD) said modified gD having:
   a) inactivated HVEM and nectin-1 binding sites,
   b) a first heterologous polypeptide ligand capable of binding to a target molecule present on a cell suitable for growth of the herpesvirus or a cell approved for herpesvirus growth fused to or inserted therein, and c) a second heterologous polypeptide ligand capable of binding to a target molecule present on a diseased cell fused to or inserted therein, wherein the herpesvirus has the capability of fusing with the membrane of the cell suitable for growth of the herpesvirus or a cell approved for herpesvirus growth and of fusing with the membrane of the diseased cell expressing the target molecule, and entering said cell.

2. The herpesvirus according to claim 1, wherein the first heterologous polypeptide ligand is inserted into one of the HVEM or nectin-1 binding sites and the second heterologous polypeptide ligand is inserted into the other HVEM or nectin-1 binding site.

3. The recombinant herpesvirus according to claim 2, wherein either the first or the second heterologous polypeptide ligand is inserted into the nectin-1 binding site of gD wherein the insertion is within amino acids 35 to 39 or a subset thereof or within amino acids 214 to 223 or a subset thereof of SEQ ID NO:1 or corresponding amino acids of a homologous gD.

4. The recombinant herpesvirus according to claim 2, wherein either the first or the second heterologous polypeptide ligand is inserted into the HVEM binding site of a gD, wherein the insertion is within amino acids 6 and 34 or between amino acids 24 and 25 of SEQ ID NO:1 or corresponding amino acids of a homologous gD.

5. The herpesvirus according to claim 1, wherein the first heterologous polypeptide ligand has a length of 5 to 131 amino acids.

6. The herpesvirus according to claim 5, wherein the first heterologous polypeptide ligand has a length of 5 to 120 amino acids.

7. The herpesvirus according to claim 1, wherein the first heterologous polypeptide ligand comprises a part of the GCN4 yeast transcription factor, an epitope of the GCN4 yeast transcription factor, a GCN4 epitope as identified by SEQ ID NO: 13, a part of the GCN4 yeast transcription factor comprising SEQ ID NO:12, or a peptide that is identified by SEQ ID NO:12.

8. The recombinant herpesvirus according to claim 1, wherein first heterologous polypeptide ligand is an antibody, an antibody derivative of an antibody mimetic, or a single-chain antibody (scFv).

9. The recombinant herpesvirus according to claim 1, wherein the diseased cell is a tumor cell, an infected cell, a degenerative disorder-associated cell, or a senescent cell, and wherein the target molecule is a tumor-associated receptor.

10. The herpesvirus according to claim 1, wherein the herpesvirus further encodes one or more molecules that modulate(s) the host immune response against the diseased cell.

11. A pharmaceutical composition comprising the recombinant herpesvirus according to claim 1 and a pharmaceutically acceptable carrier, optionally additionally comprising one or more molecule(s) that modulate(s) the host immune response against the diseased cell.

12. A cell comprising the recombinant herpesvirus according to claim 1.

13. A modified herpesvirus glycoprotein D (gD) said modified gD having:
   a) inactivated HVEM and nectin-1 binding sites,
   b) a first heterologous polypeptide ligand capable of binding to a target molecule present on a cell suitable for growth of the herpesvirus or a cell approved or herpesvirus growth fused to or inserted therein, and
   c) a second heterologous polypeptide ligand capable of binding to a target molecule present on a diseased cell fused to or inserted therein.

14. A nucleic acid molecule comprising a nucleic acid encoding a modified herpesvirus glycoprotein D (gD) said modified gD having:
   a) inactivated HVEM and nectin-1 binding sites,
   b) a first heterologous polypeptide ligand capable of binding to a target molecule present on a cell suitable for growth of the herpesvirus or a cell approved or herpesvirus growth fused to or inserted therein, and
   c) a second heterologous polypeptide ligand capable of binding to a target molecule present on a diseased cell fused to or inserted therein.

15. A vector comprising the nucleic acid molecule according to claim 14.

16. A cell comprising the nucleic acid molecule according to claim 14.

* * * * *